US010307475B2

(12) United States Patent
Wong et al.

(10) Patent No.: US 10,307,475 B2
(45) Date of Patent: *Jun. 4, 2019

(54) METHODS AND COMPOSITIONS FOR IMMUNIZATION AGAINST VIRUS

(71) Applicant: Academia Sinica, Taipei (TW)

(72) Inventors: Chi-Huey Wong, Taipei (TW); Che Ma, Taipei (TW); Cheng-Chi Wang, Taipei (TW); Juine-Ruey Chen, Sansing Township (TW)

(73) Assignee: Academia Sinica, Taipei (TW)

( * ) Notice: Subject to any disclaimer, the term of this patent is extended or adjusted under 35 U.S.C. 154(b) by 95 days.

This patent is subject to a terminal disclaimer.

(21) Appl. No.: 14/182,296

(22) Filed: Feb. 18, 2014

(65) Prior Publication Data
US 2015/0335728 A1 Nov. 26, 2015

Related U.S. Application Data

(62) Division of application No. 12/748,265, filed on Mar. 26, 2010, now Pat. No. 8,741,311.

(60) Provisional application No. 61/313,676, filed on Mar. 12, 2010, provisional application No. 61/164,389, filed on Mar. 28, 2009, provisional application No. 61/164,388, filed on Mar. 28, 2009, provisional application No. 61/164,387, filed on Mar. 28, 2009, provisional application No. 61/164,385, filed on Mar. 27, 2009.

(51) Int. Cl.
A61K 39/145 (2006.01)
C12N 7/00 (2006.01)
A61K 39/12 (2006.01)
C07K 16/10 (2006.01)
A61K 39/00 (2006.01)

(52) U.S. Cl.
CPC ............ A61K 39/145 (2013.01); A61K 39/12 (2013.01); C07K 16/1018 (2013.01); C12N 7/00 (2013.01); A61K 2039/55505 (2013.01); C07K 2317/76 (2013.01); C12N 2740/11034 (2013.01); C12N 2740/16034 (2013.01); C12N 2760/16122 (2013.01); C12N 2760/16134 (2013.01); C12N 2760/16171 (2013.01); C12N 2770/24134 (2013.01); Y02A 50/386 (2018.01)

(58) Field of Classification Search
None
See application file for complete search history.

(56) References Cited

U.S. PATENT DOCUMENTS

| 3,953,592 | A | 4/1976 | Peetermans |
| 4,318,903 | A | 3/1982 | Lobmann et al. |
| 4,338,296 | A | 7/1982 | Lobmann et al. |
| 6,103,238 | A | 8/2000 | Essex et al. |
| 6,803,225 | B2 | 10/2004 | Contreras et al. |
| 6,908,617 | B1 | 6/2005 | Wyatt et al. |
| 8,741,311 | B2 | 6/2014 | Wong et al. |
| 9,403,878 | B2 * | 8/2016 | Wong .................. A61K 39/145 |
| 9,920,347 | B2 | 3/2018 | Wong et al. |
| 2002/0045594 | A1 | 4/2002 | Volkin et al. |
| 2004/0047877 | A1 | 3/2004 | Leroux-Roels et al. |
| 2005/0075292 | A1 | 4/2005 | Weinberg |
| 2006/0121521 | A1 | 6/2006 | Dowling et al. |
| 2006/0188977 | A1 | 8/2006 | Schwartz et al. |
| 2007/0224205 | A1 | 9/2007 | Powell et al. |
| 2008/0050402 | A1 | 2/2008 | Zhou et al. |
| 2008/0118529 | A1 | 5/2008 | Gebbink et al. |
| 2008/0241918 | A1 | 10/2008 | Sasisekharan et al. |
| 2009/0017052 | A1 | 1/2009 | Bogoch et al. |
| 2010/0247571 | A1 | 9/2010 | Wong et al. |
| 2012/0219584 | A1 | 8/2012 | Nabel et al. |
| 2014/0011188 | A1 | 1/2014 | Wong et al. |
| 2016/0348144 | A1 | 12/2016 | Wong et al. |

FOREIGN PATENT DOCUMENTS

| CL | 2007-000529 | 2/2007 |
| CL | 2008-001543 | 5/2008 |
| CL | 2011-002354 | 9/2011 |
| EP | 0252302 A1 | 1/1988 |
| RU | 2283138 C2 | 9/2006 |

(Continued)

OTHER PUBLICATIONS

Hacker et al., Reduction of adenovirus E1A mRNA by RNAi results in enhanced recombinant protein expression in transiently transfected HEK293 cells, 2004, Gene, vol. 341, pp. 227-234.*
Fenouillet et al., Role of N-Linked Glycans of Envelope Glycoproteins in Infectivity of Human Immunodeficiency Virus Type 1, 1990, Journal of Virology, vol. 64, No. 6, pp. 2841-2848.*
Mishin et al., Effect of Hemagglutinin Glycosylation on Influenza Virus Susceptibility to Neuraminidase Inhibitors, 2005, Journal of Virology, vol. 79, No. 19, pp. 12416-12424.*
PCT/US2010/028968, Nov. 5, 2010, International Search Report and Written Opinion.

(Continued)

Primary Examiner — Benjamin P Blumel
(74) Attorney, Agent, or Firm — Wolf, Greenfield & Sacks, P.C.

(57) ABSTRACT

Immunogenic compositions comprising partially glycosylated viral glycoproteins for use as vaccines against viruses are provided. Vaccines formulated using mono-, di-, or tri-glycosylated viral surface glycoproteins and polypeptides provide potent and broad protection against viruses, even across strains. Pharmaceutical compositions comprising monoglycosylated hemagglutinin polypeptides and vaccines generated therefrom and methods of their use for prophylaxis or treatment of viral infections are disclosed. Methods and compositions are disclosed for influenza virus HA, NA and M2, RSV proteins F, G and SH, Dengue virus glycoproteins M or E, hepatitis C virus glycoprotein E1 or E2 and HIV glycoproteins gp120 and gp41.

9 Claims, 22 Drawing Sheets
(11 of 22 Drawing Sheet(s) Filed in Color)
Specification includes a Sequence Listing.

(56) References Cited

FOREIGN PATENT DOCUMENTS

| WO | WO 86/03224 A1 | 6/1986 |
|---|---|---|
| WO | WO 1987/005330 A1 | 9/1987 |
| WO | WO 1988/08718 | 11/1988 |
| WO | WO 00/69458 A2 | 11/2000 |
| WO | WO 01/30814 A1 | 5/2001 |
| WO | WO 2003/046150 A2 | 6/2003 |
| WO | WO 2003/057710 A2 | 7/2003 |
| WO | WO 2006/099592 A2 | 9/2006 |
| WO | WO 2007/061631 A2 | 5/2007 |
| WO | WO 2007/074188 A1 | 7/2007 |
| WO | WO 2007/133855 A2 | 11/2007 |
| WO | WO 2007/150054 A2 | 12/2007 |
| WO | WO 2008/094687 A2 | 8/2008 |
| WO | WO 2008/112017 A2 | 9/2008 |
| WO | WO 2010/122460 A1 | 10/2010 |

OTHER PUBLICATIONS

PCT/US2010/028968, Jun. 7, 2012, International Preliminary Report on Patentability.
EP 10756977.4, Oct. 31, 2013, Extended European Search Report.
Arora et al., Archives of Virology, 1997, 142(2):401-12.
Barr. I.G. et al. Adamantane Resistance in Influenza A(H1) Viruses Increased in 2007 in South East Asia but Decreased in Australia and Some Other Countries. Antiviral Research. Nov. 2008, vol. 80(2), pp. 200-205.
Besselaar, T.G. et al. Widespread Oseltamivir Resistance in Influenza A Viruses (H1N1), South Africa. Emerging Infectious Diseases. Nov. 11, 2008, vol. 14(11). pp. 1809-1810.
Bolmstedt, A. et al. Enhanced Immunogenicity of a Human Immunodeficiency Virus Type 1 env DNA Vaccine by Manipulating N-Glycosylation Signals Effects of Elimination of the V3N306 Glycan. Vaccine. 2002. vol. 20(3-4), pp. 397-405.
Caton et al., The antigenic structure of the nfluenza virus A/PR/8/34 hemagglutinin (H1 subtype), Cell, 1982, 31:417-427.
Chen et al., A consensus—hemagglutinin-based DNA vaccine that protects mice against divergent H5N1 influenza viruses, PNAS, 2008, 105(36):13538-13543.
Datema et al., Effect of Energy Depletion on the Glycosylation of a Viral Glycoprotein, Journal of Biological Chemistry, 1981, 256:11191:11198.
Domingo. C. et al. Envelope glycoprotein (Dengue Virus], GenBank Direct Submission, Accession No. AAY34774 (online]. Apr. 28, 2006 [retrieved on Jun. 3, 2010]. Retrieved from the internet<URL: http://www.ncbLnlm. nih.gov/proteinI63175415>.
Doranz et al., Journal of Virology, 1999, 73:10346-10358.
Fournillier. A. et al. Induction of Hepatitis C Virus E1 Envelope Protein-Specific Immune Response Can Be Enhanced by Mutation of N-Glycosylation Sites. Journal of Virology. Dec. 2001, vol. 75(24). pp. 12088-12097.
Galarza et al., Virus-like particle vaccine conferred complete protection against a lethal influenza virus challenge, Viral Immunology, 2005, 18:365-372,2005.
Garten, R. et al., Influenza A Virus (A1WisconsinI01/2007(H1N1«). GenBank Direct Submission. Accession No. ABU50572 (online]. Jun. 5, 2008 [retrieved on Jun. 3, 2010]. Retrieved from the Internet<URL: http://wvvw.ncbLnlm. nih.gov/proteinll 56123388>.
Gitelman et al., The role of carbohydrate in determining the immunochemical properties of the hemagglutinin of influenza A virus, Archives of Virology, 1981, 67:253-266.
Keil et al., Virology, 1984, 133(1):77-91.
Kuroda et al., The oligosaccharides of influenza virus hemagglutinin expressed in insect cells by a baculovirus vector, Virology, 1990, 174:418-429.
Martinet et al., Protection of mice against a lethal influenza challenge by immunization with yeast-derived recombinant influenza neuraminidase, European Journal of Biochemistry, 1997, 247:332-338.

Mir-Shekari et al., The glycosylation of the influenza A virus hemagglutinin by mammalian cells. A site-specific study. J Biol Chem. Feb. 14, 1997; 272(7):4027-36.
Munk et al., Carbohydrate masking of an antigenic epitope of influenza virus haemagglutinin independent of oligosaccharide size, Glycobiology, 1992, vol. 2, No. 3, pp. 233-240.
Rimmelzwaan et al., Curr Opin Pharmacol, 2001, 1(5):491-6.
Stevens et al., Recent avian H5N1 viruses exhibit increased propensity for acquiring human receptor specificity. J Mol Biol. Sep. 19, 2008;381(5):1382-94.
Tolley. K.P. et al. Attachment Glycoprotein (G) (Respiratory Syncytial Virus]. GenBank Direct Submission. Accession No. AAC57036 [online]. Mar. 28, 1997 (retrieved on Jun. 3, 2010]. Retrieved from the Internet: <URL: http://www.ncbi.nlm.nih.gov/protein/1912305>.
Viswanathan et al., Glycans as receptors for influenza pathogenesis. Glycoconj J. Aug. 2010;27(6):561-70.
Wagner et al., Interdependence of Hemagglutinin Glycosylation and Neuraminidase as Regulators of Influenza Virus Growth: a Study by Reverse Genetics, J. Virol. (2002) 74(14):6316-6323.
Wang et al., PNAS, 2009, 106(43):18137-42.
Wei et al, Journal of Virology, 2008, 82(13):6200-8.
Who Global Alert and Response. Influenza-Like Illness in the United States and Mexico [online]. Apr. 24, 2009 [retrieved on Jun. 7, 2010]. Retrieve from the Internet <URL: http://www.who.inticsr/don12009_04_24/en/index. html>.
Treanor et al., Safety and immunogenicity of a recombinant hemagglutinin vaccine for H5 influenza in humans. Vaccine. Feb. 8, 2001;19(13-14):1732-7.
Wang et al., Expression and purification of an influenza hemagglutinin—one step closer to a recombinant protein-based influenza vaccine. Vaccine. Mar. 15, 2006;24(12):2176-85. Epub Nov. 10, 2005.
[No Author Listed] Millipore, MRCF0R030: Micron-30kDa Centrifugal Filter Unit with Ultracel-30 membrane. Specification Sheet, Merck KGaA, Darmstadt, Germany, 2014.
Brug et al., Antiviral action of derivatives of omega-aminoacetophenone. Br J Pharmacol Chemother. Dec. 1958;13(4):404-10.
De Vries et al., Glycan-dependent immunogenicity of recombinant soluble trimeric hemagglutinin. J Virol. Nov. 2012;86(21):11735-44. doi: 10.1128/JVI.01084-12. Epub Aug. 22, 2012.
De Vries et al., The influenza A virus hemagglutinin glycosylation state affects receptor-binding specificity. Virology. Jul. 20, 2010;403(1):17-25. doi: 10.1016/j.virol.2010.03.047.
Durantel et al., Study of the mechanism of antiviral action of iminosugar derivatives against bovine viral diarrhea virus. J Virol. Oct. 2001;75(19):8987-98.
Elbein et al., Kifunensine, a potent inhibitor of the glycoprotein processing mannosidase I., J Biol Chem. Sep. 15, 1990;265(26):15599-605.
Elbein et al., The effect of deoxymannojirimycin on the processing of the influenza viral glycoproteins. Arch Biochem Biophys. Dec. 1984;235(2):579-88.
Karaivanova et al., Processing of viral envelope glycoprotein by the endomannosidase pathway: evaluation of host cell specificity. Glycobiology. Jul. 1998;8(7):725-30.
Karaivanova et al., Sulphation of N-linked oligosaccharides of vesicular stomatitis and influenza virus envelope glycoproteins: host cell specificity, subcellular localization and identification of substituted saccharides. Biochem J. Feb. 1, 1998;329 ( Pt 3):511-8.
Kong et al., Expression-system-dependent modulation of HIV-1 envelope glycoprotein antigenicity and immunogenicity. J Mol Biol. Oct. 15, 2010;403(1):131-47. doi: 10.1016/j.jmb.2010.08.033. Epub Aug. 25, 2010.
Qing et al., A high-throughput assay using dengue-1 virus-like particles for drug discovery. Antiviral Res. May 2010;86(2):163-71. doi: 10.1016/j.antiviral.2010.02.313. Epub Feb. 12, 2010.
Saito et al., Effect of glycosylation and glucose trimming inhibitors on the influenza A virus glycoproteins. J Vet Med Sci. Jun. 2000;62(6):575-81.

(56) References Cited

OTHER PUBLICATIONS

Scanlan et al., Inhibition of mammalian glycan biosynthesis produces non-self antigens for a broadly neutralising, HIV-1 specific antibody. J Mol Biol. Sep. 7, 2007;372(1):16-22. Epub Jun. 16, 2007.

Schwarzer et al., Glycan analysis in cell culture-based influenza vaccine production: influence of host cell line and virus strain on the glycosylation pattern of viral hemagglutinin. Vaccine. Jul. 9, 2009;27(32):4325-36. doi: 10.1016/j.vaccine.2009.04.076.

Vlietinck et al., Plant-derived leading compounds for chemotherapy of human immunodeficiency virus (HIV) infection. Planta Med. Mar. 1998;64(2):97-109.

Wei et al., Cross-neutralization of 1918 and 2009 influenza viruses: role of glycans in viral evolution and vaccine design. Sci Transl Med. Mar. 24, 2010;2(24):24ra21. doi: 10.1126/scitranslmed.3000799.

World Health Organization. WHO Expert Committee on Biological Standardization. Fifty-sixth Report. WHO, Geneva, Switzerland, 2007, pp. 1-340.

World Health Organization. WHO Manual on Animal Influenza Diagnosis and Surveillance, WHO/CDS/CSR/NCS/2002.5, Dec. 18, 1997, pp. 62-63.

Wu et al., Antiviral effects of an iminosugar derivative on flavivirus infections. J Virol. Apr. 2002;76(8):3596-604.

Zhang et al., Hemagglutinin glycosylation modulates the pathogenicity and antigenicity of the H5N1 avian influenza virus. Vet Microbiol. Feb. 25, 2015;175(2-4):244-56. doi: 10.1016/j.vetmic.2014.12.011. Epub Dec. 18, 2014.

PCT/US2011/059449, Apr. 4, 2012, International Search Report and Written Opinion.

PCT/US2011/059449, May 16, 2013, International Preliminary Report on Patentability.

PCT/US2011/059449, Apr. 9, 2014, Extended European Search Report.

Chandrasekaran et al., Glycan topology determines human adaptation of avian H5N1 virus hemagglutinin. Nat Biotechnol. Jun. 2008;26(1):107-13. doi: 10.1038/nbt1375. Epub Jan. 6, 2008.

Gloster et al., Glycosidase inhibition: assessing mimicry of the transition state. Org Biomol Chem. Jan. 21, 2010;8(2):305-20. doi:10.1039/b915870g. Epub Nov. 5, 2009.

Johansson et al., Purified influenza virus hemagglutinin and neuraminidase are equivalent in stimulation of antibody response but induce contrasting types of immunity to infection. J Virol. Mar. 1989;63(3):1239-46.

\* cited by examiner

| N-glycan composition | (m/z) | | |
|---|---|---|---|
| | $HA_{fg}$ | $HA_{dk}$ | $HA_{hm}$ |
| $Hex_5HexNAc_2$ | 1579.7 | 1579.9 | 1579.8 |
| $Hex_6HexNAc_2$ | 1783.9 | 1783.9 | 1783.9 |
| $Hex_3HexNAc_4Fuc_1$ | 1835.6 | 1835.8 | ND |
| $Hex_7HexNAc_2$ | 1988.0 | 1987.4 | 1988.0 |
| $Hex_4HexNAc_4Fuc_1$ | 2040.0 | 2040.1 | ND |
| $Hex_3HexNAc_5Fuc_1$ | 2081.0 | 2081.2 | ND |
| $Hex_8HexNAc_2$ | 2192.1 | 2192.2 | 2192.1 |
| $Hex_5HexNAc_4Fuc_1$ | 2244.1 | 2244.2 | ND |
| $Hex_4HexNAc_5Fuc_1$ | 2285.1 | 2285.2 | ND |
| $Hex_9HexNAc_2$ | 2396.2 | 2396.2 | 2396.2 |
| $Hex_5HexNAc_5Fuc_1$ | 2489.2 | 2489.3 | ND |
| $Hex_5HexNAc_4Fuc_1NeuAc_1$ | 2605.3 | ND | ND |
| $Hex_5HexNAc_6Fuc_1$ | 2693.3 | 2693.4 | ND |
| $Hex_6HexNAc_5Fuc_1$ | 2734.4 | 2734.4 | ND |
| $Hex_5HexNAc_5Fuc_1NeuAc_1$ | 2850.4 | ND | ND |
| $Hex_6HexNAc_6Fuc_1$ | 2938.5 | 2938.5 | ND |
| $Hex_5HexNAc_6Fuc_1NeuAc_1$ | 2966.5 | ND | ND |
| $Hex_6HexNAc_5Fuc_1NeuAc_1$ | 3054.5 | ND | ND |
| $Hex_7HexNAc_6Fuc_1$ | 3142.6 | 3142.5 | ND |
| $Hex_6HexNAc_7Fuc_1$ | 3316.5 | 3316.6 | ND |
| $Hex_7HexNAc_7Fuc_1$ | 3387.8 | 3387.6 | ND |
| $Hex_6HexNAc_6Fuc_1NeuAc_1$ | 3415.7 | ND | ND |
| $Hex_6HexNAc_6Fuc_1NeuAc_2$ | 3503.8 | ND | ND |
| $Hex_7HexNAc_6Fuc_1NeuAc_1$ | 3677.9 | ND | ND |
| $Hex_6HexNAc_7Fuc_1NeuAc_2$ | 3776.9 | ND | ND |
| $Hex_7HexNAc_6Fuc_1NeuAc_2$ | 3865.0 | ND | ND |
| $Hex_7HexNAc_7Fuc_1NeuAc_2$ | 4038.0 | ND | ND |
| $Hex_8HexNAc_7Fuc_1NeuAc_2$ | 4225.2 | ND | ND |
| $Hex_8HexNAc_8Fuc_1NeuAc_3$ | 4586.5 | ND | ND |

FIG. 10

ΔΔG OF HA GLYCOSYLATED VARIANTS IN RESPONSE TO A2,3 SIALOSIDES 1-15

FIG. 11

| | HA-Avg | HA-A | HA-Am | HA-Avg |
|---|---|---|---|---|
| 1→2 | -0.384 | -0.079 | -0.094 | -0.230 |
| 1→3 | -0.378 | -0.160 | -0.477 | -0.398 |
| 1→6 | 0.617 | 0.706 | 0.113 | 0.460 |
| 1→7 | -0.616 | -0.068 | -0.132 | -0.616 |
| 1→8 | 0.659 | 0.999 | 0.454 | 0.611 |
| 1→9 | ND | 0.223 | -0.200 | 0.842 |
| 1→10 | 0.528 | -0.055 | -0.269 | -0.055 |
| 8→11 | 1.646 | ND | 0.236 | 0.870 |
| 8→12 | -0.023 | -0.370 | 0.393 | -0.798 |
| 8→13 | -1.653 | -1.275 | -0.602 | -0.551 |
| 9→14 | ND | 0.460 | 1.361 | 0.410 |
| 6→7 | -2.044 | -1.434 | -0.026 | -0.467 |
| 13→14 | -0.117 | -0.226 | 0.186 | 0.172 |

DIFFERENCES IN BINDING FREE ENERGY CHANGES BETWEEN DIFFERENT SIALOSIDE LIGANDS IN RESPONSE TO HA VARIANTS

HA$_{fg}$ and HA$_{mg}$ denote fully glycosylated and mono-glycosylated consensus H5 as ant

FIG. 18
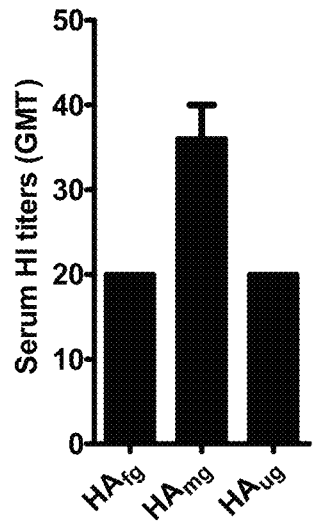
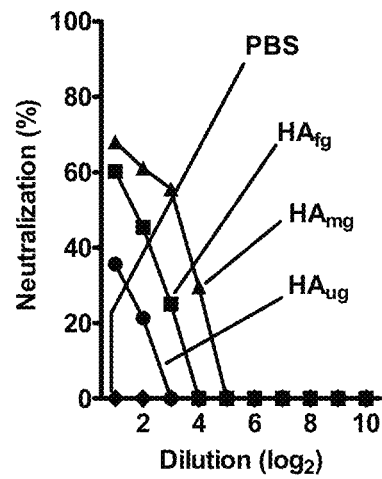

A  B

SEQUENCE LISTING

```
<160> NUMBER OF SEQ ID NOS: 20

<210> SEQ ID NO 1
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 1

Pro Gln Arg Glu Arg Arg Arg Lys Lys Arg Gly
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Pro Gln Arg Glu Arg Gly
1               5

<210> SEQ ID NO 3
<211> LENGTH: 43
<212> TYPE: PRT
<213> ORGANISM: Artificial Sequence
<220> FEATURE:
<223> OTHER INFORMATION: Synthetic

<400> SEQUENCE: 3

Leu Val Pro Arg Gly Ser Pro Gly Ser Gly Tyr Ile Pro Glu Ala Pro
1               5                   10                  15

Arg Asp Gly Gln Ala Tyr Val Arg Lys Asp Gly Glu Trp Val Leu Leu
            20                  25                  30

Ser Thr Phe Leu Gly His His His His His
        35                  40

<210> SEQ ID NO 4
<211> LENGTH: 564
<212> TYPE: PRT
<213> ORGANISM: Influenza A virus
```

<400> SEQUENCE: 4

Met Glu Lys Ile Val Leu Leu Phe Ala Ile Val Ser Leu Val Lys Ser
1               5                   10                  15

Asp Gln Ile Cys Ile Gly Ser His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Gly Leu Phe Gly Ala Ile Ala Gly Phe Ile Glu
            340                 345                 350

Gly Gly Trp Gln Gly Met Val Asp Gly Trp Tyr Gly Tyr His His Ser
        355                 360                 365

Asn Glu Gln Gly Ser Gly Tyr Ala Ala Asp Lys Glu Ser Thr Gln Lys
    370                 375                 380

Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg

```
                405                 410                 415

Arg Ile Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
        435                 440                 445

Leu Asp Phe His Asp Ser Asn Val Lys Asn Leu Tyr Asp Lys Val Arg
    450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Glu Glu Ala Arg Leu Lys Arg Glu
            500                 505                 510

Glu Ile Ser Gly Val Asp Ile Arg Ser Leu Val Pro Arg Gly Ser Pro
        515                 520                 525

Gly Ser Gly Tyr Ile Pro Glu Ala Pro Arg Asp Gly Gln Ala Tyr Val
    530                 535                 540

Arg Lys Asp Gly Glu Trp Val Leu Leu Ser Thr Phe Leu Gly His His
545                 550                 555                 560

His His His His

<210> SEQ ID NO 5
<211> LENGTH: 1695
<212> TYPE: DNA
<213> ORGANISM: Influenza A virus

<400> SEQUENCE: 5
atggagaaga tcgtgctgct gttcgccatc gtgagcctgg tgaagagcga ccagatctgc     60
atcggatccc acgccaacaa cagcaccgag caggtggaca ccatcatgga gaagaacgtg    120
accgtgaccc acgcccagga catcctggag aagacccaca acggcaagct gtgcgacctg    180
gacggcgtga agcctctgat cctgagagac tgcagcgtgg ccggctggct gctgggcaac    240
cctatgtgcg acgagttcat caacgtgcct gagtggagct acatcgtgga gaaggccaac    300
cctgccaacg acctgtgcta ccctggcgac ttcaacgact acgaggagct gaagcacctg    360
ctgagcagaa tcaaccactt cgagaagatc cagatcatcc ctaagagcag ctggagcagc    420
cacgaggcca gcagcggcgt gagcagcgcc tgcccttacc agggcaagag cagcttcttc    480
agaaacgtgg tgtggctgat caagaagaac agcacctacc ctaccatcaa gagaagctac    540
aacaacacca accaggagga cctgctggtg ctgtggggca tccaccaccc taacgacgcc    600
gccgagcaga ccaagctgta ccagaaccct accacctaca tcagcgtggg caccagcacc    660
ctgaaccaga gactggtgcc taagatcgcc accagaagca aggtgaacgg ccagagcggc    720
agaatggagt tcttctggac catcctgaag cctaacgacg ccatcaactt cgagagcaac    780
ggcaacttca tcgcccctga gtacgcctac aagatcgtga agaagggcga cagcaccatc    840
atgaagagcg agctggagta cggcaactgc aacaccaagt gccagacccc tatgggcgcc    900
atcaacagca gcatgccttt ccacaacatc caccctctga ccatcggcga gtgccctaag    960
tacgtgaaga gcaacagact ggtgctggcc accggcctga gaaacagccc tcagagagag   1020
agaggcctgt tcggcgccat cgccggcttc atcgagggcg gctggcaggg catggtggac   1080
ggctggtacg gctaccacca cagcaacgag cagggcagcg gctacgccgc cgacaaggag   1140
agcacccaga aggccatcga cggcgtgacc aacaaggtga acagcatcat cgacaagatg   1200
```

-continued

```
aacacccagt cgaggccgt gggcagagag ttcaacaacc tggagagaag aatcgagaac    1260
ctgaacaaga gatggagga cggcttcctg gacgtgtgga cctacaacgc cgagctgctg    1320
gtgctgatgg agaacgagag aaccctggac ttccacgaca gcaacgtgaa gaacctgtac    1380
gacaaggtga gactgcagct gagagacaac gccaaggagc tgggcaacgg ctgcttcgag    1440
ttctaccaca agtgcgacaa cgagtgcatg gagagcgtga aaacggcac ctacgactac    1500 cctcagtaca gcgaggaggc cagactgaag agagaggaga tcagcggcgt ggatatcaga    1560
tctctggtgc aagaggatc tccaggatct ggatacatcc cagaggctcc aagagatgga    1620
caagcttacg tgagaaagga cggagagtgg gtgctgctgt ctactttcct gggacaccac    1680
caccaccacc actaa                                                    1695
```

<210> SEQ ID NO 6
<211> LENGTH: 567
<212> TYPE: PRT
<213> ORGANISM: Influenza A virus

<400> SEQUENCE: 6

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285
```

```
Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Asp Ile Arg Ser Leu Val Pro Arg
            515                 520                 525

Gly Ser Pro Gly Ser Gly Tyr Ile Pro Glu Ala Pro Arg Asp Gly Gln
            530                 535                 540

Ala Tyr Val Arg Lys Asp Gly Glu Trp Val Leu Leu Ser Thr Phe Leu
545                 550                 555                 560

Gly His His His His His His
                565

<210> SEQ ID NO 7
<211> LENGTH: 1720
<212> TYPE: DNA
<213> ORGANISM: Influenza A virus

<400> SEQUENCE: 7
atggcgcgcc gctagcatga aggccatcct ggttgtgctg ctgtacacct tcgctaccgc      60
caacgccgat accctgtgca tcggctacca cgccaacaac agcaccgaca ccgtggatac     120
cgtgctggaa aagaacgtga ccgtgaccca cagcgtgaac ctgctggaag ataagcacaa     180
cggcaagctg tgcaagctga gaggcgtggc ccctctgcac ctgggcaagt gcaatatcgc     240
cggctggatc ctgggcaacc ccgagtgcga gagcctgagc accgccagca gctggtccta     300
catcgtggag acacccagca gcgacaatgg cacctgttac cccggcgact tcatcgacta     360
cgaggaactg cgggagcagc tgagcagcgt gtccagcttc gagcggttcg agatcttccc     420
caagaccagc tcttggccca accacgacag caacaagggc gtgaccgccg cctgtcctca     480
```

-continued

```
cgctggcgcc aagagcttct acaagaacct gatctggctg gtcaagaagg caacagcta    540 ccccaaactg agcaagagct acatcaacga caagggcaaa gaagtgctgg tgctgtgggg    600
catccaccac cctagcacca gcgccgacca gcagagcctg taccagaacg ccgacgccta    660
cgtgttcgtg ggcagcagcc ggtacagcaa gaagttcaag cccgagatcg ccatcagacc    720
caaagtgcgg gaccaagagg gccggatgaa ctactactgg accctggtgg agcccggcga    780
caagatcacc ttcgaggcca ccggcaatct ggtcgtgccc agatacgcct cgccatgga    840 aagaaacgcc ggcagcggca tcatcatcag cgacaccccc gtgcacgact gcaacaccac    900
ctgtcagacc cccaaaggcg ccatcaacac cagcctgccc ttccagaaca tccacccat    960 caccatcggc aagtgcccta gtacgtgaa gtctaccaag ctgaggctgg ccacaggcct    1020
gcggaacatc cccagcatcc agagcagagg cctgtttggc gccattgccg gctttatcga    1080
gggcggctgg accggaatgg tggatggatg gtatggctac caccaccaga atgagcaggg    1140
aagcggctac gccgccgacc tgaagtccac acagaacgcc atcgacgaga tcaccaacaa    1200
agtgaactca gtgatcgaga gatgaacac ccagttcacc gccgtgggca agaattcaa    1260 ccacctggaa aagcggatcg agaacctgaa caagaaggtg gacgacggct tcctggacat    1320 ctggaccta aacgccgagc tgctcgtgct gctggaaaac gagcggaccc tggactacca    1380
cgactccaac gtgaagaatc tgtacgagaa agttcgctcc cagctgaaga caacgccaa    1440 agagatcggc aacggctgct tcgagttcta ccacaagtgc gacaacacct gtatggaaag    1500
cgtgaagaac ggcacctacg actacccaa gtacagcgag aagccaagc tgaaccggga    1560 agagatcgac ggcgtggata tcagatctct ggtgccaaga ggatctccag gatctgata    1620 catcccagag gctccaagag atggacaagc ttacgtgaga aaggacggag agtgggtgct    1680
gctgtctact ttcctgggac accaccacca ccaccactaa                          1720
```

<210> SEQ ID NO 8
<211> LENGTH: 567
<212> TYPE: PRT
<213> ORGANISM: Influenza A virus

<400> SEQUENCE: 8

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Ser Ala Ser Cys Ser His Asn Gly Lys Ser Ser
145                 150                 155                 160

```
Phe Tyr Arg Asn Leu Leu Trp Leu Thr Gly Lys Asn Gly Leu Tyr Pro
                165                 170                 175

Asn Leu Ser Lys Ser Tyr Ala Asn Asn Lys Glu Lys Glu Val Leu Val
            180                 185                 190

Leu Trp Gly Val His His Pro Pro Asn Ile Gly Asp Gln Arg Ala Leu
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Pro
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Asp Ile Arg Ser Leu Val Pro Arg
        515                 520                 525

Gly Ser Pro Gly Ser Gly Tyr Ile Pro Glu Ala Pro Arg Asp Gly Gln
    530                 535                 540

Ala Tyr Val Arg Lys Asp Gly Glu Trp Val Leu Leu Ser Thr Phe Leu
545                 550                 555                 560

Gly His His His His His His
                565
```

<210> SEQ ID NO 9
<211> LENGTH: 1704
<212> TYPE: DNA
<213> ORGANISM: Influenza A virus

<400> SEQUENCE: 9

| | | | | | |
|---|---|---|---|---|---|
| atgaaggtga | aactgctggt | gctgctgtgc | accttcaccg | ccacctacgc | cgacaccatc | 60 |
| tgcatcggct | accacgccaa | caacagcacc | gacaccgtgg | ataccgtgct | ggaaaagaac | 120 |
| gtgaccgtga | cccacagcgt | gaacctgctg | aagatagcc | acaacggcaa | gctgtgcctg | 180 |
| ctgaagggca | ttgccccct | gcagctgggc | aactgtagcg | tggccggctg | gattctgggc | 240 |
| aaccccgagt | gcgagctgct | gatcagcaaa | gagtcctggt | cctacatcgt | ggagacaccc | 300 |
| aaccccgaga | cggcacctg | ttaccccggc | tacttcgccg | actacgagga | actgagagag | 360 |
| cagctgtcct | ctgtctccag | cttcgagcgg | ttcgagatct | tccccaaaga | gagcagctgg | 420 |
| cccaaccaca | ccgtgacaaa | gggcgtgagc | gccagctgct | cccacaatgg | caagagcagc | 480 |
| ttctaccgga | acctgctgtg | gctgaccggc | aagaacggc | tgtaccccaa | cctgagcaag | 540 |
| agctatgcca | caacaaaga | gaaagaggtc | ctcgtcctct | ggggcgtgca | ccaccccccc | 600 |
| aacatcggcg | accagcgggc | cctgtaccac | accgagaacg | cctacgtgtc | cgtggtgtcc | 660 |
| agccactaca | gcagacggtt | caccccgag | atcgccaaga | ggcccaaagt | gcgggaccag | 720 |
| gaaggccgga | tcaactacta | ctggaccctg | ctggaacccg | cgacaccat | catcttcgag | 780 |
| gccaacggca | acctgatcgc | ccccagatac | gcctttgccc | tgagcagagg | cttcggcagc | 840 |
| ggcatcatca | ccagcaacgc | ccccatggac | gagtgcgacg | ccaagtgtca | gacccccag | 900 |
| ggcgccatca | acagcagcct | gcccttccag | aacgtgcacc | ccgtgaccat | cggcgagtgc | 960 |
| cctaagtacg | tgcggagcac | caagctgaga | atggtgaccg | gcctgcggaa | catcccagc | 1020 |
| atccagagca | gaggcctgtt | tggcgccatt | gccggctta | tcgagggcgg | ctggaccgga | 1080 |
| atggtggacg | gtggtacgg | ctaccaccac | cagaatgagc | agggcagcgg | ctacgccgcc | 1140 |
| gatcagaagt | ccacccagaa | cgctatcaac | ggcatcacca | acaaagtgaa | cagcgtgatc | 1200 |
| gagaagatga | cacccagtt | caccgccgtg | gcaaagagt | tcaacaagct | ggaacggcgg | 1260 |
| atggaaaacc | tgaacaagaa | ggtggacgac | ggcttcctgg | acatctggac | ctacaacgcc | 1320 |
| gagctgctgg | tcctgctgga | aaacgagcgg | accctggact | ccacgacag | caacgtgaag | 1380 |
| aacctgtacg | agaaagtgaa | gtcccagctg | aagaacaacg | ccaaagagat | cggcaacggc | 1440 |
| tgcttcgagt | tctaccacaa | gtgcaacgac | gagtgcatgg | aaagcgtgaa | gaacggcaca | 1500 |
| tacgactacc | ccaagtacag | cgaggaaagc | aagctgaacc | gggagaagat | cgacggcgtg | 1560 |
| gatatcagat | ctctggtgcc | aagaggatct | ccaggatctg | gatacatccc | agaggctcca | 1620 |
| agagatggac | aagcttacgt | gagaaaggac | ggagagtggg | tgctgctgtc | tacttcctg | 1680 |
| ggacaccacc | accaccacca | ctaa | |

-continued

```
Val Asp Thr Val Leu Glu Lys Asn Val Thr Val Thr His Ser Val Asn
         35                  40                  45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Thr Pro Asn Pro Glu Asn Gly Thr Cys Tyr Pro Gly His Phe
             100                 105                 110

Ala Asp Tyr Glu Glu Leu Arg Glu Gln Leu Ser Ser Val Ser Ser Phe
             115                 120                 125

Glu Arg Phe Glu Ile Phe Pro Lys Glu Ser Ser Trp Pro Asn His Asp
         130                 135                 140

Thr Val Thr Gly Val Ser Ala Ser Cys Ser His Asn Gly Glu Ser Ser
145                 150                 155                 160

Phe Tyr Arg Asn Leu Leu Trp Leu Thr Gly Lys Asn Gly Leu Tyr Pro
                 165                 170                 175

Asn Leu Ser Lys Ser Tyr Ala Asn Asn Lys Glu Lys Glu Val Leu Val
             180                 185                 190

Leu Trp Gly Val His His Pro Pro Asn Ile Gly Asp Gln Lys Ala Leu
         195                 200                 205

Tyr His Thr Glu Asn Ala Tyr Val Ser Val Val Ser Ser His Tyr Ser
 210                 215                 220

Arg Lys Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                 245                 250                 255

Ile Ile Phe Glu Ala Asn Gly Asn Leu Ile Ala Pro Arg Tyr Ala Phe
             260                 265                 270

Ala Leu Ser Arg Gly Phe Gly Ser Gly Ile Ile Asn Ser Asn Ala Pro
         275                 280                 285

Met Asp Lys Cys Asp Ala Lys Cys Gln Thr Pro Gln Gly Ala Ile Asn
 290                 295                 300

Ser Ser Leu Pro Phe Gln Asn Val His Pro Val Thr Ile Gly Glu Cys
305                 310                 315                 320

Pro Lys Tyr Val Arg Ser Ala Lys Leu Arg Met Val Thr Gly Leu Arg
                 325                 330                 335

Asn Ile Pro Ser Ile Gln Ser Arg Gly Leu Phe Gly Ala Ile Ala Gly
             340                 345                 350

Phe Ile Glu Gly Gly Trp Thr Gly Met Val Asp Gly Trp Tyr Gly Tyr
         355                 360                 365

His His Gln Asn Glu Gln Gly Ser Gly Tyr Ala Ala Asp Gln Lys Ser
 370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                 405                 410                 415

Leu Glu Arg Arg Met Glu Asn Leu Asn Lys Lys Val Asp Asp Gly Phe
             420                 425                 430

Leu Asp Ile Trp Thr Tyr Asn Ala Glu Leu Leu Val Leu Leu Glu Asn
         435                 440                 445
```

```
Glu Arg Thr Leu Asp Phe His Asp Ser Asn Val Lys Asn Leu Tyr Glu
            450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Asp Ile Arg Ser Leu Val Pro Arg
            515                 520                 525

Gly Ser Pro Gly Ser Gly Tyr Ile Pro Glu Ala Pro Arg Asp Gly Gln
530                 535                 540

Ala Tyr Val Arg Lys Asp Gly Glu Trp Val Leu Leu Ser Thr Phe Leu
545                 550                 555                 560

Gly His His His His His His
            565

<210> SEQ ID NO 11
<211> LENGTH: 1704
<212> TYPE: DNA
<213> ORGANISM: Influenza A virus

<400> SEQUENCE: 11
atgaaggtga aactgctggt gctgctgtgc accttcaccg ccacctacgc cgacaccatc        60
tgcatcggct accacgccaa caacagcacc gacaccgtgg ataccgtgct ggaaaagaac       120
gtgaccgtga cccacagcgt gaacctgctg aagatagcc acaacggcaa gctgtgcctg        180
ctgaagggca ttgccccct gcagctgggc aactgtagcg tggccggctg gattctgggc       240
aaccccgagt gcgagctgct gatctccaaa gagtcctggt cttacatcgt ggagacaccc       300
aaccccgaga acggcaccctg ttaccccggc cacttcgccg actacgagga actgcgggag      360
cagctgagca gcgtgtccag cttcgagcgg ttcgagatct ccccaaaga gagcagctgg        420 cccaaccacg ataccgtgac cggcgtgagc gccagctgtt cccacaacgg cgagagcagc      480
ttctaccgga acctgctgtg gctgaccggc aagaacggcc tgtaccccaa cctgagcaag      540
agctatgcca acaacaaaga gaaggaagtc ctggtcctct ggggcgtgca ccaccccccc      600
aacatcggcg accagaaggc cctgtaccac accgagaacg cctacgtgtc cgtggtgtcc      660
agccactaca gccggaagtt caccccccgag atcgccaaga ggcccaaagt gcgggaccag     720
gaaggccgga tcaactacta ctggaccctg ctggaacccg cgacaccat catcttcgag       780 gccaacggca acctgatcgc ccccagatac gcctttgccc tgagcagagg cttcggcagc     840
ggcatcatca cagcaacgc ccccatggac aagtgcgacg ccaagtgcca gacaccccag       900
ggcgccatca cagctccct gcccttccag aacgtgcacc ccgtgaccat cggcgagtgc       960
cctaagtacg tgcggagcgc caagctgaga atggtgaccg gcctgcggaa catccccagc      1020
atccagagca gaggcctgtt tggcgccatt gccggcttta tcgagggcgg ctggaccgga      1080
atggtggacg gtggtacgg ctaccaccac cagaatgagc agggcagcgg ctacgccgcc       1140
gatcagaagt ccacccagaa cgccatcaac ggcatcacca caaagtgaa cagcgtgatc       1200 gagaagatga cacccagtt caccgccgtg ggcaaagagt caacaagct ggaacggcgg        1260 atggaaaacc tgaacaagaa ggtggacgac ggcttcctgg acatctggac ctacaacgcc       1320
gagctgctgt gctgctgga aaacgagcgg accctggact ccacgacag caacgtgaag       1380 aacctgtacg agaaagtgaa gtcccagctg aagaacaacg ccaaagagat cggcaacggc      1440
```

```
tgcttcgagt tctaccacaa gtgcaacgac gagtgcatgg aaagcgtgaa gaacggcaca   1500
tacgactacc ccaagtacag cgaggaaagc aagctgaacc gggagaagat cgacggcgtg   1560
gatatcagat ctctggtgcc aagaggatct ccaggatctg gatacatccc agaggctcca   1620
agagatggac aagcttacgt gagaaaggac ggagagtggg tgctgctgtc tactttcctg   1680
ggacaccacc accaccacca ctaa                                          1704

<210> SEQ ID NO 12
<211> LENGTH: 298
<212> TYPE: PRT
<213> ORGANISM: Human respiratory syncytial virus

<400> SEQUENCE: 12

Met Ser Lys Asn Lys Asp Gln Arg Thr Thr Lys Thr Leu Glu Lys Thr
1               5                   10                  15

Trp Asp Thr Leu Asn His Leu Leu Phe Ile Ser Ser Cys Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Phe Ser Asn Leu Ser Glu Thr Thr Ser Gln Thr Thr
            100                 105                 110

Thr Ile Leu Ala Ser Thr Thr Pro Ser Val Lys Ser Thr Leu Gln Ser
        115                 120                 125

Thr Thr Val Lys Thr Lys Asn Thr Thr Thr Thr Lys Ile Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Ile
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Lys Pro Thr Ile Asn Thr Thr Lys
225                 230                 235                 240

Thr Asn Ile Arg Thr Thr Leu Leu Thr Asn Asn Thr Thr Gly Asn Pro
                245                 250                 255

Glu His Thr Ser Gln Lys Gly Thr Leu His Ser Thr Ser Ser Asp Gly
            260                 265                 270

Asn Pro Ser Pro Ser Gln Val Tyr Thr Thr Ser Glu Tyr Leu Ser Gln
        275                 280                 285

Pro Pro Ser Pro Ser Asn Thr Thr Asn Gln
    290                 295

<210> SEQ ID NO 13
<211> LENGTH: 495
```

```
<212> TYPE: PRT
<213> ORGANISM: Dengue virus

<400> SEQUENCE: 13

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asn Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Leu Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Met Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Val Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Thr Glu Pro Pro Phe Gly Glu Ser Tyr Ile Val Ile Gly Ala Gly Glu
    370                 375                 380

Lys Ala Leu Lys Leu Ser Trp Phe Lys Lys Gly Ser Ser Ile Gly Lys
385                 390                 395                 400
```

```
Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Ala Phe Thr Ser Val
            420                 425                 430

Gly Lys Leu Val His Gln Val Phe Gly Thr Ala Tyr Gly Val Leu Phe
        435                 440                 445

Ser Gly Val Ser Trp Thr Met Lys Ile Gly Ile Gly Ile Leu Leu Thr
    450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Val Val Gln Ala
                485                 490                 495

<210> SEQ ID NO 14
<211> LENGTH: 192
<212> TYPE: PRT
<213> ORGANISM: Hepatitis C virus

<400> SEQUENCE: 14

Ala Glu Val Lys Asn Ile Ser Thr Gly Tyr Met Val Thr Asn Asp Cys
1               5                   10                  15

Thr Asn Asp Ser Ile Thr Trp Gln Leu Gln Ala Ala Val Leu His Val
            20                  25                  30

Pro Gly Cys Val Pro Cys Glu Lys Val Gly Asn Thr Ser Arg Cys Trp
        35                  40                  45

Ile Pro Val Ser Pro Asn Val Ala Val Gln Gln Pro Gly Ala Leu Thr
    50                  55                  60

Gln Gly Leu Arg Thr His Ile Asp Met Val Val Met Ser Ala Thr Leu
65                  70                  75                  80

Cys Ser Ala Leu Tyr Val Gly Asp Leu Cys Gly Gly Val Met Leu Ala
                85                  90                  95

Ala Gln Met Phe Ile Val Ser Pro Gln His His Trp Phe Val Gln Asp
            100                 105                 110

Cys Asn Cys Ser Ile Tyr Pro Gly Thr Ile Thr Gly His Arg Met Ala
        115                 120                 125

Trp Asp Met Met Met Asn Trp Ser Pro Thr Ala Thr Met Ile Leu Ala
    130                 135                 140

Tyr Ala Met Arg Val Pro Glu Val Ile Ile Asp Ile Ile Gly Gly Ala
145                 150                 155                 160

His Trp Gly Val Met Phe Gly Leu Ala Tyr Phe Ser Met Gln Gly Ala
                165                 170                 175

Trp Ala Lys Val Val Val Ile Leu Leu Leu Ala Ala Gly Val Asp Ala
            180                 185                 190

<210> SEQ ID NO 15
<211> LENGTH: 478
<212> TYPE: PRT
<213> ORGANISM: Human immunodeficiency virus type 1

<400> SEQUENCE: 15

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45
```

```
Gln Glu Val Val Leu Val Asn Val Thr Glu Asn Phe Asn Met Trp Lys
    50              55                  60

Asn Asp Met Val Glu Gln Met His Glu Asp Ile Ile Ser Leu Trp Asp
65              70                  75                  80

Gln Ser Leu Lys Pro Cys Val Lys Leu Thr Pro Leu Cys Val Ser Leu
                85                  90                  95

Lys Cys Thr Asp Leu Lys Asn Asp Thr Asn Thr Asn Ser Ser Ser Gly
                100                 105                 110

Arg Met Ile Met Glu Lys Gly Glu Ile Lys Asn Cys Ser Phe Asn Ile
            115                 120                 125

Ser Thr Ser Ile Arg Gly Lys Val Gln Lys Glu Tyr Ala Phe Phe Tyr
    130                 135                 140

Lys Leu Asp Ile Ile Pro Ile Asp Asn Asp Thr Thr Ser Tyr Lys Leu
145                 150                 155                 160

Thr Ser Cys Asn Thr Ser Val Ile Thr Gln Ala Cys Pro Lys Val Ser
                165                 170                 175

Phe Glu Pro Ile Pro Ile His Tyr Cys Ala Pro Ala Gly Phe Ala Ile
                180                 185                 190

Leu Lys Cys Asn Asn Lys Thr Phe Asn Gly Thr Gly Pro Cys Thr Asn
                195                 200                 205

Val Ser Thr Val Gln Cys Thr His Gly Ile Arg Pro Val Val Ser Thr
    210                 215                 220

Gln Leu Leu Leu Asn Gly Ser Leu Ala Glu Glu Val Val Ile Arg
225                 230                 235                 240

Ser Val Asn Phe Thr Asp Asn Ala Lys Thr Ile Ile Val Gln Leu Asn
                245                 250                 255

Thr Ser Val Glu Ile Asn Cys Thr Arg Pro Asn Asn Asn Thr Arg Lys
                260                 265                 270

Arg Ile Arg Ile Gln Arg Gly Pro Gly Arg Ala Phe Val Thr Ile Gly
            275                 280                 285

Lys Ile Gly Asn Met Arg Gln Ala His Cys Asn Ile Ser Arg Ala Lys
    290                 295                 300

Trp Asn Asn Thr Leu Lys Gln Ile Ala Ser Lys Leu Arg Glu Gln Phe
305                 310                 315                 320

Gly Asn Asn Lys Thr Ile Ile Phe Lys Gln Ser Ser Gly Gly Asp Pro
                325                 330                 335

Glu Ile Val Thr His Ser Phe Asn Cys Gly Gly Glu Phe Phe Tyr Cys
                340                 345                 350

Asn Ser Thr Gln Leu Phe Asn Ser Thr Trp Phe Asn Ser Thr Trp Ser
            355                 360                 365

Thr Glu Gly Ser Asn Asn Thr Glu Gly Ser Asp Thr Ile Thr Leu Pro
    370                 375                 380

Cys Arg Ile Lys Gln Ile Ile Asn Met Trp Gln Lys Val Gly Lys Ala
385                 390                 395                 400

Met Tyr Ala Pro Pro Ile Ser Gly Gln Ile Arg Cys Ser Ser Asn Ile
                405                 410                 415

Thr Gly Leu Leu Leu Thr Arg Asp Gly Gly Asn Ser Asn Asn Glu Ser
                420                 425                 430

Glu Ile Phe Arg Pro Gly Gly Gly Asp Met Arg Asp Asn Trp Arg Ser
            435                 440                 445

Glu Leu Tyr Lys Tyr Lys Val Val Lys Ile Glu Pro Leu Gly Val Ala
    450                 455                 460
```

Pro Thr Lys Ala Lys Arg Arg Val Val Gln Arg Glu Lys Arg
465                 470                 475

<210> SEQ ID NO 16
<211> LENGTH: 565
<212> TYPE: PRT
<213> ORGANISM: Influenza A virus

<400> SEQUENCE: 16

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asn Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

-continued

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 17
<211> LENGTH: 566
<212> TYPE: PRT
<213> ORGANISM: Influenza A virus

<400> SEQUENCE: 17

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro

```
                165                 170                 175
Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
            210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
                290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
                370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
                450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Val Ala Ser Ser Leu Val Leu Val
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 18
```

```
<211> LENGTH: 565
<212> TYPE: PRT
<213> ORGANISM: Influenza A virus

<400> SEQUENCE: 18
```

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser

```
            385                 390                 395                 400
Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg
                565

<210> SEQ ID NO 19
<211> LENGTH: 566
<212> TYPE: PRT
<213> ORGANISM: Influenza A virus

<400> SEQUENCE: 19

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
        130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
                180                 185                 190
```

```
Leu Tyr Ile Trp Gly Val His His Pro Gly Thr Asp Asn Asp Gln Ile
            195                 200                 205

Phe Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Ile Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
            450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 20
<211> LENGTH: 7
<212> TYPE: PRT
<213> ORGANISM: Artificial Sequence
<220> FEATURE:
<223> OTHER INFORMATION: Synthetic Polypeptide
```

-continued

<400> SEQUENCE: 20

```
Arg Arg Arg Lys Lys Arg Gly
1               5
```

METHODS AND COMPOSITIONS FOR IMMUNIZATION AGAINST VIRUS

CROSS-REFERENCE TO RELATED APPLICATIONS

This application claims priority of U.S. provisional patent application Ser. No. 61/164,385, titled "METHODS AND COMPOSITIONS FOR IMMUNIZATION AGAINST INFLUENZA" filed Mar. 27, 2009, U.S. provisional patent application Ser. No. 61/164,387, titled "METHODS AND COMPOSITIONS FOR IMMUNIZATION AGAINST HUMAN IMMUNODEFICIENCY VIRUS" filed Mar. 28, 2009, U.S. provisional patent application Ser. No. 61/164,388, titled "METHODS AND COMPOSITIONS FOR IMMUNIZATION AGAINST FLAVIVIRUS" filed Mar. 28, 2009, U.S. provisional patent application Ser. No. 61/164,389, titled "METHODS FOR MANUFACTURING VACCINES AGAINST VIRAL INFECTION" filed Mar. 28, 2009, U.S. provisional patent application Ser. No. 61/313,676, titled "METHODS AND COMPOSITIONS FOR IMMUNIZATION AGAINST INFLUENZA" filed Mar. 12, 2010, the contents of all of which are incorporated herein in their entirety by reference.

REFERENCE TO A SEQUENCE LISTING

This application includes a Sequence Listing. A computer readable copy of the Sequence Listing was submitted by EFS Web on Jul. 17, 2014 as an ASCII file created on Jul. 17, 2014, named SEQ_LIST_14182296_ST25, which is 62,676 bytes in size. The information contained in the Sequence Listing is herein incorporated by reference in its entirety.

TECHNICAL FIELD OF THE INVENTION

The invention generally relates to partially glycosylated viral polypeptides that are useful for generating potent, broadly-reactive immunogenic compositions effective against the virus. In particular, the invention relates to vaccines generated using monoglycosylated influenza virus hemagglutinin (HA) peptide, the vaccines exhibiting potent activity against influenza viruses. The invention relates to pharmaceutical compositions comprising the glycoproteins and vaccines generated therefrom, and to methods of using the deglycosylated HA polypeptides for prophylaxis and treatment of influenza virus infections.

BACKGROUND OF THE INVENTION

In eukaryotes, sugar residues are commonly linked to four different amino acid residues. These amino acid residues are classified as O-linked (serine, threonine, and hydroxylysine) and N-linked (asparagine). The O-linked sugars are synthesized in the Golgi or rough Endoplasmic Reticulum (ER) from nucleotide sugars. The N-linked sugars are synthesized from a common precursor, and subsequently processed. It is known that addition of N-linked carbohydrate chains is important for stabilization of folding, prevention of degradation in the endoplasmic reticulum, oligomerization, biological activity, and transport of glycoproteins. The addition of N-linked oligosaccharides to specific Asn residues plays an important role in regulating the activity, stability or antigenicity of mature proteins of viruses (Opdenakker G. et al *FASEB Journal* 7, 1330-1337 1993). It has also been suggested that N-linked glycosylation is required for folding, transport, cell surface expression, secretion of glycoproteins (Helenius, A., *Molecular Biology of the Cell* 5, 253-265 1994), protection from proteolytic degradation and enhancement of glycoprotein solubility (Doms et al., Virology 193, 545-562 1993). Viral surface glycoproteins are not only required for correct protein folding, but also provide protection against neutralizing antibodies as a "glycan shield." As a result, strong host-specific selection is frequently associated with codon positions of potential N-linked glycosylation. Consequently N-linked glycosylation sites tend to be conserved across strains and clades.

There are three main types of influenza virus: A, B and C. Type A strains of influenza virus can cause severe illness and are the only type to have caused human pandemics. The H5N1 strain is a type A influenza virus. Type B strains cause sporadic human cases and small-scale outbreaks. Type C strains only rarely cause human infection and have not caused large outbreaks. Of the influenza A viruses, only subtypes H1, H2 and H3 have been transmitted easily between humans.

Outbreaks of influenza A virus continue to cause widespread morbidity and mortality worldwide. In the United States alone, an estimated 5 to 20% of the population is infected by influenza A virus annually, causing approximately 200,000 hospitalizations and 36,000 deaths. The establishment of comprehensive vaccination policies has been an effective measure to limit influenza morbidity. However, the frequent genetic drifting of the virus requires yearly reformulation of the vaccine, potentially leading to a mismatch between the viral strain present in the vaccine and that circulating. Thus, antiviral therapies against influenza virus are important tools to limit both disease severity as well as transmission.

The highly pathogenic H5N1 influenza viruses have caused outbreaks in poultry and wild birds since 2003 (Li K S et al. (2004) Nature 430:209-213). As of February 2010, these viruses have infected not only avian species but also over 478 humans, of which 286 cases proved to be fatal (who.int/csr/disease/avian_influenza/country/cases_table_2010_02_17/en/index.html). The highly pathogenic H5N1 and the 2009 swine-origin influenza A (H1N1) viruses have caused global outbreaks and raised a great concern that further changes in the viruses may occur to bring about a deadly pandemic (Garten R J, et al (2009) Science 325:197-201, Neumann G, et al. (2009) Nature 459:931-939). There is great concern that an influenza virus would acquire the ability to spread efficiently between humans, thereby becoming a pandemic threat. An influenza vaccine must, therefore, be an integral part of any pandemic preparedness plan.

Influenza viruses are segmented negative-strand RNA viruses and belong to the Orthomyxoviridae family. Influenza A virus consists of 9 structural proteins and codes additionally for one nonstructural NS1 protein with regulatory functions. The non-structural NS1 protein is synthesized in large quantities during the reproduction cycle and is localized in the cytosol and nucleus of the infected cells. The segmented nature of the viral genome allows the mechanism of genetic reassortment (exchange of genome segments) to take place during mixed infection of a cell with different viral strains. The influenza A virus may be further classified into various subtypes depending on the different hemagglutinin (HA) and neuraminidase (NA) viral proteins displayed on their surface. Influenza A virus subtypes are identified by two viral surface glycoproteins, hemagglutinin (HA or H) and neuraminidase (NA or N). Each influenza virus subtype is identified by its combination of H and N proteins. There are 16 known HA subtypes and 9 known NA subtypes. Influenza type A viruses can infect people, birds, pigs, horses, and other animals, but wild birds are the natural hosts for these viruses. Only some influenza A subtypes (i.e., H1N1, H1N2, and H3N2) are currently in circulation among people, but all combinations of the 16H and 9 NA subtypes have been identified in avian species, especially in wild waterfowl and shorebirds. In addition, there is increasing evidence that H5 and H7 influenza viruses can also cause human illness.

The HA of influenza A virus comprises two structurally distinct regions, namely, a globular head region and a stem region. The globular head region contains a receptor binding site which is responsible for virus attachment to a target cell and participates in the hemagglutination activity of HA. The stem region contains a fusion peptide which is necessary for membrane fusion between the viral envelope and an endosomal membrane of the cell and thus relates to fusion activity (Wiley et al., Ann. Rev. Biochem., 56:365-394 (1987)).

Important contributions to the understanding of influenza infections have come from the studies on hemagglutinin (HA), a viral coat glycoprotein that binds to specific sialylated glycan receptors in the respiratory tract, allowing the virus to enter the cell (Kuiken T, et al. (2006) Science 312:394-397; Maines T R, et al. (2009) Science 325:484-487; Skehel J J, Wiley DC (2000) Ann Rev Biochem 69:531-569; van Riel D, et al (2006) Science 312:399-399). To cross the species barrier and infect the human population, avian HA must change its receptor-binding preference from a terminally sialylated glycan that contains α2,3 (avian)-linked to α2,6 (human)-linked sialic acid motifs (Connor R J, et al. (1994) Virology 205:17-23), and this switch could occur through only two mutations, as in the 1918 pandemic (Tumpey T M, et al (2007) Science 315:655-659). Therefore, understanding the factors that affect influenza binding to glycan receptors is critical for developing methods to control any future crossover influenza strains that have pandemic potential.

To address the need for making a candidate influenza vaccine that could induce potent neutralizing antibodies against divergent strains of H5N1 influenza viruses a consensus H5N1 hemagglutinin (HA) sequence based vaccine elicited antibodies that neutralized a panel of virions that have been pseudotyped with the HA from various H5N1 clades. (Chen M W, et al. (2008) Proc Natl Acad Sci USA 105:13538-13543).

HA is a homotrimeric transmembrane protein with an ectodomain composed of a globular head and a stem region (Kuiken T, et al. (2006) Science 312:394-397). Both regions carry N-linked oligosaccharides (Keil W, et al. (1985) EMBO J 4:2711-2720), which affect the functional properties of HA (Chen Z Y, et al. (2008) Vaccine 26:361-371; Ohuchi R, et al. (1997) J Virol 71:3719-3725). Among different subtypes of influenza A viruses, there is extensive variation in the glycosylation sites of the head region, whereas the stem oligosaccharides are more conserved and required for fusion activity (Ohuchi R, et al. (1997) J Virol 71:3719-3725). Glycans near antigenic peptide epitopes interfere with antibody recognition (Skehel J J, et al. (1984) Proc Natl Acad Sci USA 81:1779-1783), and glycans near the proteolytic activation site of HA modulate cleavage and influence the infectivity of influenza virus (Deshpande K L, et al. (1987) Proc Natl Acad Sci USA 84:36-40). Mutational deletion of HA glycosylation sites can affect viral receptor binding (Gunther I, et al. (1993) Virus Res 27:147-160).

Changes in the peptide sequence at or near glycosylation sites may alter HA's 3D structure, and thus receptor-binding specificity and affinity. Indeed, HAs from different H5N1 subtypes have different glycan-binding patterns (Stevens J, et al. (2008) J Mol Biol 381:1382-1394). Mutagenesis of glycosylation sites on H1 and H3 has been studied in the whole-viral system (Chandrasekaran A, et al. (2008) Nat Biotechnol 26:107-113; Deom C M, et al. (1986) Proc Natl Acad Sci USA 83:3771-3775). However, it is not known how changes in glycosylation affect receptor-binding specificity and affinity, especially with regard to the most pathogenic H5N1 HA.

Flu vaccines, when made, have to be changed every year as the less highly glycosylated or non-glycosylated regions of hemagglutinin continue to mutate to escape from the host immune system.

The goal of vaccine design against heterogeneous pathogens is to identify and design effective and broadly protective antigens. In the case of influenza, considerable historical efforts have gone into the empirical testing of conserved linear sequences and regions with little success. A plausible reason for these failures is a lack of knowledge that focused responses against antigenic test articles are actual bona fide productive sites for neutralization of an antigen on the pathogen in the setting of an actual infection.

SUMMARY OF THE INVENTION

Specifically, there is a need for cross neutralizing monoclonal antibodies that can be used in the design and validation of vaccine production processes that maintain or enhance the quality and antigenicity of cross neutralizing epitopes in current and future manufactured vaccines. Assuming that antibody binding to vaccine is reflective of structural integrity and antigenic potential, one would assess binding of cross neutralizing antibodies, such as deglycosylated HA polypeptides to such vaccine process derivatives to quantitatively assess their cross neutralizing potential. To maximize the responses toward these universal epitopes one would create derivatives to increase immunogenicity towards these universal epitopes.

According to the invention, a vaccine using these principles is disclosed. The antigen is generated by partially removing sugars from the viral glycoprotein to expose the glycosylation sites (which are highly conserved and do not mutate or do not mutate aggressively) and at the same time retain adequate sugars to preserve the tertiary structure of the glycoprotein. The partially glycosylated viral glycoproteins are generated by partially deglycosylating the glycoproteins such that a particular glycosylation site retains one, two or three sugar units. In some aspects the partially glycosylated glycoprotein can be generated by providing a protein or polypeptide unglycosylated at one or more particular glycosylation sites and conjugating a mono-, di- or tri-saccharide to the glycosylation sites.

A vaccine is disclosed comprising at least one partially glycosylated HA, NA or M2 glycoprotein and a pharmaceutically acceptable carrier. In some implementations, the partially glycosylated HA glycoprotein is selected from the group consisting of partially glycosylated influenza virus HI, H3, and H5. In some implementations, the partially glycosylated HA glycoprotein is glycosylated at asparagine residues at one or more of positions 39, 127, 170, 181, 302, 495 and 500 of H5 HA. In some implementations, the asparagine residue is at position 177.

A method is disclosed comprising administering to a subject susceptible of influenza a vaccine comprising at least one deglycosylated HA glycoprotein and a pharmaceutically acceptable carrier. In some implementations, the deglycosylated HA glycoprotein is selected from the group consisting of HI, H3, and H5.

In some implementations the deglycosylation leaves a monoglycosylation (one sugar remaining) at one or more glycosylation site on the glycoprotein. In some implementations the deglycosylation leaves a diglycosylation (2 sugars remaining) at at least one glycosylation site on the glycoprotein. In some implementations the deglycosylation leaves a triglycosylation (3 sugars remaining) at one or more glycosylation site on the glycoprotein. In some implementations the deglycosylation leaves at least one of a monoglycosylation, a diglycosylation and a triglycosylation at at least one glycosylation site on the glycoprotein.

The invention relates to an immunogenic composition for raising an immune response to a pathogen of viral, bacterial, fungal or other origin, the composition comprising: an antigen glycoprotein from the pathogen of viral, bacterial, fungal or other origin, wherein the glycoprotein is partially glycosylated.

In some aspects, the pathogen is a virus and the partially glycosylated antigen is a virus, a virus-like particle, a viral peptide, a protein, a polypeptide, or a fragment thereof derived from the virus, or a fusion protein partially comprising a virus protein sequence.

The virus is selected from influenza virus, respiratory syncytial virus (RSV), chlamydia, adenovirdiae, mastadenovirus, aviadenovirus, herpesviridae, herpes simplex virus 1, herpes simplex virus 2, herpes simplex virus 5, herpes simplex virus 6, leviviridae, levivirus, enterobacteria phase MS2, allolevirus, poxviridae, chordopoxvirinae, parapoxvirus, avipoxvirus, capripoxvirus, leporiipoxvirus, suipoxvirus, molluscipoxvirus, entomopoxvirinae, papovaviridae, polyomavirus, papillomavirus, paramyxoviridae, paramyxovirus, parainfluenza virus 1, mobillivirus, measles virus, rubulavirus, mumps virus, pneumonovirinae, pneumovirus, metapneumovirus, avian pneumovirus, human metapneumovirus, picornaviridae, enterovirus, rhinovirus, hepatovirus, human hepatitis A virus, cardiovirus, andapthovirus, reoviridae, orthoreovirus, orbivirus, rotavirus, cypovirus, fijivirus, phytoreovirus, oryzavirus, retroviridae, mammalian type B retroviruses, mammalian type C retroviruses, avian type C retroviruses, type D retrovirus group, BLV-HTLV retroviruses, lentivirus, human immunodeficiency virus 1, human immunodeficiency virus 2, HTLV-I and -II viruses, SARS coronavirus, herpes simplex virus, Epstein Barr virus, cytomegalovirus, hepatitis virus (HCV, HAV, HBV, HDV, HEV), *toxoplasma gondii* virus, *treponema pallidium* virus, human T-lymphotrophic virus, encephalitis virus, West Nile virus, Dengue virus, Varicella Zoster Virus, rubeola, mumps, rubella, spumavirus, flaviviridae, hepatitis C virus, hepadnaviridae, hepatitis B virus, togaviridae, alphavirus sindbis virus, rubivirus, rubella virus, rhabdoviridae, vesiculovirus, lyssavirus, ephemerovirus, cytorhabdovirus, necleorhabdovirus, arenaviridae, arenavirus, lymphocytic choriomeningitis virus, Ippy virus, lassa virus, coronaviridae, coronavirus and torovirus.

The viral peptide, protein, polypeptide, or a fragment thereof is selected from influenza virus neuraminidase, influenza virus hemagglutinin, human respiratory syncytial virus (RSV)-viral proteins, RSV F glycoprotein, RSV G glycoprotein, herpes simplex virus (HSV) viral proteins, herpes simplex virus glycoproteins gB, gC, gD, and gE, chlamydia MOMP and PorB antigens, core protein, matrix protein or other protein of Dengue virus, measles virus hemagglutinin, herpes simplex virus type 2 glycoprotein gB, poliovirus 1 VP1, envelope glycoproteins of HIV 1, hepatitis B surface antigen, diptheria toxin, streptococcus 24M epitope, gonococcal pilin, pseudorabies virus g50 (gpD), pseudorabies virus II (gpB), pseudorabies virus III (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulinahydodysenteriae protective antigen, bovine viral diarrhea glycoprotein 55, Newcastle disease virus hemagglutinin-neuraminidase, swine flu hemagglutinin, swine flu neuraminidase, foot and mouth disease virus, hog colera virus, swine influenza virus, African swine fever virus, *Mycoplasma liyopneutiioniae*, infectious bovine rhinotracheitis virus, infectious bovine rhinotracheitis virus glycoprotein E, glycoprotein G, infectious laryngotracheitis virus, infectious laryngotracheitis virus glycoprotein G or glycoprotein I, a glycoprotein of La Crosse virus, neonatal calf diarrhoea virus, Venezuelan equine encephalomyelitis virus, punta toro virus, murine leukemia virus, mouse mammary tumor virus, hepatitis B virus core protein and hepatitis B virus surface antigen or a fragment or derivative thereof, antigen of equine influenza virus or equine herpes virus, including equine influenza virus type A/Alaska 91 neuraminidase, equine influenza virus typeA/Miami 63 neuraminidase, equine influenza virus type A/Kentucky 81 neuraminidase equine herpes virus type 1 glycoprotein B, and equine herpes virus type 1 glycoprotein D, antigen of bovine respiratory syncytial virus or bovine parainfluenza virus, bovine respiratory syncytial virus attachment protein (BRSV G), bovine respiratory syncytial virus fusion protein (BRSV F), bovine respiratory syncytial virus nucleocapsid protein (BRSVN), bovine parainfluenza virus type 3 fusion protein, bovine parainfluenza virus type 3 hemagglutinin neuraminidase, bovine viral diarrhoea virus glycoprotein 48 and glycoprotein 53, glycoprotein E of Dengue virus and glycoprotein E1E2 of human hepatitis C virus.

In some aspects, the deglycosylated viral antigen is a mono-, di-, or tri-glycosylated influenza virus hemagglutinin. In some embodiments, the deglycosylated viral antigen is a mono-glycosylated hemagglutinin selected from the group consisting of influenza virus HI, H3, and H5. In some embodiments, the mono-glycosylated influenza virus hemagglutinin comprises an N-glycosylation site comprising an amino acid sequence of asparagine-$X_{aa}$-serine and asparagine-$X_{aa}$-threonine, where $X_{aa}$ is any amino acid except proline. In some aspects, the monoglycosylated hemagglutinin comprising a single GlcNAc sugar at a glycosylation site displays relaxed specificity but enhanced affinity towards HA-receptor binding.

In some embodiments, the deglycosylated viral antigen is an influenza virus hemagglutinin di- or tri-glycosylated with N-acetylglucosamine (GlcNAc) and/or mannose. In some aspects, the deglycosylated viral antigen is a mono-glycosylated influenza virus hemagglutinin glycosylated with N-acetylglucosamine (GlcNAc).

In some aspects, the mono-glycosylated influenza virus hemagglutinin comprises a polypeptide comprising a consensus H5 HA sequence (SEQ ID NO: 4). In some embodiments, the mono-glycosylated consensus H5 HA sequence (SEQ ID NO: 4) is glycosylated at asparagine residues at one or more of positions 39, 170, 181, 302 and 495. In other aspects, the mono-glycosylated influenza virus hemagglutinin comprises a H1 polypeptide sequence selected from the group consisting of a NIBRG-121 (Pandemic 2009 A(H1N1) vaccine strain) sequence (SEQ ID NO: 6), a consensus H1-A (SEQ ID NO: 8) and a consensus H1-C (SEQ ID NO: 10) sequence. In some embodiments, the HA sequence is modified to enable expression in a suitable eukaryotic cell.

In one embodiment, the mono-glycosylated influenza virus hemagglutinin comprises a seasonal H1 (Brisbane) polypeptide.

The invention also relates to a vaccine comprising an immunogenic polypeptide comprising a viral glycoprotein deglycosylated to a state of mono-, di-, or tri-glycosylation and optionally, an adjuvant, wherein the vaccine is capable of eliciting an immune response against a respiratory virus. In some embodiments, the respiratory virus is an influenza virus and the viral glycoprotein is hemagglutinin (HA).

In some aspects, the influenza virus is selected from the group consisting of an avian influenza virus and a seasonal influenza virus. In some embodiments, the avian influenza virus is H5N1. In some embodiments, the influenza virus is influenza A virus.

In one aspect, the virus is respiratory syncytial virus (RSV), and the partially glycosylated viral antigen is a mono-, di-, or tri-glycosylated RSV F (fusion), G (attachment) of SH (small hydrophobic) glycoprotein, or immunogenic fragments thereof. In some embodiments, the mono-glycosylated RSV G protein sequence (SEQ ID NO: 12) is partially glycosylated at asparagine residues at one or more potential N-glycosylation sites indicated in Table 6.

In one aspect, the virus is a flavivirus, and the partially glycosylated viral antigen is a mono-, di-, or tri-glycosylated Dengue virus envelope glycoprotein M, glycoprotein E, or immunogenic fragments thereof. In some embodiments, the mono-glycosylated Dengue virus envelope glycoprotein E (SEQ ID NO: 13) is partially glycosylated at asparagine residues at one or more N-glycosylation sites N67 and N153 indicated in Table 7.

In one aspect, the virus is a hepatitis C virus, and the partially glycosylated viral antigen is a mono-, di-, or tri-glycosylated hepatitis C envelope glycoprotein E1, glycoprotein E2, or immunogenic fragments thereof. In some embodiments, the mono-glycosylated hepatitis C envelope glycoprotein E1 (SEQ ID NO: 14) is partially glycosylated at asparagine residues at one or more N-glycosylation sites N196, N209, N234, N305, AND N325 indicated in Table 8.

In one aspect, wherein the virus is a human immunodeficiency virus (HIV), and the partially glycosylated viral antigen is a mono-, di-, or tri-glycosylated HIV envelope glycoprotein gp120, transmembrane glycoprotein gp41, or immunogenic fragments thereof. In some embodiments, the mono-glycosylated HIV envelope glycoprotein gp120 (SEQ ID NO: 15) is partially glycosylated at asparagine residues at one or more potential N-glycosylation sites indicated in Table 9.

The invention also relates to a vaccine composition comprising: an influenza HA polypeptide, wherein the influenza HA polypeptide is deglycosylated to a state of monoglycosylation; and a pharmaceutically acceptable carrier, wherein upon introduction of the mono-glycosylated HA polypeptide into a subject, the polypeptide induces the subject to produce antibodies that bind to influenza virus.

In some aspects, introduction of the mono-glycosylated HA polypeptide into the subject, induces the subject to produce antibodies that neutralize both seasonal and avian influenza virus.

In one embodiment, the mono-glycosylated influenza virus hemagglutinin comprises a seasonal H1 (Brisbane) HA polypeptide and upon introduction of the mono-glycosylated HA polypeptide into a subject, the H1 (Brisbane) HA polypeptide induces the subject to produce antibodies that neutralize NIBRG-121 (Pandemic 2009 A(H1N1) vaccine strain) influenza virus.

In another embodiment, the mono-glycosylated influenza virus hemagglutinin comprises a NIBRG-121 (Pandemic 2009 A(H1N1) vaccine strain) polypeptide and upon introduction of the mono-glycosylated HA polypeptide into a subject, the NIBRG-121 (Pandemic 2009 A(H1N1) vaccine strain) polypeptide induces the subject to produce antibodies that neutralize seasonal H1 (Brisbane) HA influenza virus.

In some aspects, the vaccine further comprises an adjuvant, which can be selected from aluminum hydroxide, aluminum phosphate, both aluminum hydroxide and aluminum phosphate, incomplete Freund's adjuvant (IFA), squalene, squalane, alum, and MF59.

The invention relates to methods for immunizing a mammal against a viral respiratory infection, the method comprising: administering to the mammal susceptible to infection by the respiratory virus a vaccine comprising an immunogenic polypeptide comprising a viral glycoprotein deglycosylated to a state of mono-, di-, or tri-glycosylation, wherein the vaccine is capable of eliciting an immune response against the respiratory virus. In some embodiments, the respiratory virus is an influenza virus and the viral glycoprotein is hemagglutinin (HA). The vaccine may be administered through parenteral administration, inhalation means, intranasally, and sometimes prophylactically.

In some aspects, the vaccine elicits immune response against influenza virus strains that are different from the influenza virus strain from which the deglycosylated viral glycoprotein is selected. In some embodiments, the deglycosylated viral glycoprotein is a mono-glycosylated influenza hemagglutinin (HA).

The present invention provides vaccines effective against influenza A virus. In one embodiment, the vaccine comprises a peptide or polypeptide functionally mimicking a neutralization epitope of a molecule described herein. In another embodiment, the vaccine is effective against a viral antigen comprises a peptide or polypeptide functionally mimicking a neutralization epitope of a molecule described herein. In one embodiment, the viral antigen is from an influenza virus or an HIV-1 or HIV-2 virus, or a flavivirus, such as Dengue virus or hepatitis C virus.

In another embodiment, the vaccine is a vaccine effective against influenza A virus, comprising a peptide or polypeptide functionally mimicking a neutralization epitope of a molecule described herein. In one embodiment, the molecule is an antibody. In another embodiment, the antibody binds an HA antigen. In one other embodiment, the HA antigen is an H5 subtype. In one other embodiment, the HA antigen is an H1 subtype. In one other embodiment, the antigen is displayed on the surface of influenza A virus. In one other embodiment, the peptide or polypeptide comprises antigenic determinants that raise neutralizing antibodies.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 6, Panel A depicts SEQ ID NO: 20. Panel B: The purified HA proteins were analyzed by SDS/PAGE.Mindicates marker. Lane 1: $HA_{fg}$, the HA purified from 293E cells; lane 2: $HA_{ds}$, $HA_{fg}$ digested by NA; lane 3: $HA_{hm}$, the HA purified from 293S cells (Reeves P J, et al. (2002) Proc Natl Acad Sci USA 99:13419-13424); lane 4: $HA_{mg}$, $HA_{hm}$ digested by Endo H. Panel C: The HA-purified proteins were analyzed by gel-filtration chromatography. The eluted peak showed the $HA_{fg}$ trimer>200 kDa (red line), the $HA_{ds}$ trimer>200 kDa (black line), the $HA_{hm}$ trimer>200 kDa (blue line), and the $HA_{mg}$ trimer>180 kDa after gel filtration (green line). The figure presents superimposed elution profiles of HA proteins overlaid with protein marker (dashed line).

FIG. 9 shows assignments of major molecular ions observed in MALDI spectra of permethylated N-glycans from HA trimers. ND indicates not determined.

FIG. 10 shows the $\Delta\Delta G$ of HA glycosylated variants in response to α2,3 sialosides 1-15. Values represent $\Delta\Delta G$, kcal/mol. The entries in the leftmost column were obtained by subtraction of –G values of the latter HA from the former HA (e.g., $\Delta\Delta G$ ($HA_{fg} \rightarrow HA_{ds}$)=AG($HA_{ds}$)–AG($HA_{fg}$)). ND indicates not determined.

FIG. 11 shows differences in binding free energy changes between different sialoside ligands in response to HA variants. Values represent $\Delta\Delta G$, kcal/mol. The entries in the leftmost column were obtained by subtraction of AG values of the latter HA from the former HA (e.g., $\Delta\Delta G$ (1→2)=AG(2)–AG(1). ND indicates not determined.

FIG. 14 shows that the protein structures of H5 and H1 are more similar to each other (root mean square deviation (RMSD) of 0.9 Å), than to H3 (root mean square deviation (RMSD) of 2.5 Å).

FIG. 15 shows inhibition of NIBRG-121 (Pandemic 2009 A(H1N1) vaccine strain) by antisera generated using mono-glycosylated H1 (Brisbane) HA as antigen. Panel A: inhibition of the ability of the NIBRG-121 (Pandemic 2009 A(H1N1) vaccine strain) virus to agglutinate red blood cells. Panel B: inhibition of the ability of the NIBRG-121 (Pandemic 2009 A(H1N1) vaccine strain) virus to infect MDCK cells. Panel C: protection of BALB/c mice from infection by NIBRG-121 (Pandemic 2009 A(H1N1) vaccine strain) influenza virus. The antisera used was mice immunized with Brisbane HA proteins (5 μg) and the virus used for challenge was NIBRG-121 (100×$LD_{50}$)

FIG. 18 shows the inhibition of WSN (H1N1) by antisera generated using mono-glycosylated H1 (Pandemic 2009 A(H1N1) vaccine strain; shown in figure as California/2009) HA as antigen. Panel A: inhibition of the ability of the WSN (H1N1) virus to agglutinate red blood cells. Panel B: inhibition of the ability of the WSN (H1N1) virus to infect MDCK cells.

DETAILED DESCRIPTION OF THE INVENTION

Figure 1:
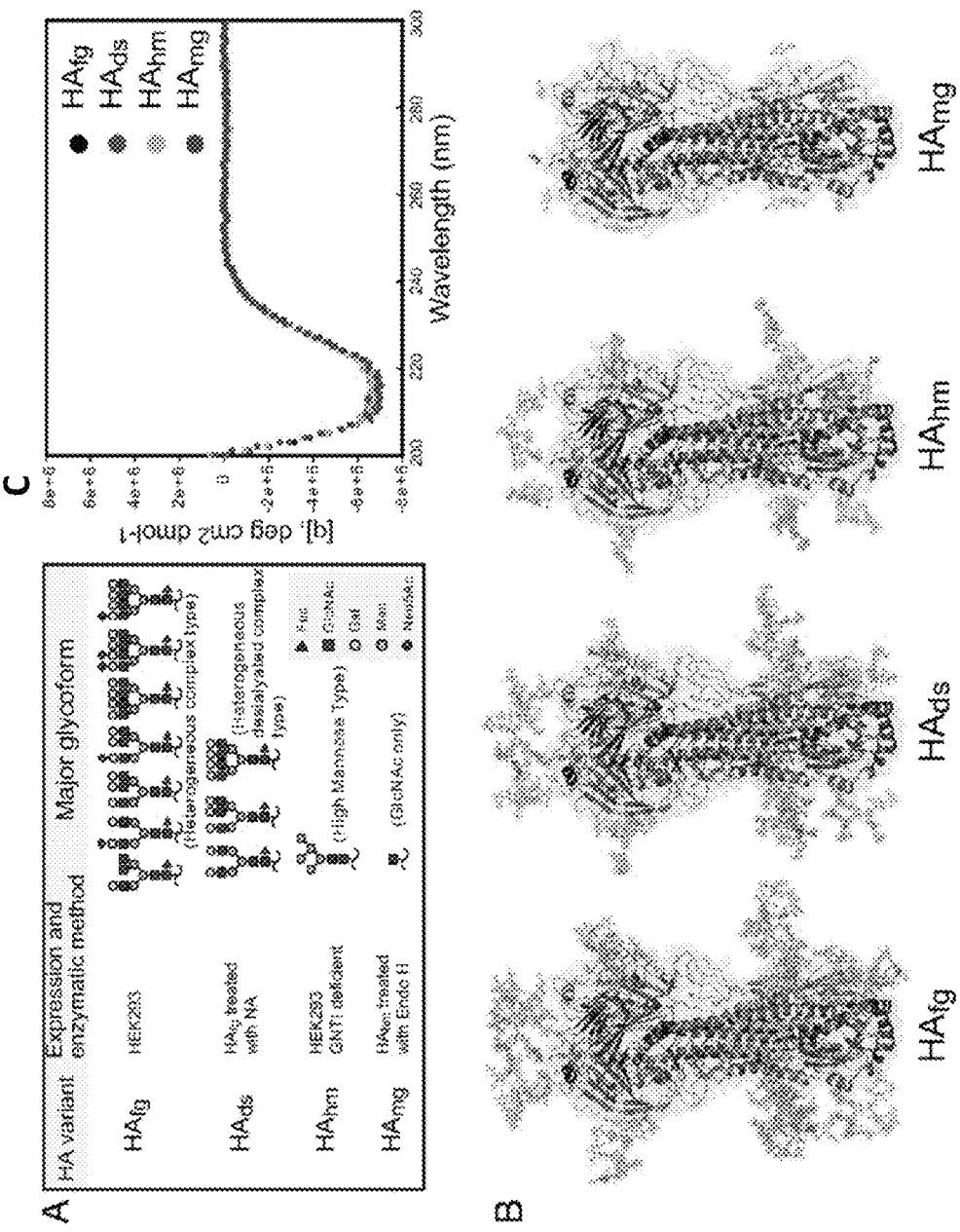
FIG. 1 shows schematic overviews and circular dichroism spectra of HAs with different glycosylations. Panel A, left: Four variants of HA proteins with different glycosylations: $HA_{fg}$, HA (a consensus sequence (Chen M W, et al. (2008) Proc Natl Acad Sci USA 105:13538-13543) expressed in HEK293E cells with the typical complex type N-glycans); $HA_{ds}$, NA-treated HA resulting in removal of sialic acids from $HA_{fg}$; $HA_{hm}$, HA expressed in GnTI-HEK293S cells with the high-mannose-type N-glycans; and $HA_{mg}$, Endo H-treated HA with GlcNAc only at its N-glycosylation sites. Panel A, right: Circular dichroism spectra of $HA_{fg}$, $HA_{ds}$, $HA_{hm}$, and $HA_{mg}$ demonstrate that the secondary structures of the four HA proteins with different glycosylations are similar. Panel B: Structure representation of $HA_{fg}$, $HA_{ds}$, $HA_{hm}$, and $HA_{mg}$ with different N-glycans attached at their N-glycosylation sites. The protein structures are created with Protein Data Bank ID code 2FK0 (Viet04 HA), colored in gray, and the N-linked glycans are displayed in green. All N-glycans are modeled by GlyProt (Bohne-Lang A, et al. (2005) Nucleic Acids Res 33:W214-W219), and the graphics are generated by PyMOL (pymol.org).

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

Hemagglutin (HA) of influenza virus is a homotrimeric transmembrane protein with an ectodomain composed of a globular head and a stem region. Both regions carry N-linked oligosaccharides, the biosynthesis of which follows the general pathways of N glycosylation. The functional properties of HA are affected by glycosylation at specific sites. The carbohydrates around the antigenic peptide epitopes interfere with the access of antibodies, and this effect may result in antigenic drift of influenza virus. Previous studies on HAs also revealed that the peptide sequences with glycosylation are highly conserved, and the HA receptor binding specificity was affected by the absence of a complex glycan chain near the receptor binding site. In addition, the proteolytic activation of HA was also modulated by the glycans near the cleavage site to influence the infectivity of influenza virus. The extensive variations in structure and number of glycosylation sites on the head region have been shown among different subtypes of the influenza A viruses, whereas the stem oligosaccharides were more conserved and required for fusion activity. All these findings have indicated the importance of HA glycosylation on its activity.

Viral transmission begins with a critical interaction between hemagglutinin (HA) glycoprotein, which is on the viral coat of influenza, and sialic acid (SA) containing glycans, which are on the host cell surface. To elucidate the role of HA glycosylation in this important interaction, various defined HA glycoforms were prepared, and their binding affinity and specificity were studied by using a synthetic SA microarray. Truncation of the N-glycan structures on HA increased SA binding affinities while decreasing specificity toward disparate SA ligands. The contribution of each monosaccharide and sulfate group within SA ligand structures to HA binding energy was quantitatively dissected. It was found that the sulfate group adds nearly 100-fold (2.04 kcal/mol) in binding energy to fully glycosylated HA, and so does the biantennary glycan to the monoglycosylated HA glycoform. Antibodies raised against HA protein bearing only a single N-linked GlcNAc at each glycosylation site showed better binding affinity and neutralization activity against influenza subtypes than the fully glycosylated HAs elicited. Thus, removal of structurally nonessential glycans on viral surface glycoproteins is a very effective and general approach for vaccine design against influenza and other human viruses.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "influenza A subtype" or "influenza A virus subtype" are used interchangeably, and refer to influenza A virus variants that are characterized by a hemagglutinin (H) viral surface protein, and thus are labeled by an H number, such as, for example, H1, H3, and H5. In addition, the subtypes may be further characterized by a neuraminidase (N) viral surface protein, indicated by an N number, such as, for example, N1 and N2. As such, a subtype may be referred to by both H and N numbers, such as, for example, H1N1, H5N1, and H5N2. The terms specifically include all strains (including extinct strains) within each subtype, which usually result from mutations and show different pathogenic profiles. Such strains will also be referred to as various "isolates" of a viral subtype, including all past, present and future isolates. Accordingly, in this context, the terms "strain" and "isolate" are used interchangeably. Subtypes contain antigens based upon an influenza A virus. The antigens may be based upon a hemagglutinin viral surface protein and can be designated as "HA antigen". In some instances, such antigens are based on the protein of a particular subtype, such as, for example, an H1 subtype and an H5 subtype, which may be designated an H1 antigen and an H5 antigen, respectively.

As used in the present disclosure, the term "deglycosylated" or "partially glycosylated" protein denotes a protein that has one or more sugars removed from the glycan structure of a fully glycosylated instance of the protein and in which the protein substantially retains its native conformation/folding. A "deglycosylated" protein includes a partially glycosylated protein in which the deglycosylation process leaves a monoglycosylation, a diglycosylation or a triglycosylation at one or more glycosylation sites present on the glycoprotein.

A "partially glycosylated" protein includes a "deglycosylated" protein in which one or more sugars are retained at each glycosylation site, and each partial glycosylation site contains a smaller glycan structure (containing fewer sugar units) as compared to the site in a fully glycosylated instance of the glycoprotein, and the partially glycosylated protein substantially retains its native conformation/folding. A "partially glycosylated" protein is generated by partial deglycosylation of the glycan structure of at least one glycosylation site of a fully glycosylated instance of the glycoprotein. A "partially glycosylated" protein also is generated by introducing glycosylation at an unglycosylated site of a protein such that the added glycosylation sequence is smaller than the glycan structure at that site in a fully glycosylated instance of the glycoprotein. A "partially glycosylated" protein also is generated by synthesizing a viral glycoprotein sequence, or fragment thereof, introducing glycosylated amino acid units (e.g., GlcNAc-Arginine moieties) at glycosylation sites of the sequence, such that the added glycan structure is smaller than the glycan structure at that site in a fully glycosylated instance of the glycoprotein.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or HIV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support.

Glycosylation of polypeptides is typically either N-linked or O-linked. N-linked refers to the attachment of the carbohydrate moiety to the side chain of an asparagine residue. A "sequon" is a sequence of three consecutive amino acids in a protein that can serve as the attachment site to a polysaccharide (sugar) called an N-linked-Glycan. This is a polysaccharide linked to the protein via the nitrogen atom in the side chain of asparagine (Asn). A sequon is either Asn-$X_{aa}$-Ser or Asn-$X_{aa}$-Thr, where $X_{aa}$ is any amino acid except proline. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. While the sequon Asn-X-Ser/Thr is absolutely required for the attachment of N-linked oligosaccharides to a glycoprotein (Marshall R D, *Biochemical Society Sympo-* sia 40, 17-26 1974), its presence does not always result in glycosylation and some sequons in glycoproteins can remain unglycosylated. (Curling E M, et al., *Biochemical Journal* 272, 333-337 1990)

Glycan microarray is a powerful tool for investigating carbohydrate-protein interactions and provides a new platform for influenza virus subtyping (Blixt O, et al. (2004) Proc Natl Acad Sci USA 101:17033-17038; Chandrasekaran A, et al. (2008) Nat Biotechnol 26:107-113; Liang P H, et al. (2007) J Am Chem Soc 129:11177-11184; Stevens J, et al. (2008) J Mol Biol 381:1382-1394). They mimic the glycans on the cell surface to exhibit multivalent interactions with high affinity and specificity. Using this technology, characterization of the receptor specificity of various native and mutant HAs providing a new platform for differentiating influenza virus subtypes was performed.

Although a powerful method, understanding HA-glycan interactions by glycan array analysis has been complicated by two issues: First, HA binding specificity is affected by the spatial arrangement and composition of the arrayed glycans and the binding detection method used (Srinivasan A, et al. (2008) Proc Natl Acad Sci USA 105:2800-2805). Second, the changes in the peptide sequence at or near glycosylation sites may alter HA's 3D structure, and thus receptor-binding specificity and affinity. Indeed, HAs from different H5N1 subtypes have different glycan-binding patterns (Stevens J, et al. (2008) J Mol Biol 381:1382-1394). Mutagenesis of glycosylation sites on H1 and H3 has been studied in the whole-viral system (Chandrasekaran A, et al. (2008) Nat Biotechnol 26:107-113; Deom C M, et al. (1986) Proc Natl Acad Sci USA 83:3771-3775). However, it is not known how changes in glycosylation affect receptor-binding specificity and affinity, especially with regard to the most pathogenic H5N1 HA. To address these issues, a method of quantitative glycan microarray analysis was developed to surmount the limitations of traditional HA binding experiments.

Previous studies have used HA from insect cell expression (Chandrasekaran A, et al. (2008) Nat Biotechnol 26:107-113). However, glycosylation in insect cells differs from mammalian cells, with a marked difference being that complex type N-glycans terminating in galactose and sialic acid are not produced in insect cells.

HA Glycosylated Variants Expressed from Human Cells

To address how changes in glycosylation affect receptor-binding specificity and affinity in human cells, a glycan microarray comprising extensive structural analogs of the HA-binding ligand, and several defined glycoforms of HA were prepared by using the influenza H5N1 HA consensus sequence (Chen M W, et al. (2008) Proc Natl Acad Sci USA 105:13538-13543) for quantitative binding analysis.

The codons of CHA5 were optimized for expression by using human codons. As shown in Table 1, the original viral protease cleavage site PQRERRRKKRG (SEQ ID NO: 1) was mutated to PQRERG (SEQ ID NO: 2) in order to prevent proteins from the enzymatic cleavage to form HA1 and HA2. The transmembrane region (residues: 533-555) was replaced with the additional residue;

(SEQ ID NO: 3)
LV*PR*GSPGSGYIPEAPRDGQAYVRKDGEWVLLSTFLGHHHHHH at the C terminus of the HA construct, where the thrombin cleavage site is in italics, the bacteriophage T4 fibritin foldon trimerization sequence is underlined, and the His-tag is in bold (Stevens J. et al. (2006) Science 312:404-410).

TABLE 1

| Consensus H5 hemagglutinin sequence |
|---|
| Amino acid sequence of consensus H5 HA showing in bold: signal sequence; and underlined: trimerization sequence and His-tag. |
| MEKIVLLFAIVSLVKSDQICIGSHANNSTEQVDTIMEKNVTVTHAQDILE     50 |
| KTHNGKLCDLDGVKPLILRDCSVAGWLLGNPMCDEFINVPEWSYIVEKAN     100 |
| PANDLCYPGDFNDYEELKHLLSRINHFEKIQIIPKSSWSSHEASSGVSSA     150 |
| CPYQGKSSFFRNVVWLIKKNSTYPTIKRSYNNTNQEDLLVLWGIHHPNDA     200 |
| AEQTKLYQNPTTYISVGTSTLNQRLVPKIATRSKVNGQSGRMEFFWTILK     250 |
| PNDAINFESNGNFIAPEYAYKIVKKGDSTIMKSELEYGNCNTKCQTPMGA     300 |
| INSSMPFHNIHPLTIGECPKYVKSNRLVLATGLRNSPQRERGLFGAIAGF     350 |
| IEGGWQGMVDGWYGYHHSNEQGSGYAADKESTQKAIDGVTNKVNSIIDKM     400 |
| NTQFEAVGREFNNLERRIENLNKKMEDGFLDVWTYNAELLVLMENERTLD     450 |
| FHDSNVKNLYDKVRLQLRDNAKELGNGCFEFYHKCDNECMESVRNGTYDY     500 |
| PQYSEEARLKREEISGV<u>DIRSLVPRGSPGSGYIPEAPRDGQAYVRKDGEW</u>     550 |
| <u>VLLSTFLGH</u>HHHHH |
| (SEQ ID NO: 4) |
| Nucleotide sequence of consensus H5 HA |
|   1 ATGGAGAAGA TCGTGCTGCT GTTCGCCATC GTGAGCCTGG TGAAGAGCGA |
|  51 CCAGATCTGC ATCGGATCCC ACGCCAACAA CAGCACCGAG CAGGTGGACA |
| 101 CCATCATGGA GAAGAACGTG ACCGTGACCC ACGCCCAGGA CATCCTGGAG |
| 151 AAGACCCACA ACGGCAAGCT GTGCGACCTG GACGGCGTGA AGCCTCTGAT |

TABLE 1-continued

Consensus H5 hemagglutinin sequence

```
 201  CCTGAGAGAC TGCAGCGTGG CCGGCTGGCT GCTGGGCAAC CCTATGTGCG

251  ACGAGTTCAT CAACGTGCCT GAGTGGAGCT ACATCGTGGA GAAGGCCAAC

301  CCTGCCAACG ACCTGTGCTA CCCTGGCGAC TTCAACGACT ACGAGGAGCT

351  GAAGCACCTG CTGAGCAGAA TCAACCACTT CGAGAAGATC CAGATCATCC

401  CTAAGAGCAG CTGGAGCAGC CACGAGGCCA GCAGCGGCGT GAGCAGCGCC

451  TGCCCTTACC AGGGCAAGAG CAGCTTCTTC AGAAACGTGG TGTGGCTGAT

501  CAAGAAGAAC AGCACCTACC CTACCATCAA GAGAAGCTAC AACAACACCA

551  ACCAGGAGGA CCTGCTGGTG CTGTGGGGCA TCCACCACCC TAACGACGCC

601  GCCGAGCAGA CCAAGCTGTA CCAGAACCCT ACCACCTACA TCAGCGTGGG

651  CACCAGCACC CTGAACCAGA GACTGGTGCC TAAGATCGCC ACCAGAAGCA

701  AGGTGAACGG CCAGAGCGGC AGAATGGAGT TCTTCTGGAC CATCCTGAAG

751  CCTAACGACG CCATCAACTT CGAGAGCAAC GGCAACTTCA TCGCCCCTGA

801  GTACGCCTAC AAGATCGTGA AGAAGGGCGA CAGCACCATC ATGAAGAGCG

851  AGCTGGAGTA CGGCAACTGC AACACCAAGT GCCAGACCCC TATGGGCGCC

901  ATCAACGCA GCATGCCTTT CCACAACATC CACCCTCTGA CCATCGGCGA

951  GTGCCCTAAG TACGTGAAGA GCAACAGACT GGTGCTGGCC ACCGGCCTGA

1001  GAAACAGCCC TCAGAGAGAG AGAGGCCTGT TCGGCGCCAT CGCCGGCTTC

1051  ATCGAGGGCG GCTGGCAGGG CATGGTGGAC GGCTGGTACG GCTACCACCA

1101  CAGCAACGAG CAGGGCAGCG GCTACGCCGC CGACAAGGAG AGCACCCAGA

1151  AGGCCATCGA CGGCGTGACC AACAAGGTGA ACAGCATCAT CGACAAGATG

1201  AACACCCAGT TCGAGGCCGT GGGCAGAGAG TTCAACAACC TGGAGAGAAG

1251  AATCGAGAAC CTGAACAAGA AGATGGAGGA CGGCTTCCTG GACGTGTGGA

1301  CCTACAACGC CGAGCTGCTG GTGCTGATGG AGAACGAGAG AACCCTGGAC

1351  TTCCACGACA GCAACGTGAA GAACCTGTAC GACAAGGTGA GACTGCAGCT

1401  GAGAGACAAC GCCAAGGAGC TGGGCAACGG CTGCTTCGAG TTCTACCACA

1451  AGTGCGACAA CGAGTGCATG GAGAGCGTGA GAAACGGCAC CTACGACTAC

1501  CCTCAGTACA GCGAGGAGGC CAGACTGAAG AGAGAGGAGA TCAGCGGCGT

1551  GGATATCAGA TCTCTGGTGC AAGAGGATC TCCAGGATCT GGATACATCC

1601  CAGAGGCTCC AAGAGATGGA CAAGCTTACG TGAGAAAGGA CGGAGAGTGG

1651  GTGCTGCTGT CTACTTTCCT GGGACACCAC CACCACCACC ACTAA
```
(SEQ ID NO: 5)

Figure 6:
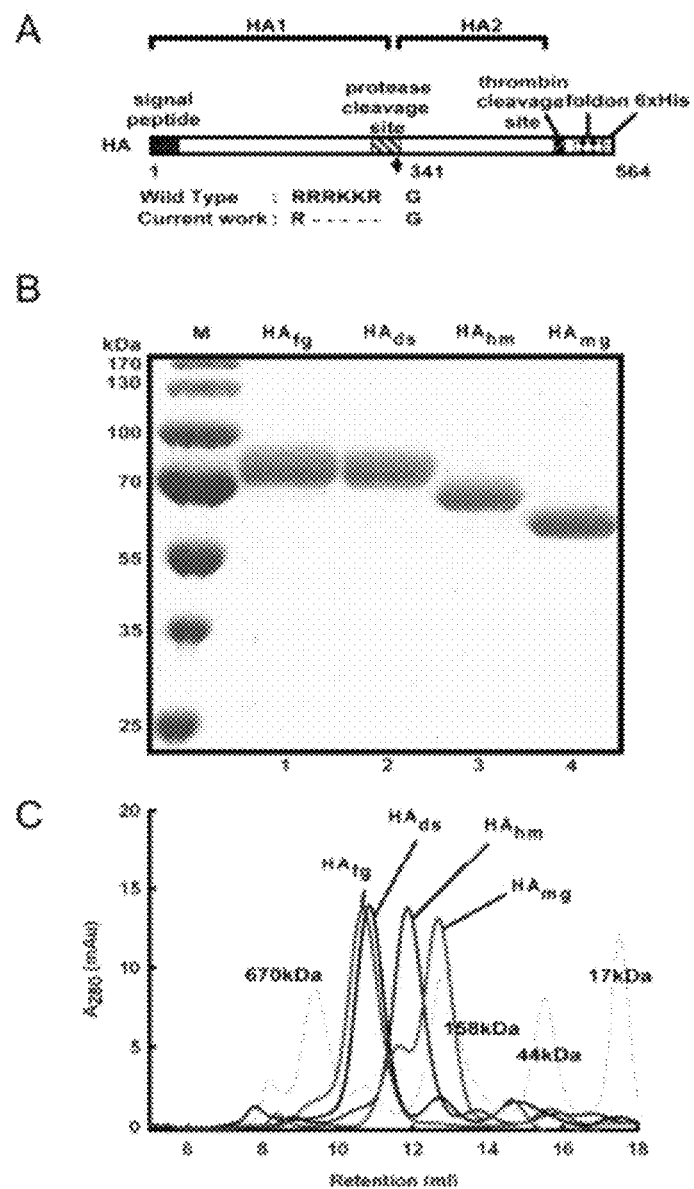
FIG. 6 shows construction of the H5 HA protein, purification, and gel-filtration chromatography analysis. Panel A: The DNA encoding the ectodomain of HA with cleavage-site alternation was cloned into the mammalian expression vector, pTT (Durocher Y, et al. (2002) Nucleic Acids Res 30:E9), to allow for efficient secretion of HA proteins from HEK293 cell cultures. The original protease cleavage site of the HA was mutated to PQRERG (SEQ ID NO: 2) to avoid the processing of the HA0 into HA1 and HA2. To stabilize the trimeric conformation of the HA proteins, the "foldon" sequence, which is the bacteriophage trimerizing fragment, was engineered into the plasmid construct, and a His-tag was also added in the COOH terminus for purification purposes. The expression of HA proteins was carried out by transient transfection with the expression vector.
Figure 7:
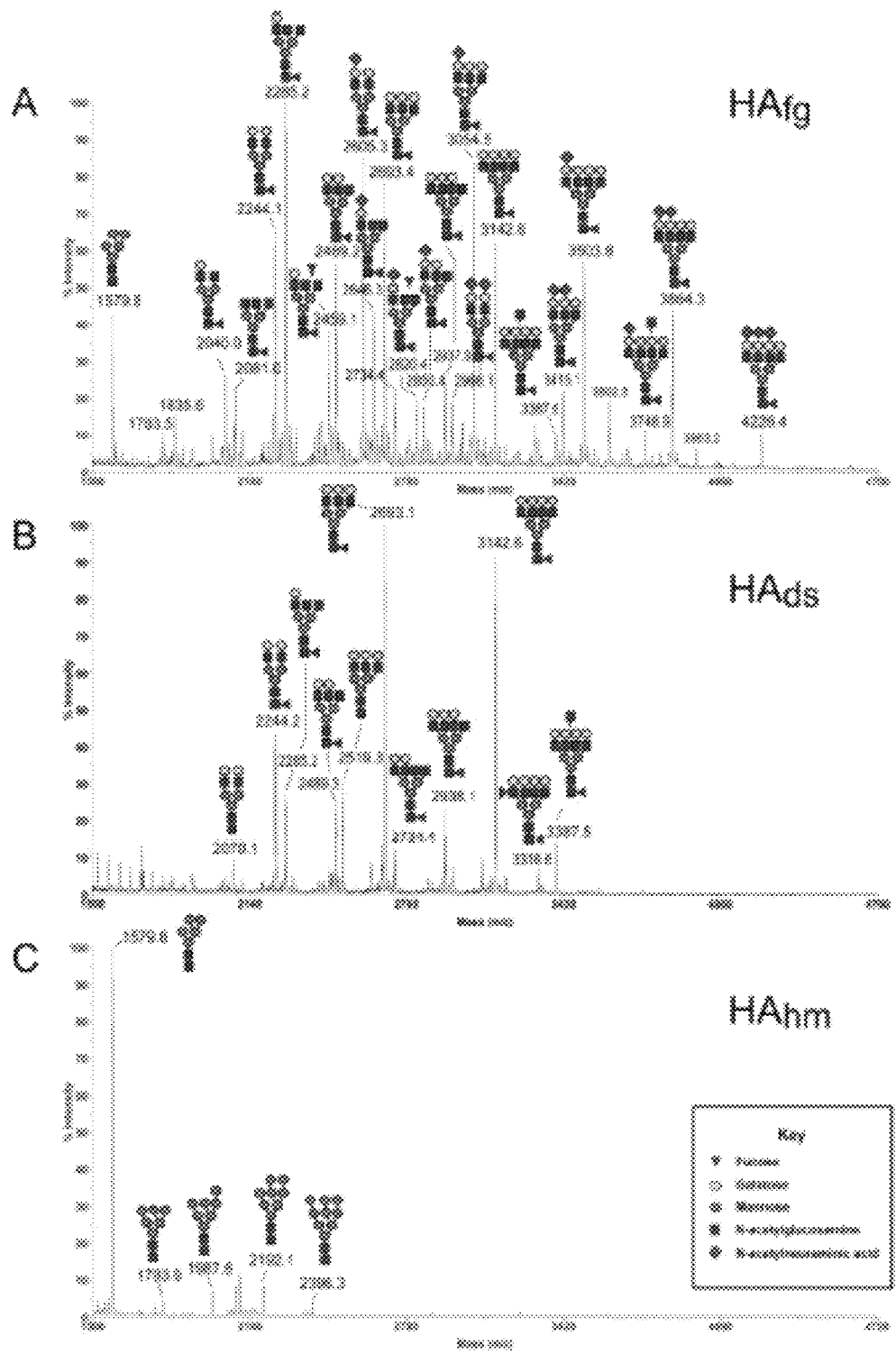
FIG. 7 shows mass spectrometry analysis of permethylated N-glycans from different HA proteins. MS analysis of permethylated N-glycans from different HA proteins. Panel A: The MALDI-MS profile showed that the N-glycans of HA expressed from HEK293E comprise predominantly core fucosylated, biantennary, triantennary, and tetraantennary complex-type N-glycan structures, as annotated for the major peaks detected. Assignment is based on composition, with only a limited few further verified by MS/MS analysis. The various degree of sialylation is a principal feature. Panel B: With NA treatment, all of the signals assigned as sialylated N-glycans (e.g., m/z 2605, 3054, 3503, 3864, 4226) were no longer detected, concomitant with an increase in signal intensities for the nonsialylated triantennary and tetraantennary structures (m/z 2693, 3142), fully consistent with complete removal of the sialic acids. Panel C: The MALDI-MS profile of the N-glycans derived from HA expressed in the GnTI$_1$-deficient HEK293S strain showed predominantly a signal corresponding to Man5GlcNAc2 at m/z 1579, along with minor peaks of incompletely trimmed high-mannose-type N-glycans (m/z 1783 to 2396; Hex6HexNAc2-Hex9HexNAc2) in the glycosylation pathway.
Figure 8:
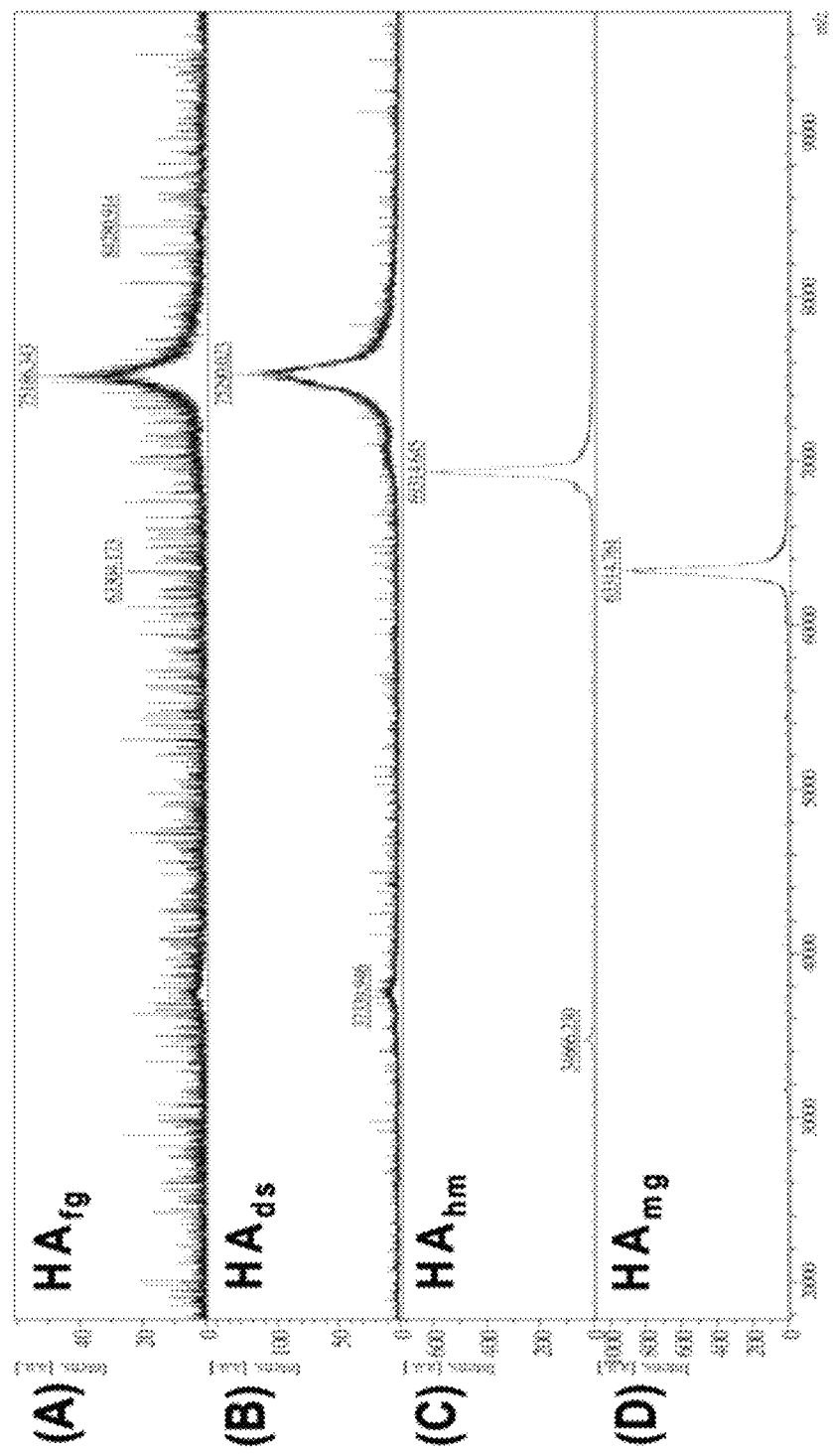
FIG. 8 shows MALDI-TOF analysis of HA variants. The molecular weights of (Panel A) $HA_{fg}$ is 75 186.343, (Panel B) $HA_{ds}$ is 75290.023, (Panel C) $HA_{hm}$ is 693 14.645 and (Panel D) $HA_{mg}$ is 63314.761.

The H5 consensus sequence was used to generate HA glycosylated variants expressed from HEK293 human cells. To generate high-mannose-type glycosylation ($HA_{hm}$), HEK293S cells, which are deficient in N-acetylglucosaminyltransferase I (GnTI⁻), were used. In order to further address the effect of HA glycosylation on receptor binding affinity and specificity, the sugars on HA were systematically removed from the native complex type N-glycans (FIG. 1A). Sialic acid residues were removed from $HA_{fg}$ by neuraminidase (NA) treatment to produce desialylated HA ($HA_{ds}$). Endoglycosidase H (Endo H) was used to truncate all of the glycan structures down to a single GlcNAc residue to produce monoglycosylated HA ($HA_{mg}$). Thus, a total of four glycoforms of HA were generated: $HA_{fg}$: fully glycosylated HA from human HEK293E cells; $HA_{ds}$ desialylated HA from neuraminidase (NA) treatment of $HA_{fg}$; $HA_{hm}$: high-mannose type HA from human N-acetylglucosaminyl transferase I deficient (GnTI-) HEK293S cells, and $HA_{mg}$: HA with single N-acetyl glucosamine residue at its glycosylation sites from Endoglucosidase H (Endo H) treatment of $HA_{hm}$ (FIG. 1, panel A and FIG. 6). The glycan structures are verified by mass spectral analysis (FIGS. 7, 8, 9). Circular dichroism of the variants confirmed that their secondary structures are similar (FIG. 1, panel C). The sole effect from N-glycans on HA of different glycoforms were then studied, assuming the protein 3D structures of these samples are similar and not causing bias in the analysis (FIG. 1, panel B). It is noted that an attempt to express functional HA in *Escherichia coli* failed because of the lack of glycosylation.

Moreover, mass spectrometry analyses confirmed that (a) $HA_{fg}$ contains predominantly the complex type N-glycans (FIG. 7, panel A); (b) the sialic acids have been removed from the complex type N-glycans on $HA_{ds}$ (FIG. 7, panel B); (c) $HA_{hm}$ contains predominantly the high mannose type N-glycans (FIG. 7, panel C); and (d) $HA_{mg}$ showed only an N-acetylglucosamine (GlcNAc) on HA (FIG. 1 and FIG. 8).

Glycan Microarray Profiling of HA Glycosylated Variants

Glycan microarray profiling of HA glycosylated variants $HA_{fg}$, $HA_{ds}$, $HA_{hm}$, and $HA_{mg}$ were examined by using traditional sandwich method. The synthetic sialic acid glycan array consisted of 17 of the α2,3 (glycans 1-17) and 7 of the α2,6 (glycans 21-27) sialosides designed to explore the glycan specificity of influenza viruses (see FIG. 4). The synthetic sialosides with a five-carbon linker terminated with amine were prepared and covalently attached onto NHS-coated glass slides by forming an amide bond under aqueous conditions at room temperature. The printing procedure was based on the standard microarray robotic printing technology, as reported previously (Blixt O, et al. (2004) Proc Natl Acad Sci USA 101:17033-17038; Wang C C, et al. (2008) Proc Natl Acad Sci USA 105:11661-11666). HA variants were applied to the sialic acid slides and then hybridized with primary antibody, followed by detection with a secondary antibody conjugated to Cy3. This analysis indicated that the H5N1 HA consensus sequence specifically binds to α2,3 sialosides but not α2,6 sialosides (FIG. 2, panel A), in accordance with previous studies (Chandrasekaran A, et al. (2008) Nat Biotechnol 26:107-113; Stevens J, et al. (2008) J Mol Biol 381:1382-1394). Surprisingly, the binding strength with α2,3 sialosides grew successively stronger from $HA_{fg}$, $HA_{ds}$, and $HA_{hm}$, to $HA_{mg}$ (FIG. 2, panel A) by qualitative binding via relative fluorescence intensity.

Figure 2:
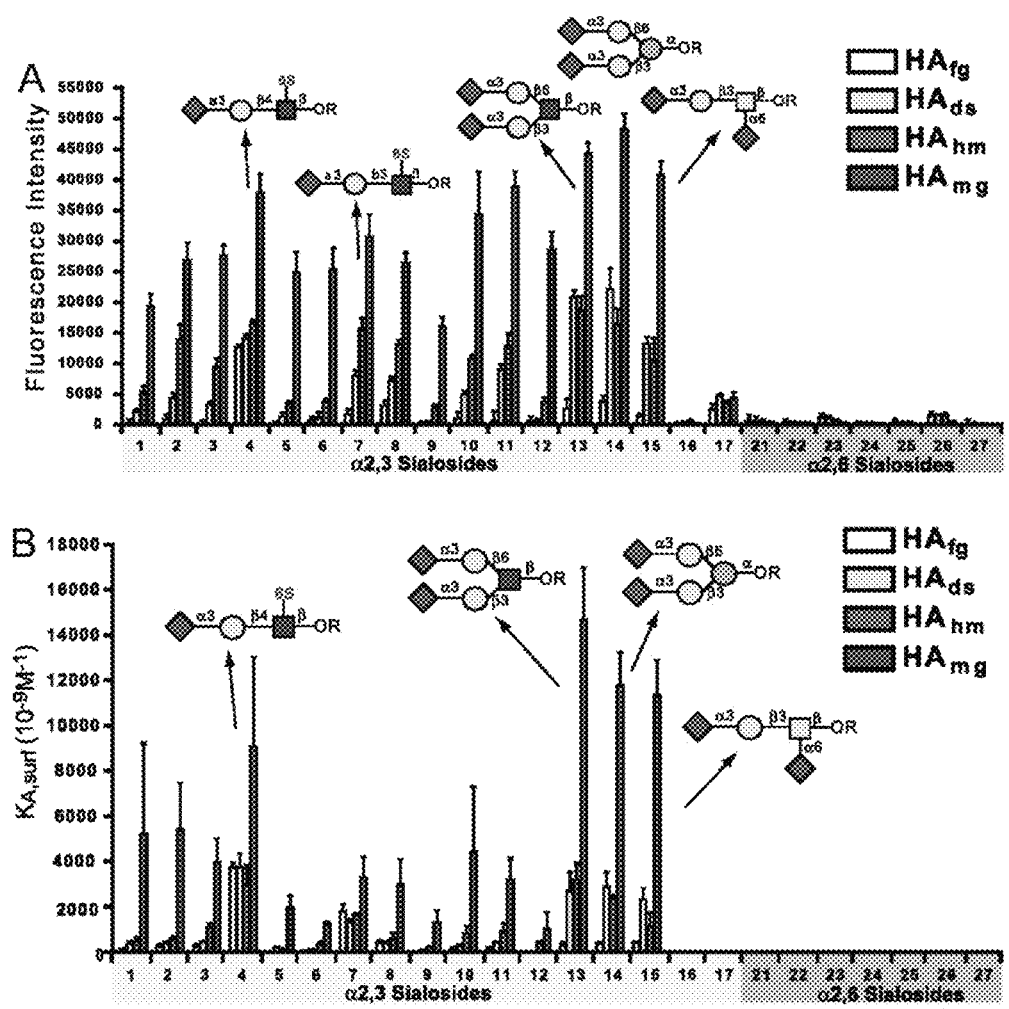
FIG. 2 shows glycan microarray analysis of HA with different glycosylations. Panel A: Glycan microarray profiling of HA variants $HA_{fg}$, $HA_{ds}$, $HA_{hm}$, and $HA_{mg}$ are shown. The related linkages of glycans were grouped by color, predominantly 17 α2,3 sialosides (yellow) or 7 α2,6 sialosides (blue). The structures of glycans on the array are indicated in Panel B. Association constants of HA variants $HA_{fg}$, $HA_{ds}$, $HA_{hm}$, and $HA_{mg}$ are shown with values of $K_{A,surf}$ of HA variants in response to α2,3 sialosides 1-15.

HAs were contacted with a synthetic glycan array containing 17 α2-3 (glycan 1-17) and 7 α2-6 (glycan 21-27) sialosides designed for influenza virus (FIG. 4), and then the HA proteins were hybridized with unlabeled primary followed by detection by Cy3 tagged secondary antibody. The analysis indicated that influenza H5NI hemagglutinin of consensus sequence can specifically bind to α2-3 sialosides but not α2-6 sialosides (FIG. 2A). Surprisingly, the binding with α2-3 sialosides was successively stronger from $HA_{fg}$, $HA_{ds}$, $HA_{hm}$, to $HA_{mg}$ (FIG. 2, panel A) in the intensity comparison of glycan array profiling.

Quantitative Glycan Microarray

Glycan array profiling has been limited to the qualitative natures in binding events investigation because it only provides the relative fluorescence intensity, and users cannot differentiate the binding affinity to receptors from the separate experiments. In order to precisely determine the binding events, this microarray platform was extended to determine the dissociation constants of HA-glycan interactions quantitatively.

A quantitative array was designed to determine surface dissociation constants (Liang P H, at el. (2007) J Am Chem Soc 129:11177-11184). To avoid any skewing by antibody layering, HA was directly labeled with the fluorescent dye Cy3 (Srinivasan A, et al. (2008) Proc Natl Acad Sci USA 105:2800-2805). Direct binding assays were performed by serial dilution of Cy3-labeled HAs to establish the relative binding intensities. The dissociation constants on the surface were determined by plotting the HA concentrations against fluorescence intensity for each of the 24 sialosides printed on the glass slide. The dissociation constant $K_{D,surf}$ values were calculated based on the Langmuir isotherms (see FIG. 2, panel B). The monovalent HA-sialoside binding is weak, exhibiting dissociation constants in the millimolar range ($K_D$=2.5×10$^{-3}$ M) (Sauter N K, et al. (1989) Biochemistry 28:8388-8396); however, HA is involved in multivalent interactions with sialosides on the host cell surface, which can be seen in the quantitative array profiling (Table 2). The $K_{D,surf}$ values decreased globally and substantially as the length of N-glycans on HAs decreased (FIG. 2, panel B).

All HA glycoforms showed strong binding to receptor glycans with a sulfate group at the 6 position of the third GlcNAc residue from the nonreducing end (glycans 4 and 7). This sulfate group is important for binding to H5 HA (Chandrasekaran A, et al. (2008) Nat Biotechnol 26:107-113; Stevens J, et al. (2008) J Mol Biol 381:1382-1394). In addition, it was observed that glycan 4 is the best ligand for $HA_{fg}$, whereas glycans 13-15 are better ligands than glycan 6 for $HA_{mg}$, indicating a possible multivalent interaction within the ligand-binding site, or the exposure of more receptor-binding domains to bigger biantennary sialosides (glycans 13 and 14). Interestingly, HA binding substantially increases as its N-glycan structures become less complex (FIG. 2, panel B). However, although the $K_{D,surf}$ values for $HA_{mg}$ show stronger and similar binding to a few SA glycans, the other HA variants exhibit weaker and more specific binding to glycan ligands (FIGS. 2, panel B and 10). Thus, binding specificity and binding affinity may have an inverse relationship that is modulated by glycan structure. This modulation may have important biological significance, in that the carbohydrates on HA can tune its recognition of glycan receptors on the lung epithelial cells.

Binding Energy Contribution from Receptor Sialosides

Kinetic parameters can be applied to thermodynamic parameters to illustrate the interaction events in molecular details. The dissociation constant ($K_{D,surf}$) of HA-glycan interactions can be used to calculate the Gibbs free energy change of binding ($\Delta G_{multi}$). Values for $\Delta G_{multi}$ represent a quantitative measurement of stabilizing energy from HA-glycan interactions. A successive decrease in $\Delta G_{multi}$ correlated with the systematic decrease in complexity/truncation of the N-glycan structures on HA (Table 2).

TABLE 2

Dissociation constants ($K_{D, surf}$) and free energy changes ($\Delta G$) of HA glycosylated variants when binding to α2,3 sialosides 1-15

| | $K_{D, surf}$ µM ± SD | | | | ANOVA | $\Delta G$, kcal/mol ± SD | | | |
|---|---|---|---|---|---|---|---|---|---|
| Sialosides | $HA_{fg}$ | $HA_{ds}$ | $HA_{hm}$ | $HA_{mg}$ | P* | $HA_{fg}$ | $HA_{ds}$ | $HA_{hm}$ | $HA_{mg}$ |
| 1 | 6.99 ± 0.41 | 2.86 ± 0.93 | 2.09 ± 0.59 | 0.27 ± 0.16 | <0.0001 | −7.03 ± 0.03 | −7.58 ± 0.19 | −7.76 ± 0.17 | −8.80 ± 0.15 |
| 2 | 3.72 ± 1.01 | 2.47 ± 0.21 | 1.75 ± 0.32 | 0.20 ± 0.07 | 0.0002 | −7.41 ± 0.16 | −7.66 ± 0.06 | −7.86 ± 0.11 | −9.03 ± 0.07 |
| 3 | 4.55 ± 1.85 | 2.34 ± 0.27 | 0.92 ± 0.16 | 0.26 ± 0.06 | 0.0002 | −7.31 ± 0.25 | −7.68 ± 0.07 | −8.24 ± 0.10 | −8.90 ± 0.01 |
| 4 | 0.27 ± 0.01 | 0.27 ± 0.05 | 0.33 ± 0.09 | 0.13 ± 0.06 | 0.0048 | −8.96 ± 0.03 | −8.95 ± 0.10 | −8.84 ± 0.16 | −9.45 ± 0.27 |

TABLE 2-continued

Dissociation constants ($K_{D,surf}$) and free energy changes ($\Delta G$) of HA glycosylated variants when binding to α2,3 sialosides 1-15

| | $K_{D,surf}$ µM ± SD | | | | ANOVA | ΔG, kcal/mol ± SD | | | |
|---|---|---|---|---|---|---|---|---|---|
| Sialosides | $HA_{fg}$ | $HA_{fg}$ | $HA_{fg}$ | $HA_{fg}$ | P* | $HA_{fg}$ | $HA_{fg}$ | $HA_{fg}$ | $HA_{fg}$ |
| 5 | ND | 5.20 ± 1.01 | 9.40 ± 3.20 | 0.54 ± 0.15 | ND | ND | −7.21 ± 0.11 | −6.88 ± 0.21 | −8.49 ± 0.13 |
| 6 | 20.03 ± 4.24 | 9.22 ± 2.05 | 2.71 ± 0.53 | 0.80 ± 0.05 | <0.0001 | −6.41 ± 0.13 | −6.87 ± 0.13 | −7.65 ± 0.06 | −8.32 ± 0.05 |
| 7 | 0.57 ± 0.10 | 0.77 ± 0.08 | 0.61 ± 0.02 | 0.32 ± 0.10 | 0.0010 | −8.46 ± 0.06 | −8.36 ± 0.04 | −8.47 ± 0.02 | −8.78 ± 0.14 |
| 8 | 2.49 ± 0.58 | 2.48 ± 0.41 | 1.69 ± 0.53 | 0.36 ± 0.13 | 0.0008 | −7.65 ± 0.14 | −7.65 ± 0.10 | −7.89 ± 0.21 | −8.82 ± 0.30 |
| 9 | ND | 15.34 ± 5.06 | 4.40 ± 0.56 | 0.86 ± 0.34 | ND | ND | −6.58 ± 0.20 | −7.31 ± 0.08 | −8.18 ± 0.16 |
| 10 | 7.64 ± 2.3 | 3.61 ± 0.61 | 1.22 ± 0.52 | 0.29 ± 0.14 | 0.0003 | −6.99 ± 0.18 | −7.43 ± 0.10 | −8.09 ± 0.24 | −8.77 ± 0.03 |
| 11 | 6.02 ± 1.04 | 2.32 ± 0.14 | 1.11 ± 0.51 | 0.33 ± 0.08 | <0.0001 | −7.12 ± 0.10 | −7.68 ± 0.04 | −8.15 ± 0.25 | −8.91 ± 0.18 |
| 12 | 40.23 ± 9.77 | ND | 2.45 ± 0.52 | 1.41 ± 0.92 | ND | −6.00 ± 0.15 | ND | −7.66 ± 0.12 | −7.85 ± 0.25 |
| 13 | 3.38 ± 1.06 | 1.37 ± 0.30 | 0.31 ± 0.06 | 0.07 ± 0.01 | 0.0008 | −7.47 ± 0.19 | −8.05 ± 0.13 | −8.88 ± 0.13 | −9.77 ± 0.09 |
| 14 | 2.72 ± 0.41 | 0.97 ± 0.41 | 0.42 ± 0.03 | 0.09 ± 0.01 | <0.0001 | −7.59 ± 0.09 | −8.27 ± 0.28 | −8.69 ± 0.04 | −9.60 ± 0.01 |
| 15 | 2.37 ± 0.19 | 1.32 ± 0.16 | 0.89 ± 0.35 | 0.09 ± 0.01 | 0.0002 | −7.67 ± 0.05 | −8.02 ± 0.07 | −8.29 ± 0.27 | −9.62 ± 0.08 |

Table 2 shows thermodynamic parameters of HA with different glycosylations in response to α2,3 sialosides 1-15. Free energy changes (ΔG) and $K_{D,surf}$ of HA-glycan interactions are shown in response to α2,3 sialosides 1-15. ΔG values can be derived from $K_{D,surf}$ values by using the equation $\Delta G_{multi} = -RT \ln(K_{D,surf}^{-1})$. The values of ΔG were calculated according to $K_{D,surf}$ values to obtain free energy changes in HA-glycan binding. $\Delta G(HA_{fg})$ of glycans 5 and 9 is not determined. ND indicates not determined. (*From the set of 15 identified HA-binding sialosides, statistically significant differences of $K_{D,surf}$ values among four HA glycoforms are shown by using a one-way ANOVA (P<0.05 is considered significant)).

The differences in free energy change (ΔΔG) between HA variants are caused by unique glycan structures (FIG. 10), and the largest difference is between $HA_{fg}$ and $HA_{mg}$ (ΔΔG $HA_{fg} \rightarrow HA_{mg}$; see FIG. 10), which is consistent with the largest difference in binding energy resulting from trimming off most of the N-glycan down to a single GlcNAc. It is noted that values of ΔΔG are similar except for glycans 4 and 7 (FIG. 10), indicating that glycans on HA do not significantly affect the binding affinity with sulfated α2,3 trisaccharide (Chandrasekaran A, et al. (2008) Nat Biotechnol 26:107-113).

HA-Receptor Binding

Figure 4:
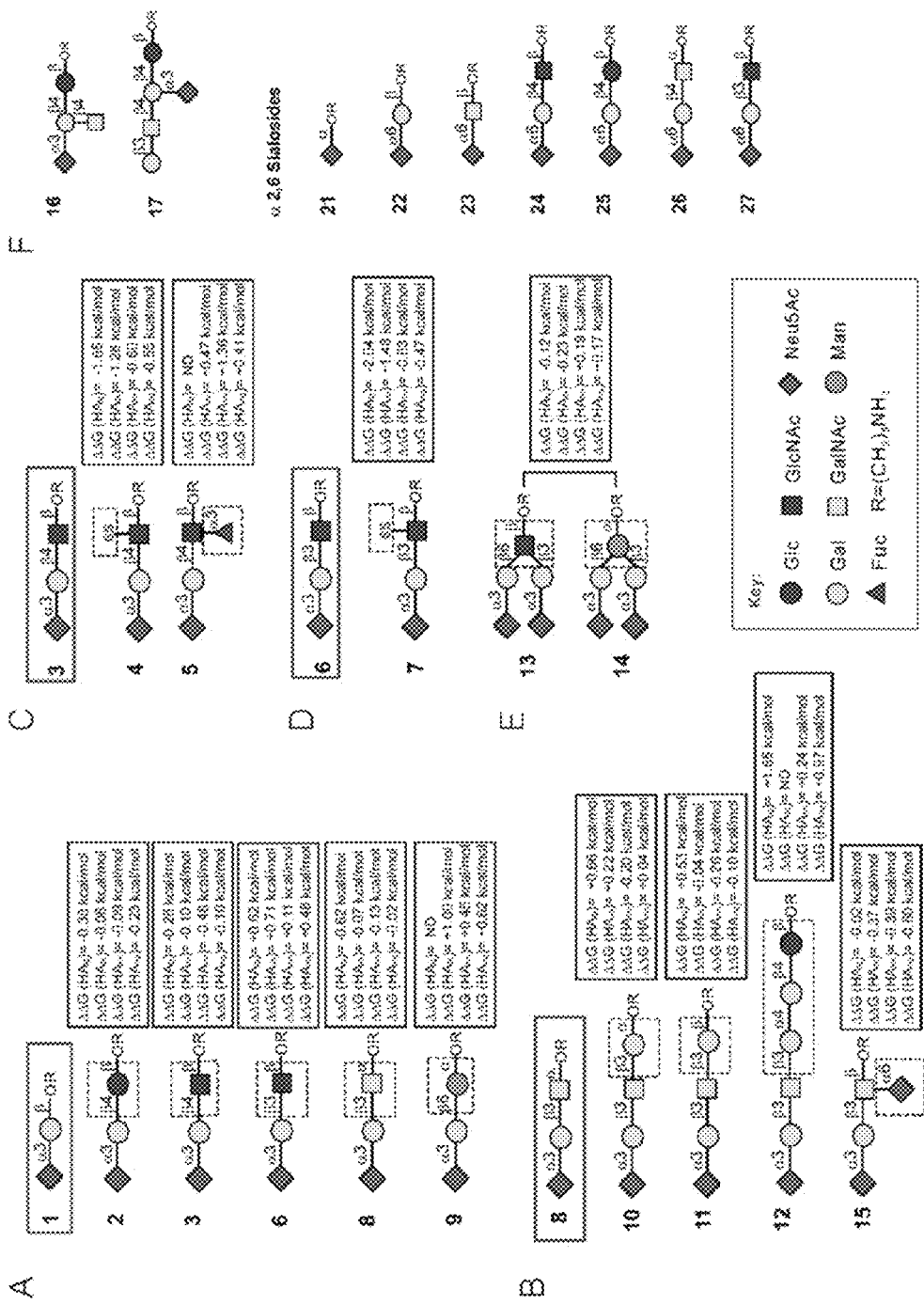
FIG. 4 shows the binding energy contributions from sugars or modifications of HA glycan interactions in response to HAs with different glycosylations. These values were obtained by subtraction of ΔG values of the indicated reference. Panel A: Glycans 2, 3, 6, and 8-10 possess the same backbone of the disaccharide glycan 1 but only differ in the third sugar from the nonreducing end. The values of ΔΔG are calculated to demonstrate the binding energy difference by changing the third sugars. Panel B: Glycans 10-12 and 15 possess the same backbone of the disaccharide glycan 8 but differ either by elongating the sugar structure linearly or by adding a branched sugar. Panel C: Glycans 4 and 5 possess the same backbone of the trisaccharide glycan 3 but differ either by the branched fucose or the sulfate group on the third position from the nonreducing end. Panel D: Glycans 6 and 7 differ in the sulfate group on the third position from the nonreducing end of glycan 7. Panel E: Glycans 13 and 14 are α2,3 biantennary sialosides but differ in the change of the internal sugar. Panel F: Glycans 16 and 17 and α2,6 sialosides (nos. 21-27) show little or no binding to HA.

The molecular details of the HA-receptor binding (i.e., the contribution from each structural component comprising a glycan receptor) can be addressed by comparing the differences in free energy change (ΔΔG values) between different receptor sialosides (FIGS. 4 and 11). Dissecting the energy contribution of the receptor sialosides responsible for HA binding reveal key points of specificity that are used to design new HA inhibitors. Sialosides α2,3 linked to galactose residues with β1,4 (Galβ1-4) linkages possess better binding affinity than those with Galβ1-3 linkages (Stevens J, et al. (2008) J Mol Biol 381:1382-1394). This is reflected in the comparison of the Neu5Ac-α2,3-galactose (Neu5Acα2, 3Gal) disaccharide backbone (FIG. 4, panel A, glycan 1, red box highlight), where trisaccharides 3 and 6 only differ in the linkage between Gal and GlcNAc. Here, the ΔΔG(1→3) for all HA variants is negative (stabilizing HA-receptor interaction), whereas the ΔΔG(1→6) for all HA variants is positive (destabilizing HA-receptor interaction; FIGS. 4A and 11). This observation indicates that Neu5Ac-α2, 3Galβ1-4Glc/GlcNAc is the core glycan component interacting with the HA-binding pocket. Moreover, the value of ΔΔG(1→9) for all HA variants is positive, indicating a negative perturbation caused by the β6-linked mannose at the third position (FIGS. 4, panel A and 11). Thus, binding energy is affected by inner sugar residues and their linkage patterns to the distal Neu5Ac-α2,3Gal disaccharide ligand (FIG. 4, panel A). This analysis shows that a GlcNAc residue at the third position is favored for all HA variants. However, in comparing ΔΔG values for glycans 13 and 14 (FIGS. 4, panel E and 11) to glycan 6, multivalent interactions in the binding site with the biantennary sialoside are apparent, and for $HA_{mg}$, this intramolecular avidity is more significant for driving binding than the structural effect exerted by the third sugar.

Next, receptor glycans 10, 11, 12, and 15 were compared. These have the same basic core structure (glycan 8 trisaccharide) but differ by elongation (glycans 11 and 12) or addition of an α2,6 sialic acid at the third position (glycan 15; FIG. 4, panel B). It is interesting that the sialoside with the branched α2,6 sialic acid greatly increased HA avidity, whereas the longer α2,3 sialoside extending from glycan 8 resulted in a weaker binding by HAs (ΔΔG (8→15)>ΔΔG (8→11)~ΔΔG (8→10)>ΔΔG (8→12); FIG. 4, panel B and 11).

Glycans 3-5 and 6-7 share the same trisaccharide backbone but differ by the addition of a sulfate group (glycan 4) or fucose residue (glycan 5) on the third GlcNAc from the nonreducing end. The sulfate group can stabilize the HA-receptor glycan interaction up to 2.044 kcal/mol (ΔΔG (6→7)), the largest energy gap between two receptor sialosides. Among all of the HA variants, the fully glycosylated variant showed the most significant differences in free energy changes, with values of ΔΔG(3→4) $HA_{fg}$ (−1.653 kcal/mol) and ΔΔG(6→7) $HA_{fg}$ (−2.044 kcal/mol), and the size of the free energy gain lessened as the glycan structure became more simplified; i.e., $HA_{fg}>HA_{ds}>HA_{hm}>HA_{mg}$. Thus, sulfated glycans dramatically enhance HA binding, and fully glycosylated HA maximizes this effect (FIG. 4, panels C and D), which is important for H5N1 pathogenesis. On the other hand, the fucosylated receptor analogs greatly destabilize HA binding, with all glycosylated HA variants showing a positive ΔΔG(3→5) (FIG. 4C). These large differences in ΔΔG(3→4) and ΔΔG(3→5) are likely caused by an important binding interaction in the receptor-binding pocket, which the sulfate group maximizes and the fucose sterically blocks. The weak binding of $HA_{fg}$ is unlikely due to the competition of its sialylglycans, because removal of sialic acid has a small effect on binding, and $HA_{fg}$ still exhibits a strong affinity for certain specific sialylglycans.

Vaccine Design Using Monoglycosylated HA

The monoglycosylated hemagglutinin $HA_{mg}$ shows a similar secondary structure and better binding affinity to host receptors as compared to its fully glycosylated counterpart.

Figure 5:
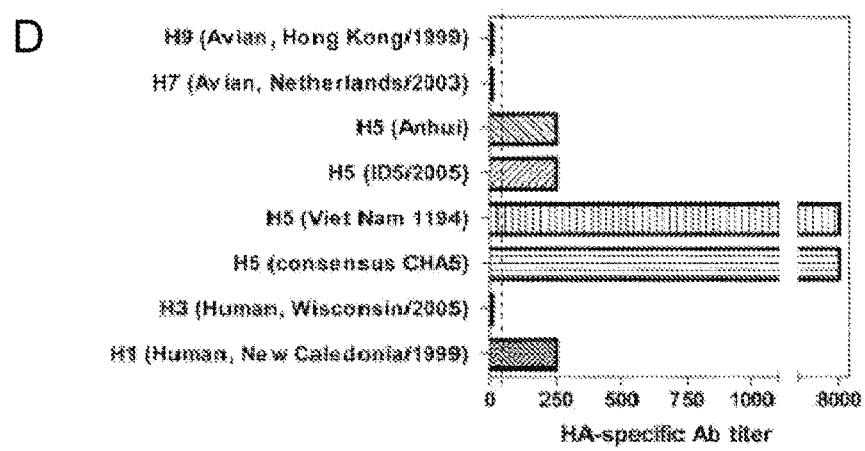
FIG. 5 shows a comparison of $HA_{fg}$ and $HA_{mg}$ as vaccine. Panel A: The bindings between antisera from $HA_{fg}$ and $HA_{mg}$, and various HAs are analyzed by using ELISA. In comparison with $HA_{fg}$ antiserum, $HA_{mg}$ antiserum shows better binding to H5 (Vietnam 1194/2004 and CHA5). In addition, the $HA_{mg}$ antiserum also binds to H1 (California 07/2009 and WSN). Panel B: Microneutralization of H5N1 (NIBRG-14) virus with $HA_{fg}$ and $HA_{mg}$ antisera. In comparison with $HA_{fg}$ antiserum, $HA_{mg}$ antiserum shows better neutralizing activity against influenza virus infection to MDCK cells (P<0.0001). Panel C: Vaccine protection against lethal-dose challenge of H5N1 virus. BALB/c mice were immunized with two injections of the HA protein vaccine $HA_{fg}$, $HA_{mg}$, and control PBS. The immunized mice were intranasally challenged with a lethal dose of H5N1 (NIBRG-14) virus. After challenge, the survival was recorded for 14 days. Panel D: The binding of rabbit antiserum from $HA_{mg}$ with different HAs by ELISA. The rabbit antiserum against $HA_{mg}$ demonstrated strong binding to H5 (CHA5 and Vietnam/1194). In addition, interactions with H5 (Anhui and ID5/2005) and H1 (New Caledonia/1999) are also observed.

Recent studies also indicated that a single GlcNAc residue to Asn is the minimum component of the N-glycan required for glycoprotein folding and stabilization (Hanson S R, et al. (2009) Proc Natl Acad Sci USA 106:3131-3136). Because proteins are superior immunogens to glycans, the monoglycosylated HA was tested as a protein vaccine against influenza viruses. Antisera from $HA_{fg}$ and $HA_{mg}$ immunizations were compared with regard to their ability to bind native HAs and to neutralize H5 viruses (FIG. 5). Indeed, in contrast to $HA_{fg}$, the antiserum from $HA_{mg}$ showed stronger neutralization of the virus. The $HA_{mg}$ antiserum also binds to H1 (New Caledonia/1999) in addition to the H5 subtypes Vietnam/1194, H5 (Anhui), and H5 (ID5/2005) (FIG. 5, panel D). Notably, the $HA_{mg}$ vaccine was much more protective than the $HA_{fg}$ vaccine in a challenge study (FIG. 5, panel C).

Figure 3:
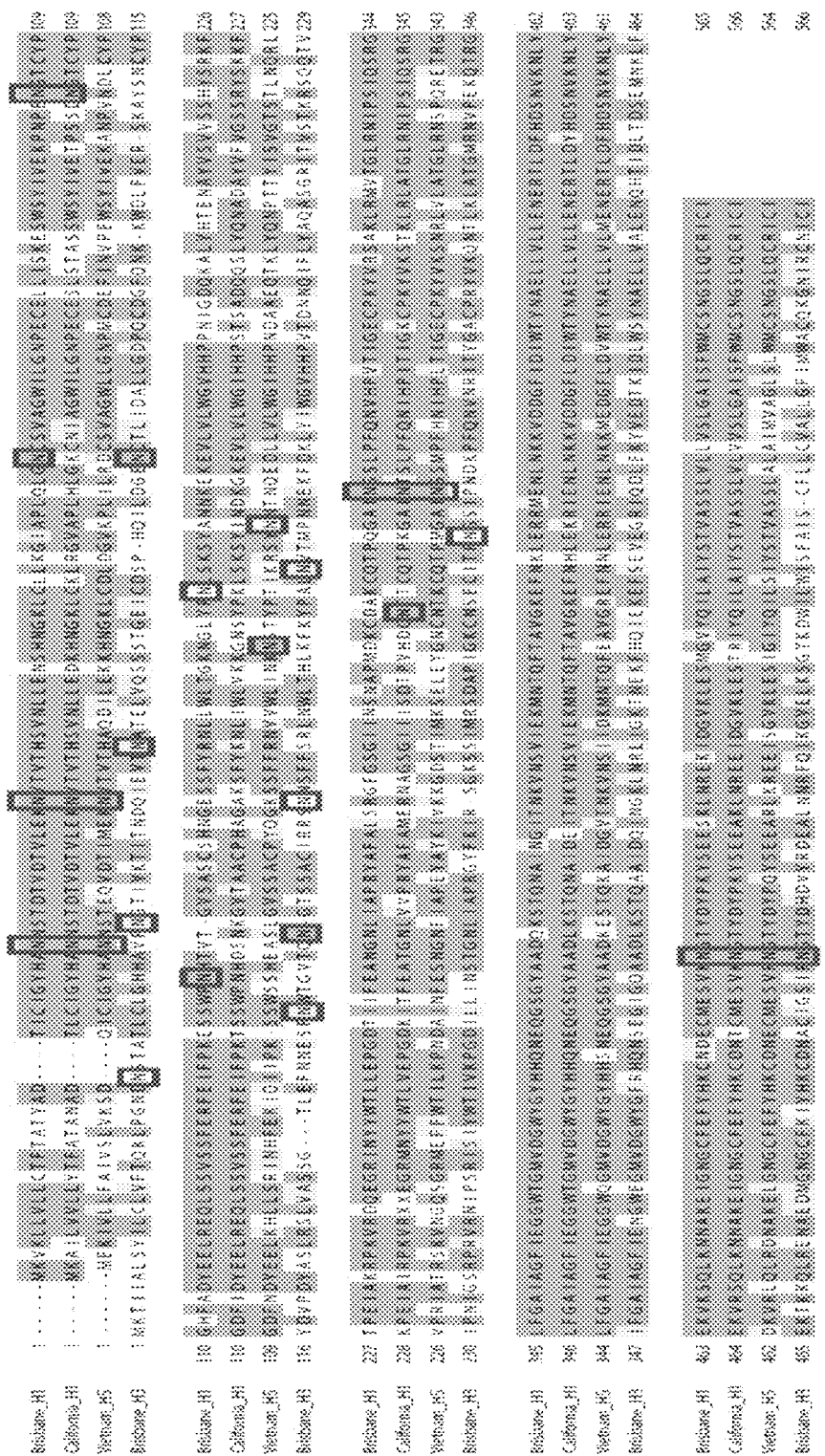
FIG. 3 shows Sequence alignment analysis of Brisbane H1, California H1, H3 and H5 of recent HAs H1, H3, and H5 since 2000. Seasonal flu HA is from A/Brisbane/59/2007. Pandemic flu HA is from A/California/07/2009. HA from H1N1 A/Brisbane/59/2007:SEQ ID NO: 16. HA from H1N1 A/California/07/2009:SEQ ID NO: 17. HA from H5N1 A/Vietnam/1203/2004:SEQ ID NO: 18. HA from H3N2 A/Brisbane/10/2007:SEQ ID NO: 19. H5 is from A/Vietnam/1203/2004. H3 is from A/Brisbane/10/2007. The N-glycosylation sites on H5 HA are shown in a red box. The comparison reveals similarity between H1 and H5 HAs in their N-glycosylation positions, whereas H3 has less-conserved glycosylation positions and differs from H1 and H5.

The amino acid sequences of H1, H3, and H5 isolated from humans were compared I FIG. 3. When comparing H1 vs. H3 and H3 vs. H5, differences in the overall amino acid sequences as well as those near N-glycosylation sites are observed. H1 and H5 show higher overall amino acid sequence similarities, and the sequences near N-glycosylation sites are more conserved. Seasonal (A/Brisbane/59/2007) and Pandemic (A/California/07/2009) H1 strains show about 79% sequence identity. The overall sequence identity was about 63% between H1 and H5, and about 40% between both H3 and H5, and H1 and H3. In addition, the N-glycosylation sites (shown within red boxes in FIG. 3) and the underlying peptide sequences are more conserved between H1 and H5 than between H1/H3 and H5.

The present invention shows that the systematic simplification of N-glycans on HA results in a successive increase in binding to α2,3 sialosides but not to α2,6 sialosides. The inventors, for the first time, show the effect of HA's outer and inner glycans on receptor binding and to quantitatively dissect the binding affinity and energetic contributions of HA-receptor interactions.

HA glycosylation affects the function of influenza HA (Wagner R, et al. (2002) J Gen Virol 83:601-609). Interestingly, as the level of glycosylation on influenza H3N2 has increased since 1968, the morbidity, mortality, and viral lung titers have decreased (Vigerust D J, et al. (2007) J Virol 81:8593-8600).

Without being bound by theory, the finding that HA with a single GlcNAc attached to the glycosylation sites shows relaxed specificity but enhanced affinity to α2,3 sialosides suggests that the N-glycans on HA may cause steric hindrance near the HA-receptor binding domain. The high specificity for receptor sialosides may prevent the virus from binding to some other specific glycans on the human lung epithelial cell surface. On the other hand, HA with truncated glycans can recognize α2,3 receptor sialosides with higher binding affinity and less specificity, suggesting that reducing the length of glycans on HA may increase the risk of avian flu infection. It is, however, unclear how the changes of HA-receptor interaction via glycosylation affect the infectivity of the virus and the NA activity in the viral life cycle.

HA with a single GlcNAc is a promising candidate for influenza vaccine because such a construct retains the intact structure of HA and can be easily prepared (e.g., via yeast). It also can expose conserved epitopes hidden by large glycans to elicit an immune response that recognizes HA variants in higher titer. This strategy opens a new direction for vaccine design, and together with other different vaccine strategies (Hoffmann E, et al. (2005) Proc Natl Acad Sci USA 102:12915-12920; Huleatt J W, et al. (2008) Vaccine 26:201-214; Scanlan C N, et al. (2007) J Mol Biol 372:16-22; Yang Z Y, et al. (2007) Science 317:825-828) and recent discoveries of HA-neutralizing antibodies (Ekiert D C, et al. (2009) Science 324:246-251; Kashyap A K, et al. (2008) Proc Natl Acad Sci USA 105:5986-5991; Scheid J F, et al. (2009) Nature 458:636-640; Stevens J, et al. (2006) Science 312:404-410; Sui J H, et al. (2009) Nat Struct Mol Biol 16:265-273), should facilitate the development of vaccines against viruses such as influenza, hepatitis C virus, and HIV.

Therefore, whether HA with a single GlcNAc can be a promising candidate for influenza vaccine was tested. For the benefits of its strong binding with 0.2-3 sialosides, HA with a single GlcNAc can elicit immune response that recognize the region close to RBD with higher titers, indicating that the addition of oligosaccharides can be an effective means of immune evasion via the modification or masking of antigenic epitopes on the virus. Therefore, the strategy of removal of most glycans, but with at least a single GluNAc retaining opens a new direction for future vaccine design, and this concept provides insight into other antivirus vaccine design such as HCV, HBV, and HIV. Other iterations have two, three, or more glycans of the original glycan chain remaining.

Partially Glycosylated Cell-Surface Glycoproteins as Vaccines

The cell-surface glycoproteins of viruses are good targets for vaccine development. However, such surface proteins are often highly glycosylated by the host to protect the virus from the host's immune system. In addition, the viral protein sequences around the glycosylation sites are often highly conserved and thus are good antigen for the vaccine design, however, these highly conserved regions are not readily available to the host's immune system at least in part due to the amount of glycosylation covering or blocking those regions. For example, one reason for the limited success in the preparation of vaccines against intact HIV is because the viral surface gp120 is highly glycosylated.

The new vaccine is more immunogenic and the antibody induced is expected to have better neutralization activity against the intact glycoprotein, which is made by the virus and the host. The antibody is able to attack both the less or non-glycosylated region(s) which is more likely to mutate and the glycosylated region which is highly conserved, less likely to mutate and/or sensitive to mutation. An antibody generated thusly will strongly interact with the protein part of the target as such antibody has higher affinity for protein than carbohydrate and thus thermodynamically it will push the glycan chain away to bind the highly conserved regions around the glycosylation sites.

In the O- and N-linked glycoproteins, the first sugar (N-acetylglucosamine for N-glycoprotein and N-acetylglucosamine or N-acetylgalactosamine for O-glycoproteins) is essential to preserve the tertiary structure of the glycoprotein while the rest of the sugars are not important. Treatment of N-glycoproteins with the endoglycosidase (endoH) will remove the sugar chain and keep the N-acetyl glucosamine attached to the protein. Mannosidases may also be used to cleave N-glycoproteins to di- or triglycans, which are expressly contemplated herein as possible vaccines due to the ability of the immune system to access the conserved glycosylation sites on the proteins even with di-, tri-, and larger deglycosylated proteins. Other glycosidases are also available to remove the sugar chain from O-glycoproteins and keep the first sugar attached to the protein.

Figure 13:
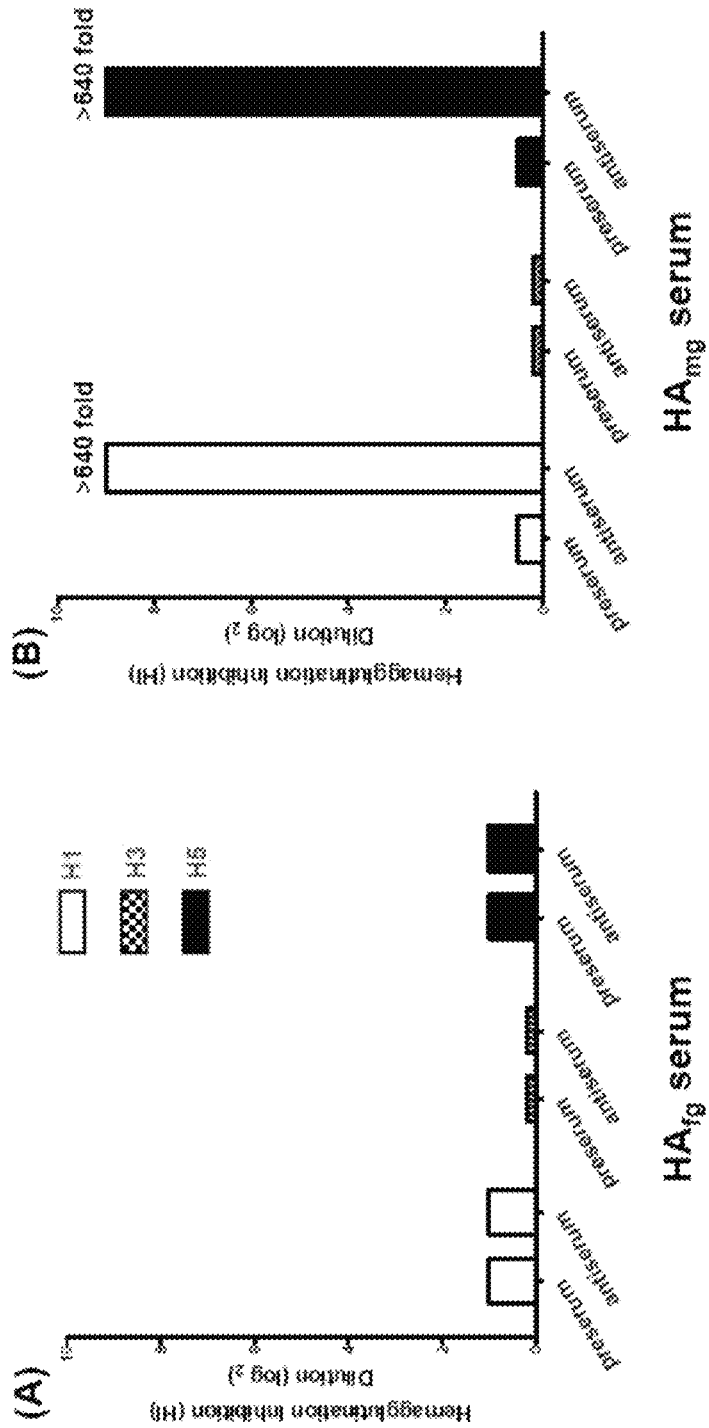
FIG. 13 shows the results of hemagglutination assay with rabbit $HA_{fg}$ and $HA_{mg}$ antisera. Panel A: results with fully glycosylated consensus H5 HA antisera in hemagglutination assays towards H1, H3 and H5. Panel B: results with monoglycosylated H5 HA antisera. The monoglycosylated H5 HA antisera not only display good hemagglutination inhibition activity towards H5, but also towards H1. H3 hemagglutination is unaffected by either antisera.

When a fully glycosylated hemagglutinin (HA) from bird flu (H5) expressed in human cells is treated with endoH to reduce glycosylation to a monoglycosylated state and used in the immunization of rabbit, the antiserum generated has a higher titer than the antiserum generated from the fully glycosylated hemagglutinin. (FIG. 13, panels A and B). It is also able to neutralize the hemagglutinin from other bird flu strains and the hemagglutinin H1 from human flu while the antiserum from the fully glycosylated HA cannot neutralize H1 and is more specific for the bird flu strain.

Figure 12:
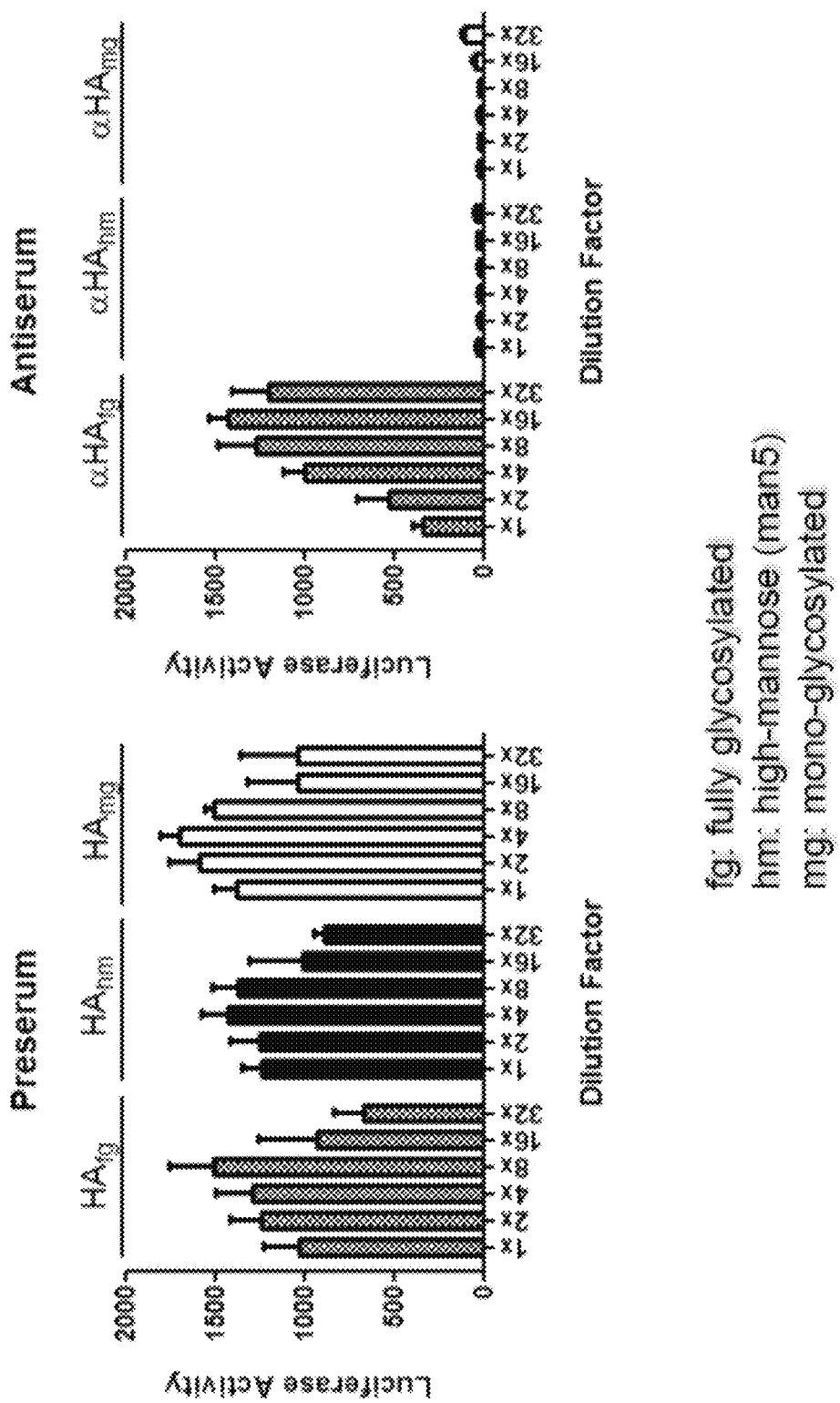
FIG. 12 shows the ability of antisera generated from fully glycosylated, high-mannose and monoglycosylated H5 HA, to inhibit Vietnam 1203 HA pseudotyped virus transduction into HEK293 cells. Both high-mannose and mono-glycosylated HA antisera inhibit virus entry, but fully glycosylated HA antisera does not.
Figure 14:
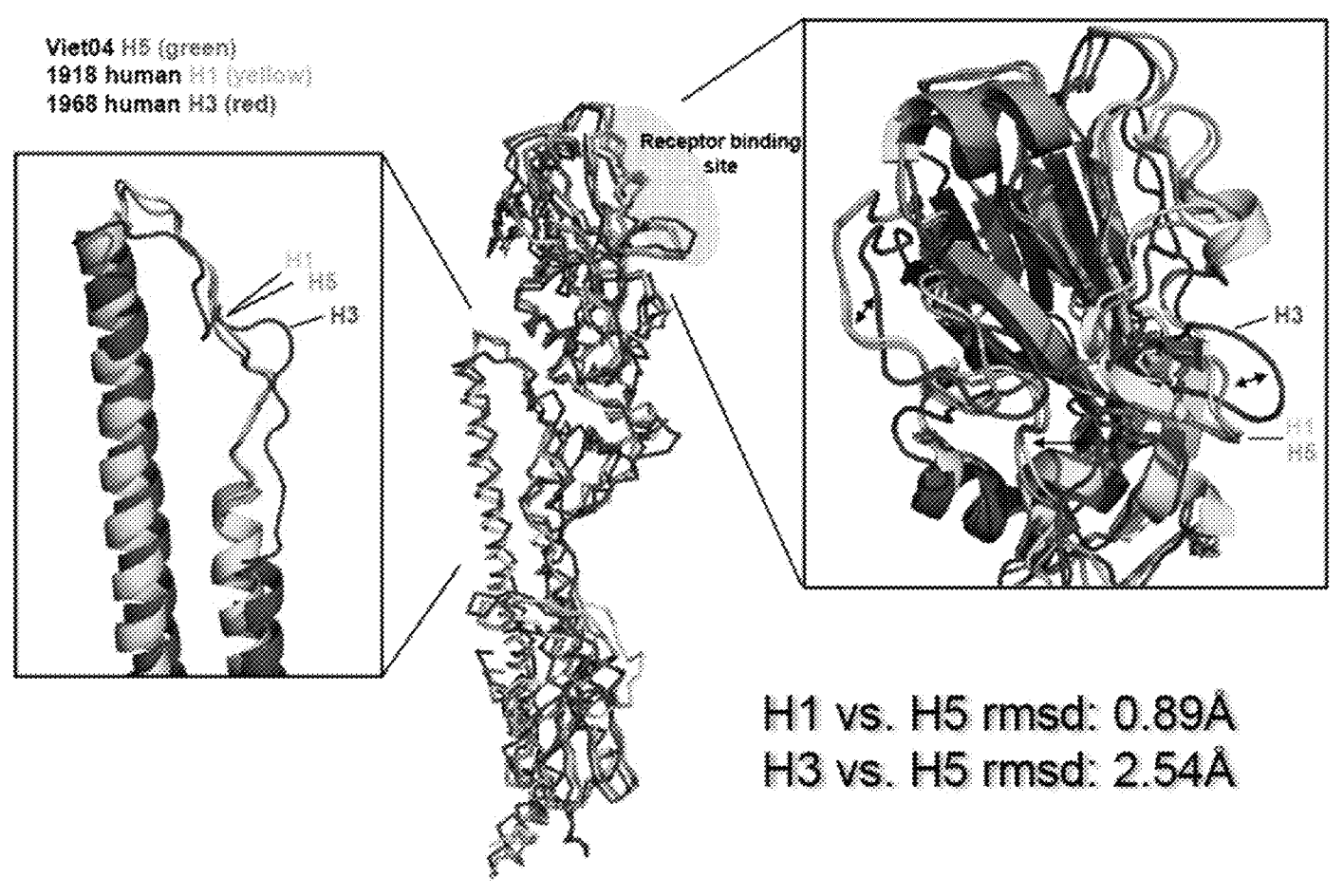

The similarity of glycosylation pattern and protein structure between H1 and H5 provides a possible reason why the mono-glycosylated H5 antiserum cross-reacts with H1. The data was obtained using rabbit antisera. (FIG. 13). As shown in FIGS. 12-14, the hemagglutinin of H3 does not have the same degree of homology as H5 HA does with H1 HA. Thus, antiserum generated from H1 and H5 do not neutralize H3. However, because H3 shares other homology in the conserved regions with H1 and H5, antiserum generated from deglycosylated hemagglutinin H3 neutralizes hemagglutinin H1 and hemagglutinin H5 in addition to hemagglutinin H3.

To prepare monoglycosylated hemagglutinin, it is not necessary to make the glycoprotein from human cell culture as the glycoprotein with the first three sugars (Mannose-N-acetylglucosamine-N-acetylglucosamine) or only the monosaccharide (N-acetylglucosamine) attached to the protein (i.e., N-acetylglucosamine-protein) is highly conserved in eukaryotes. Thus, one can make the glycoprotein in yeast, baculovirus, or other eukaryotic hosts and treat the glycoprotein mixture with the appropriate glycosidase, such as endoH or mannosidase for N-linked glycoproteins, to prepare the homogeneous monoglycosylated protein for use as vaccine.

Without being bound by theory, it is postulated that N-linked glycan is much longer than the O-linked glycan and it is the N-linked glycan that needs to be trimmed to remove the rest of sugar chains. Therefore, the O-linked glycan will not cause a problem even if it is intact.

A native glycoprotein that is exposed to the immune system has an N-linked branched glycoprotein. Because of the glycosylation, the highly conserved region is inaccessible to the immune system. Thus, the immune system can only target highly variable regions, thereby reducing the subject susceptible to multiple viral infections as the variable regions mutate. If the immune system is able to access the highly conserved regions, then antibodies directed to these sequences which do not vary over time provide a route towards inoculation against viruses that either have variable regions that mutate and thereby render existing antibodies against the glycoproteins ineffective or are so thickly glycosylated as to be substantially inaccessible to the immune system.

Therefore, to make the protein accessible to the immune system via a vaccine, the glycosylation is removed, thereby exposing the native viral protein to the immune system. Importantly, complete removal of the sugars from the protein has been shown to cause the protein to denature; in many viral glycoproteins, glycosylation is a key component to tertiary structure of the glycoprotein.

The sugars are removed by exposing the isolated native glycosylated proteins to a N-glycosidase, for example endoH or mannosidase, which will cleave all but the first one, two, or three sugars from the glycoprotein, without causing the protein to lose its tertiary structure. The deglycosylated proteins are then formulated with a suitable pharmaceutical carrier as a vaccine and administered to a subject. Because the highly conserved glycosylation regions are now deglycosylated and thereby exposed to the immune system, antibodies are generated against the highly conserved regions.

When the immunized subjects are infected with the virus and the viral glycoproteins are exposed to the immune system, the antibodies that are directed to the highly conserved regions of the protein are present in the subject's system. Thus, mutation in variable regions becomes irrelevant because there are still antibodies directed to the non-mutating conserved regions of the glycoprotein.

Moreover, glycosylation does not hinder binding of the antibodies to the highly conserved regions because the antibodies are thermodynamically inclined to bind the protein and "push" the sugars out of the way for binding of the antibodies to the highly conserved regions. Importantly, in viral proteins such as gp120 of HIV, this strategy provides a method and composition for inoculation where the immune system would otherwise not produce an antibody titer large enough to effectively fight the infection.

According to implementations embodying these principles, a vaccine comprising at least one deglycosylated hemagglutinin and a pharmaceutically acceptable carrier is contemplated. The vaccine can be made using any system that expresses glycosylated proteins, such as yeast and baculovirus. Once the proteins are made, they are isolated using a suitable method, such as gel electrophoresis, chromatography, or other methods capable of isolating proteins.

The pattern of glycosylation at the glycosylation site is conserved in nearly all eukaryotes (GlcNAc-GlcNAc-Man). Thus, it doesn't matter what the downstream glycosylation pattern is, provided that the first 1-3 (potentially more depending on the organism being inoculated and the organism producing the protein) sugars remain. Thus, for a human vaccine, yeast may be used to produce the protein used in a human vaccination, because once all but the first one to three sugars are cleaved, the pattern is identical to the first one to three sugars in the human version of the glycoprotein. Therefore, the present disclosure provides a unique platform for high throughput, high output production of vaccines against virus such as influenza, HIV, and flavivirus.

To generate the vaccines, the glycosylated proteins are isolated and then (partially) deglycosylated using a glycosidase, or another enzyme or method that selectively digests the carbohydrates forming the glycosylation. However, whatever method is used to cleave the sugar chains it must not affect the tertiary structure of the underlying protein.

The partially glycosylated glycoproteins, or fragments thereof, also can be prepared synthetically. There are two strategies for the synthesis of glycopeptides. (i) Stepwise method: glycosylamino acids are used as a building block for solid-phase synthesis. The advantage of this approach is "wide use" for the preparation of various glycopeptides. This approach allows the preparation of glycopeptides having some oligosaccharide moieties. (ii) Convergent method: an oligosaccharide moiety and a peptide moiety are prepared separately, then coupled with each other. Commonly, this approach is used for the preparation of N-glycopeptides. This approach requires a special orthogonal side-chain protecting group for the "glycosylation point" in the peptide moiety.

In one embodiment, N-acetylglucosamine (GlcNAc) attached to the asparagine residue of the peptide can be synthesized using a thioester method to build the polypeptide segment (Merrifield R B. J. Am. Chem. Soc. 85:2149 (1983)) and a dimethylphosphinothioic mixed anhyride (Mpt-MA) method for the incorporation of the glycopeptide moiety (Guo, Z W, et al. (1997) Angew. Chem. Int. Ed. Engl. 36, 1464-1466).

Cross-Reactive Influenza Vaccines Generated from Mono-Glycosylated HA Proteins (A) Vaccination with Seasonal H1 (Brisbane) Mono-Glycosylated HA Protein.

Figure 15:
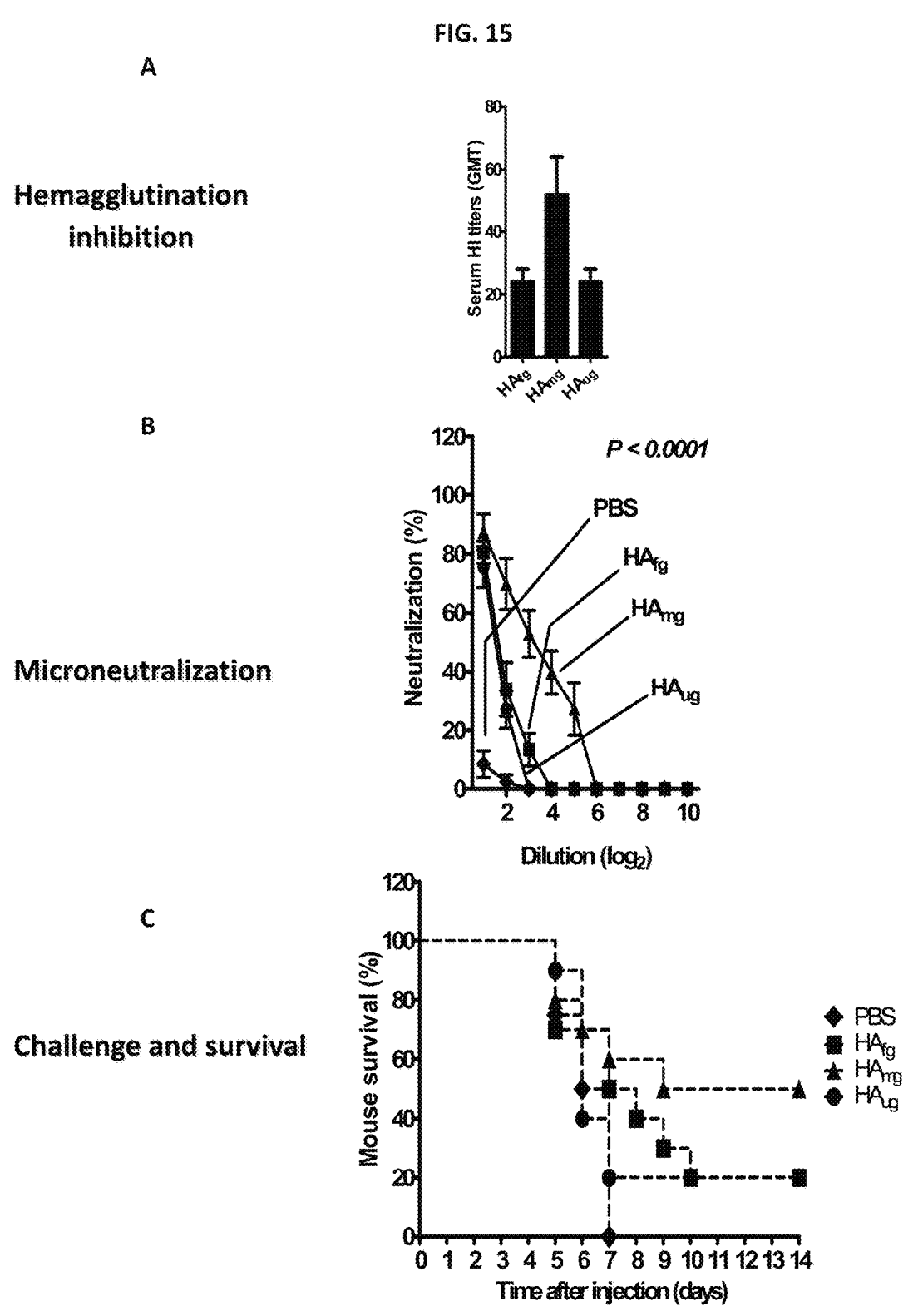

A hemagglutination inhibition assay was used to detect whether antisera from H1 (Brisbane) vaccination can inhibit NIBRG-121 (Pandemic 2009 A(H1N1) vaccine strain) virus's ability to agglutinate Red Blood cells. As shown in FIG. 15, panel A, antisera from vaccination with mono-glycosylated HA ($HA_{mg}$) from H1 (Brisbane) demonstrated better ability to inhibit the NIBRG-121 (H1N1/2009) virus's ability to agglutinate Red Blood Cells than fully glycosylated HA ($HA_{fg}$) and unglycosylated HA ($HA_{ug}$).

A microneutralization assay was used to detect whether antisera from H1 (Brisbane) vaccination can neutralize NIBRG-121 (Pandemic 2009 A(H1N1) vaccine strain) virus's ability to infect MDCK cells. As shown in FIG. 15, panel B, mono-glycosylated HA ($HA_{mg}$) from H1 (Brisbane) demonstrated better ability to neutralize NIBRG-121 (H1N1/2009) virus's ability to infect MDCK cells than fully glycosylated HA ($HA_{fg}$) and unglycosylated HA ($HA_{ug}$).

A virus challenge experiment was conducted to demonstrate vaccination with mono-glycosylated HA from H1 (Brisbane) can protect NIBRG-121 (Pandemic 2009 A(H1N1) vaccine strain) virus challenge. As shown in FIG. 15, panel C, mono-glycosylated HA (Brisbane) as a vaccine protects BALB/c mice from NIBRG-121 (Pandemic 2009 A(H1N1) vaccine strain) virus challenge. In contrast, fully glycosylated HA, which is present in traditional flu vaccines made from inactivated viruses, reveals no cross-protective ability against H1N1 (Pandemic 2009 A(H1N1) vaccine strain) virus infection.

Figure 16:
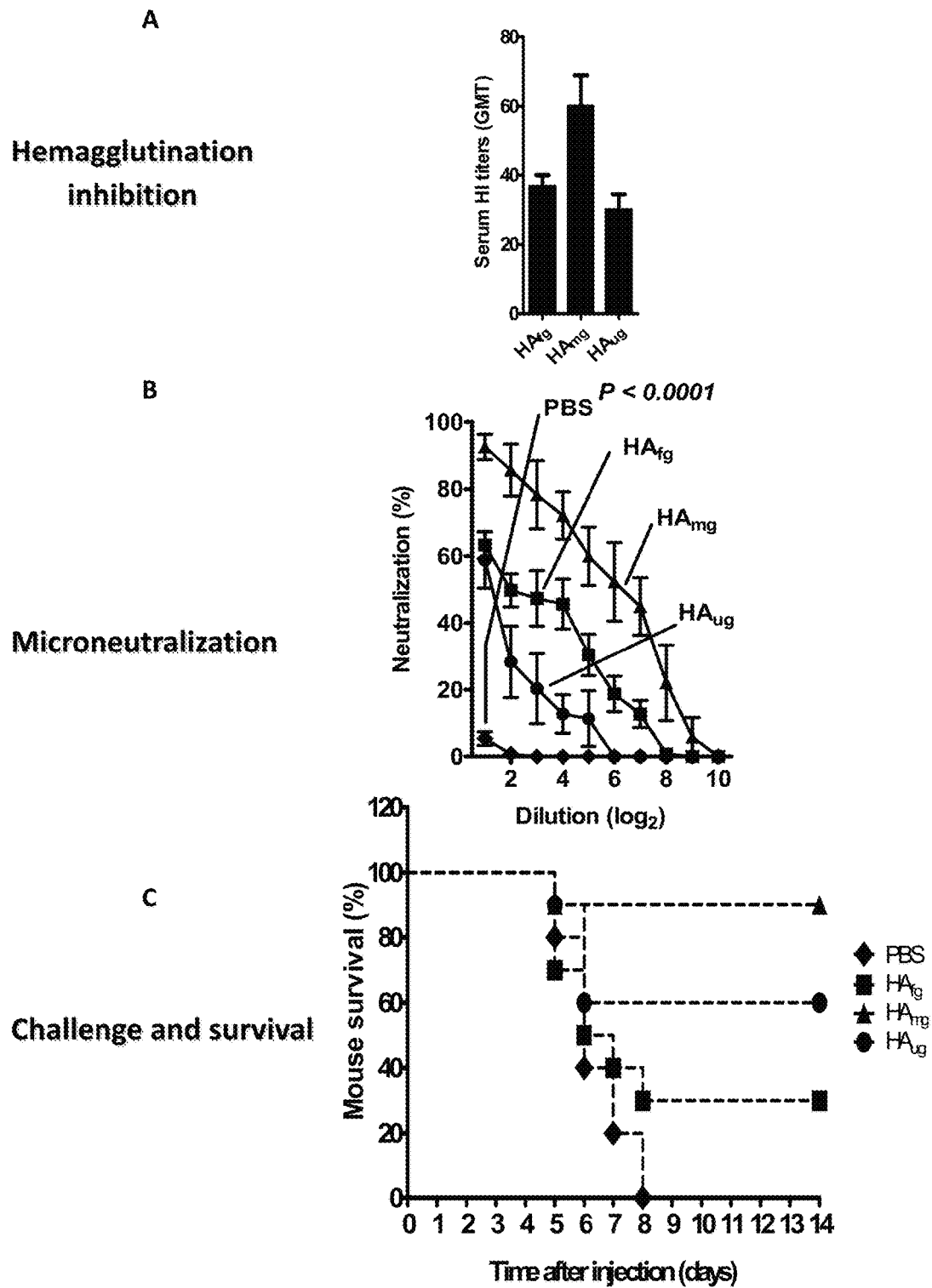
FIG. 16 shows the inhibition of WSN (H1N1) 1933 by antisera generated using mono-glycosylated H1 (Brisbane) HA as antigen. Panel A: inhibition of the ability of the WSN (H1N1) 1933 virus to agglutinate red blood cells. Panel B: inhibition of the ability of the WSN (H1N1) 1933 virus to infect MDCK cells. Panel C: protection of BALB/c mice from infection by WSN (H1N1) 1933 influenza virus. The antisera used was mice immunized with Brisbane HA proteins (5 μg) and the virus used for challenge was WSN (H1N1) 1933 (100×$LD_{50}$)

FIG. 16, panels A-C, shows inhibition of WSN (H1N1) 1933 by antisera generated using mono-glycosylated H1 (Brisbane) HA as antigen. FIG. 16, panel A shows inhibition of the ability of the WSN (H1N1) 1933 virus to agglutinate red blood cells. FIG. 16, panel B shows inhibition of the ability of the WSN (H1N1) 1933 virus to infect MDCK cells. FIG. 16, panel C shows protection of BALB/c mice from infection by WSN (H1N1) 1933 influenza virus. The antisera used was mice immunized with Brisbane HA proteins (5 µg) and the virus used for challenge was WSN (H1N1) 1933 (100×$LD_{50}$).

As shown in FIG. 16, panel A, antisera from vaccination with mono-glycosylated HA ($HA_{mg}$) from H1 (Brisbane) demonstrated better ability to inhibit the WSN (H1N1) 1933 virus' ability to agglutinate Red Blood Cells than fully glycosylated HA ($HA_{fg}$) and unglycosylated HA ($HA_{ug}$). As shown in FIG. 16, panel B, mono-glycosylated HA ($HA_{mg}$) from H1 (Brisbane) demonstrated better ability to neutralize WSN (H1N1) 1933 virus' ability to infect MDCK cells than fully glycosylated HA ($HA_{fg}$) and unglycosylated HA ($HA_{ug}$). As shown in FIG. 16, panel C, mono-glycosylated HA (Brisbane) as a vaccine protects BALB/c mice from WSN (H1N1) 1933 virus challenge. In contrast, fully glycosylated HA, which is present in traditional flu vaccines made from inactivated viruses, reveals no cross-protective ability against WSN (H1N1) 1933 virus infection.

Figure 17:
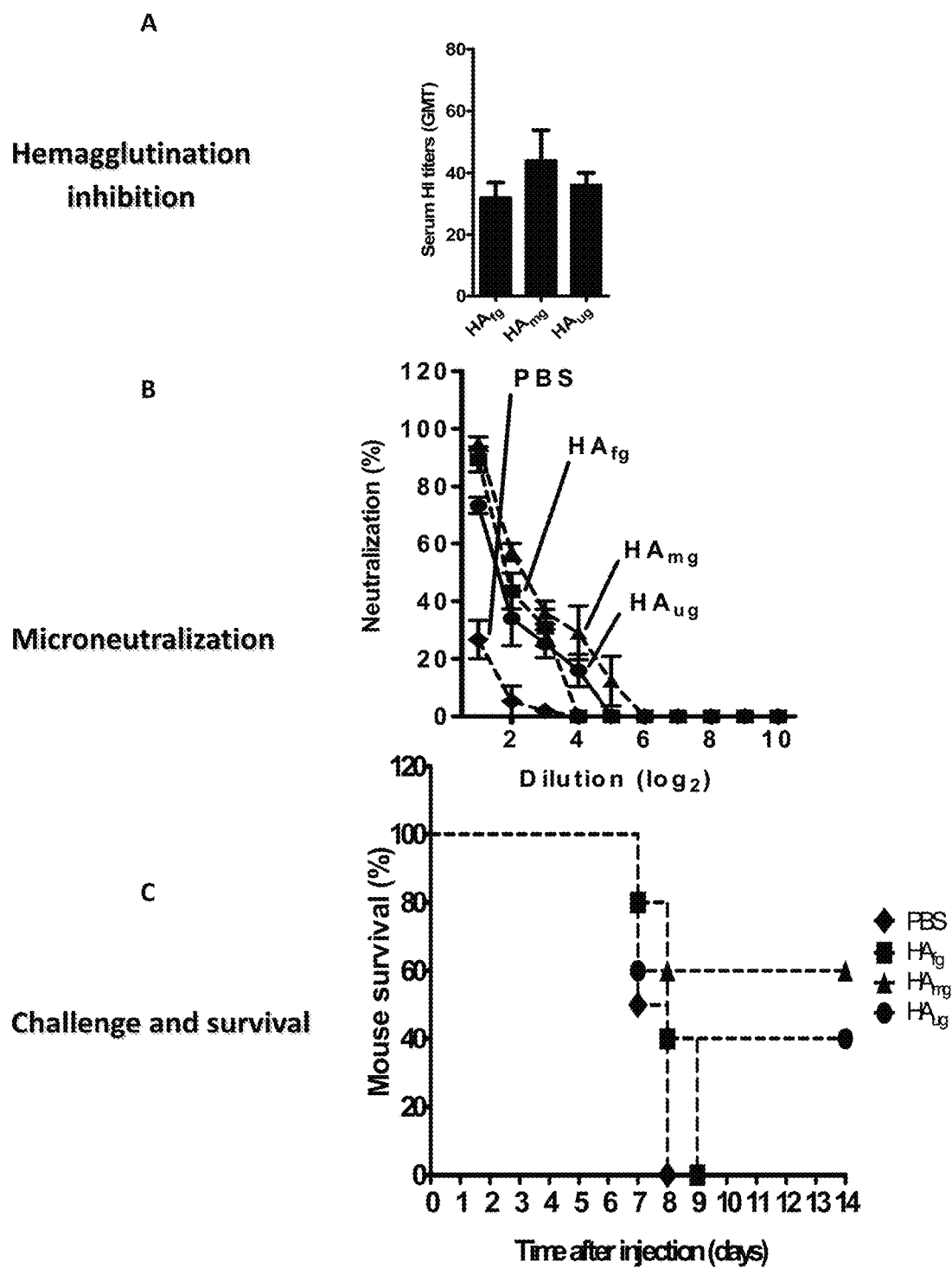
FIG. 17 shows the inhibition of A/Puerto Rico/8/34 (H1N1): PR8 by antisera generated using mono-glycosylated H1 (Brisbane) HA as antigen. Panel A: inhibition of the ability of the PR8 virus to agglutinate red blood cells. Panel B: inhibition of the ability of the PR8 virus to infect MDCK cells. Panel C: protection of BALB/c mice from infection by PR8 influenza virus. The antisera used was mice immunized with Brisbane HA proteins (5 μg) and the virus used for challenge was PR8 (100×$LD_{50}$)

FIG. 17 shows inhibition of A/Puerto Rico/8/34 (H1N1): PR8 by antisera generated using mono-glycosylated H1 (Brisbane) HA as antigen. FIG. 17, panel A shows inhibition of the ability of the PR8 virus to agglutinate red blood cells. FIG. 17, panel B shows inhibition of the ability of the PR8 virus to infect MDCK cells. FIG. 17, panel C shows protection of BALB/c mice from infection by PR8 influenza virus. The antisera used was mice immunized with Brisbane HA proteins (5 µg) and the virus used for challenge was PR8 (100×$LD_{50}$)

As shown in FIG. 17, panel A, antisera from vaccination with mono-glycosylated HA ($HA_{mg}$) from H1 (Brisbane) demonstrated better ability to inhibit the PR8 virus' ability to agglutinate Red Blood Cells than fully glycosylated HA ($HA_{fg}$) and unglycosylated HA ($HA_{ug}$). As shown in FIG. 17, panel B, mono-glycosylated HA ($HA_{mg}$) from H1 (Brisbane) demonstrated better ability to neutralize PR8 virus' ability to infect MDCK cells than fully glycosylated HA ($HA_{fg}$) and unglycosylated HA ($HA_{ug}$). As shown in FIG. 17, panel C, mono-glycosylated HA (Brisbane) as a vaccine protects BALB/c mice from PR8virus challenge. In contrast, fully glycosylated HA, which is present in traditional flu vaccines made from inactivated viruses, reveals no cross-protective ability against PR8 virus infection.

(B) Vaccination with New H1 (Pandemic 2009 a(H1N1) Vaccine Strain) Mono-Glycosylated HA Protein.

The influenza H1 (Pandemic 2009 A(H1N1) vaccine strain) HA coding sequence was isolated and modified for expression as described in Example 1. Table 3 shows the sequence of the modified Pandemic 2009 A(H1N1) vaccine strain H1/HA del-TM-FH6 where the signal peptide sequence is underlined and in bold, the thrombin cleavage site is in italics, the bacteriophage T4 fibritin foldon trimerization sequence and the His-tag is underlined, and the linker sequence is in bold and is underlined.

TABLE 3

Influenza H1 (Pandemic 2009 A(H1N1) vaccine strain) hemagglutinin sequence

| Amino acid sequence of influenza H1 (Pandemic 2009 A(H1N1) vaccine strain) HA del-TM-FH6 | |
|---|---|
| MKAILVVLLYTFATANADTLCIGYHANNSTDTVDTVLEKNVTVTHSVNLL | 50 |
| EDKHNGKLCKLRGVAPLHLGKCNIAGWILGNPECESLSTASSWSYIVETP | 100 |
| SSDNGTCYPGDFIDYEELREQLSSVSSFERFEIFPKTSSWPNHDSNKGVT | 150 |
| AACPHAGAKSFYKNLIWLVKKGNSYPKLSKSYINDKGKEVLVLWGIHHPS | 200 |
| TSADQQSLYQNADAYVFVGSSRYSKKFKPEIAIRPKVRDQEGRMNYYWTL | 250 |
| VEPGDKITFEATGNLVVPRYAFAMERNAGSGIIISDTPVHDCNTTCQTPK | 300 |
| GAINTSLPFQNIHPITIGKCPKYVKSTKLRLATGLRNIPSIQSRGLFGAI | 350 |
| AGFIEGGWTGMVDGWYGYHHQNEQGSGYAADLKSTQNAIDEITNKVNSVI | 400 |

TABLE 3-continued

Influenza H1 (Pandemic 2009 A(H1N1) vaccine strain) hemagglutinin sequence

EKMNTQFTAVGKEFNHLEKRIENLNKKVDDGFLDIWTYNAELLVLLENER  450

TLDYHDSNVKNLYEKVRSQLKNNAKEIGNGCFEFYHKCDNTCMESVKNGT  500

YDYPKYSEEAKLNREEIDGVDIRSLVPRGSPGSGYIPEAPRDGQAYVRKD  550

GEWVLLSTFLGHHHHHH
(SEQ ID NO: 6)

Nucleotide sequence of influenza H1 (Pandemic 2009 A(H1N1) vaccine strain) HA del-TM-FH6

```
   1 ATGGCGCGCC GCTAGCATGA AGGCCATCCT GGTTGTGCTG CTGTACACCT
  51 TCGCTACCGC CAACGCCGAT ACCCTGTGCA TCGGCTACCA CGCCAACAAC
 101 AGCACCGACA CCGTGGATAC CGTGCTGGAA AAGAACGTGA CCGTGACCCA
 151 CAGCGTGAAC CTGCTGGAAG ATAAGCACAA CGGCAAGCTG TGCAAGCTGA
 201 GAGGCGTGGC CCCTCTGCAC CTGGGCAAGT GCAATATCGC CGGCTGGATC
 251 CTGGGCAACC CCGAGTGCGA GAGCCTGAGC ACCGCCAGCA GCTGGTCCTA
 301 CATCGTGGAG ACACCCAGCA GCGACAATGG CACCTGTTAC CCCGGCGACT
 351 TCATCGACTA CGAGGAACTG CGGGAGCAGC TGAGCAGCGT GTCCAGCTTC
 401 GAGCGGTTCG AGATCTTCCC CAAGACCAGC TCTTGGCCCA ACCACGACAG
 451 CAACAAGGGC GTGACCGCCG CCTGTCCTCA CGCTGGCGCC AAGAGCTTCT
 501 ACAAGAACCT GATCTGGCTG GTCAAGAAGG CAACAGCTA CCCCAAACTG
 551 AGCAAGAGCT ACATCAACGA CAAGGGCAAA GAAGTGCTGG TGCTGTGGGG
 601 CATCCACCAC CCTAGCACCA GCGCCGACCA GCAGAGCCTG TACCAGAACG
 651 CCGACGCCTA CGTGTTCGTG GGCAGCAGCC GGTACAGCAA GAAGTTCAAG
 701 CCCGAGATCG CCATCAGACC CAAAGTGCGG GACCAAGAGG GCCGGATGAA
 751 CTACTACTGG ACCCTGGTGG AGCCCGGCGA CAAGATCACC TTCGAGGCCA
 801 CCGGCAATCT GGTCGTGCCC AGATACGCCT TCGCCATGGA AAGAAACGCC
 851 GGCAGCGGCA TCATCATCAG CGACACCCCC GTGCACGACT GCAACACCAC
 901 CTGTCAGACC CCCAAAGGCG CCATCAACAC CAGCCTGCCC TTCCAGAACA
 951 TCCACCCCAT CACCATCGGC AAGTGCCCTA AGTACGTGAA GTCTACCAAG
1001 CTGAGGCTGG CCACAGGCCT GCGGAACATC CCCAGCATCC AGAGCAGAGG
1051 CCTGTTTGGC GCCATTGCCG GCTTTATCGA GGGCGGCTGG ACCGGAATGG
1101 TGGATGGATG GTATGGCTAC CACCACCAGA ATGAGCAGGG AAGCGGCTAC
1151 GCCGCCGACC TGAAGTCCAC ACAGAACGCC ATCGACGAGA TCACCAACAA
1201 AGTGAACTCA GTGATCGAGA AGATGAACAC CCAGTTCACC GCCGTGGGCA
1251 AAGAATTCAA CCACCTGGAA AAGCGGATCG AGAACCTGAA CAAGAAGGTG
1301 GACGACGGCT TCCTGGACAT CTGGACCTAC AACGCCGAGC TGCTCGTGCT
1351 GCTGGAAAAC GAGCGGACCC TGGACTACCA CGACTCCAAC GTGAAGAATC
1401 TGTACGAGAA AGTTCGCTCC CAGCTGAAGA ACAACGCCAA AGAGATCGGC
1451 AACGGCTGCT TCGAGTTCTA CCACAAGTGC GACAACACCT GTATGGAAAG
1501 CGTGAAGAAC GGCACCTACG ACTACCCCAA GTACAGCGAG GAAGCCAAGC
1551 TGAACCGGGA AGAGATCGAC GGCGTGGATA TCAGATCTCT GGTGCCAAGA
1601 GGATCTCCAG GATCTGGATA CATCCCAGAG GCTCCAAGAG ATGGACAAGC
```

TABLE 3-continued

Influenza H1 (Pandemic 2009 A(H1N1) vaccine strain) hemagglutinin sequence

```
1651 TTACGTGAGA AAGGACGGAG AGTGGGTGCT GCTGTCTACT TTCCTGGGAC

1701 ACCACCACCA CCACCACTAA
(SEQ ID NO: 7)
```

A hemagglutination inhibition assay was used to detect whether antisera from H1 (Pandemic 2009 A(H1N1) vaccine strain) vaccination can inhibit WSN (H1N1) virus's ability to agglutinate Red Blood cells. As shown in FIG. 18, panel A, antisera from vaccination with mono-glycosylated HA ($HA_{mg}$) from H1 (Pandemic 2009 A(H1N1) vaccine strain) demonstrated better ability to inhibit the WSN (H1N1) virus's ability to agglutinate Red Blood Cells than fully glycosylated HA ($HA_{fg}$) and unglycosylated HA ($HA_{ug}$).

A microneutralization assay was used to detect whether antisera from H1 (Pandemic 2009 A(H1N1) vaccine strain) vaccination can neutralize WSN (H1N1) virus's ability to infect MDCK cells. As shown in FIG. 18, panel B, mono-glycosylated HA ($HA_{mg}$) from H1 (Pandemic 2009 A(H1N1) vaccine strain) demonstrated better ability to neutralize WSN (H1N1) virus's ability to infect MDCK cells than fully glycosylated HA ($HA_{fg}$) and unglycosylated HA ($HA_{ug}$).

A virus challenge experiment is used to demonstrate vaccination with mono-glycosylated HA from H1 (Pandemic 2009 A(H1N1) vaccine strain) can protect from WSN (H1N1) 1933 or A/Puerto Rico/8/34 (H1N1): PR8 virus challenge. Mono-glycosylated HA (Pandemic 2009 A(H1N1) vaccine strain) as a vaccine protects BALB/c mice from WSN (H1N1) or PR8 virus challenge. In contrast, fully glycosylated HA, which is present in traditional flu vaccines made from inactivated viruses, reveals no cross-protective ability against WSN (H1N1) or PR8 virus infection.

Partially glycosylated (e.g., mono-glycosylated) HA from other strains of influenza virus also can be used to formulate potent vaccines active in preventing or reducing infections by one or more strains or subtypes of influenza virus. The influenza HA coding sequence from any number can be isolated and modified for expression as described in Example 1. The HA is then cloned and expressed in an eukaryotic expression system and then subjected to degly-cosylation to retain one to three glycosylations (preferably mono-glycosylated) at a glycosylation site.

Table 4 shows the consensus sequence of the modified H1 A del-TM-FH6 where the signal peptide sequence is underlined and in bold, the thrombin cleavage site is in italics, the bacteriophage T4 fibritin foldon trimerization sequence and the His-tag is underlined, and the linker sequence is in bold and is underlined.

TABLE 4

Consensus H1 A del-TM-FH6 hemagglutinin sequence

Consensus amino acid sequence of influenza H1 A del-TM-FH6 hemagglutinin

```
MKVKLLVLLCTFTATYADTICIGYHANNSTDTVDTVLEKNVTVTHSVNLL      50

EDSHNGKLCLLKGIAPLQLGNCSVAGWILGNPECELLISKESWSYIVETP     100

NPENGTCYPGYFADYEELREQLSSVSSFERFEIFPKESSWPNHTVTKGVS     150

ASCSHNGKSSFYRNLLWLTGKNGLYPNLSKSYANNKEKEVLVLWGVHHPP     200

NIGDQRALYHTENAYVSVVSSHYSRRFTPEIAKRPKVRDQEGRINYYWTL     250

LEPGDTIIFEANGNLIAPRYAFALSRGFGSGIITSNAPMDECDAKCQTPQ     300

GAINSSLPFQNVHPVTIGECPKYVRSTKLRMVTGLRNIPSIQSRGLFGAI     350

AGFIEGGWTGMVDGWYGYHHQNEQGSGYAADQKSTQNAINGITNKVNSVI     400

EKMNTQFTAVGKEFNKLERRMENLNKKVDDGFLDIWTYNAELLVLLENER     450

TLDFHDSNVKNLYEKVKSQLKNNAKEIGNGCFEFYHKCNDECMESVKNGT     500

YDYPKYSEESKLNREKIDGVDIRSLVPRGSPGSGYIPEAPRDGQAYVRKD     550

GEWVLLSTFLGHHHHHH (SEQ ID NO: 8)
```

Nucleotide sequence of influenza H1 A del-TM-FH6 hemagglutinin

```
  1 ATGAAGGTGA AACTGCTGGT GCTGCTGTGC ACCTTCACCG CCACCTACGC

51 CGACACCATC TGCATCGGCT ACCACGCCAA CAACAGCACC GACACCGTGG

101 ATACCGTGCT GGAAAAGAAC GTGACCGTGA CCCACAGCGT GAACCTGCTG

151 GAAGATAGCC ACAACGGCAA GCTGTGCCTG CTGAAGGGCA TTGCCCCCCT

201 GCAGCTGGGC AACTGTAGCG TGGCCGGCTG GATTCTGGGC AACCCCGAGT
```

TABLE 4-continued

Consensus H1 A del-TM-FH6 hemagglutinin sequence

```
 251 GCGAGCTGCT GATCAGCAAA GAGTCCTGGT CCTACATCGT GGAGACACCC
 301 AACCCCGAGA ACGGCACCTG TTACCCCGGC TACTTCGCCG ACTACGAGGA
 351 ACTGAGAGAG CAGCTGTCCT CTGTCTCCAG CTTCGAGCGG TTCGAGATCT
 401 TCCCCAAAGA GAGCAGCTGG CCCAACCACA CCGTGACAAA GGGCGTGAGC
 451 GCCAGCTGCT CCCACAATGG CAAGAGCAGC TTCTACCGGA ACCTGCTGTG
 501 GCTGACCGGC AAGAACGGCC TGTACCCCAA CCTGAGCAAG AGCTATGCCA
 551 ACAACAAAGA GAAAGAGGTC CTCGTCCTCT GGGGCGTGCA CCACCCCCCC
 601 AACATCGGCG ACCAGCGGGC CCTGTACCAC ACCGAGAACG CCTACGTGTC
 651 CGTGGTGTCC AGCCACTACA GCAGACGGTT CACCCCCGAG ATCGCCAAGA
 701 GGCCCAAAGT GCGGGACCAG GAAGGCCGGA TCAACTACTA CTGGACCCTG
 751 CTGGAACCCG GCGACACCAT CATCTTCGAG GCCAACGGCA ACCTGATCGC
 801 CCCCAGATAC GCCTTTGCCC TGAGCAGAGG CTTCGGCAGC GGCATCATCA
 851 CCAGCAACGC CCCCATGGAC GAGTGCGACG CCAAGTGTCA GACCCCCCAG
 901 GGCGCCATCA ACAGCAGCCT GCCCTTCCAG AACGTGCACC CCGTGACCAT
 951 CGGCGAGTGC CCTAAGTACG TGCGGAGCAC CAAGCTGAGA ATGGTGACCG
1001 GCCTGCGGAA CATCCCCAGC ATCCAGAGCA GAGGCCTGTT TGGCGCCATT
1051 GCCGGCTTTA TCGAGGGCGG CTGGACCGGA ATGGTGGACG GGTGGTACGG
1101 CTACCACCAC CAGAATGAGC AGGGCAGCGG CTACGCCGCC GATCAGAAGT
1151 CCACCCAGAA CGCTATCAAC GGCATCACCA ACAAAGTGAA CAGCGTGATC
1201 GAGAAGATGA ACACCCAGTT CACCGCCGTG GGCAAAGAGT TCAACAAGCT
1251 GGAACGGCGG ATGGAAAACC TGAACAAGAA GGTGGACGAC GGCTTCCTGG
1301 ACATCTGGAC CTACAACGCC GAGCTGCTGG TCCTGCTGGA AAACGAGCGG
1351 ACCCTGGACT TCCACGACAG CAACGTGAAG AACCTGTACG AGAAAGTGAA
1401 GTCCCAGCTG AAGAACAACG CCAAAGAGAT CGGCAACGGC TGCTTCGAGT
1451 TCTACCACAA GTGCAACGAC GAGTGCATGG AAAGCGTGAA GAACGGCACA
1501 TACGACTACC CCAAGTACAG CGAGGAAAGC AAGCTGAACC GGGAGAAGAT
1551 CGACGGCGTG GATATCAGAT CTCTGGTGCC AAGAGGATCT CCAGGATCTG
1601 GATACATCCC AGAGGCTCCA AGAGATGGAC AAGCTTACGT GAGAAAGGAC
1651 GGAGAGTGGG TGCTGCTGTC TACTTTCCTG GACACCACC ACCACCACCA
1701 CTAA (SEQ ID NO: 9)
```

Table 5 shows the consensus sequence of the modified H1-C del-TM-FH6 where the signal peptide sequence is underlined and in bold, the thrombin cleavage site is in italics, the bacteriophage T4 fibritin foldon trimerization sequence and the His-tag is underlined, and the linker sequence is in bold and is underlined.

TABLE 5

Consensus H1-C del-TM-FH6 hemagglutinin sequence

Consensus amino acid sequence of influenza H1-C del-TM-FH6 hemagglutinin

```
MKVKLLVLLCTFTATYADTICIGYHANNSTDTVDTVLEKNVTVTHSVNLL        50

EDSHNGKLCLLKGIAPLQLGNCSVAGWILGNPECELLISKESWSYIVETP       100

NPENGTCYPGHFADYEELREQLSSVSSFERFEIFPKESSWPNHDTVTGVS       150
```

TABLE 5-continued

Consensus H1-C del-TM-FH6 hemagglutinin sequence

ASCSHNGESSFYRNLLWLTGKNGLYPNLSKSYANNKEKEVLVLWGVHHPP    200

NIGDQKALYHTENAYVSVVSSHYSRKFTPEIAKRPKVRDQEGRINYYWTL    250

LEPGDTIIFEANGNLIAPRYAFALSRGFGSGIINSNAPMDKCDAKCQTPQ    300

GAINSSLPFQNVHPVTIGECPKYVRSAKLRMVTGLRNIPSIQSRGLFGAI    350

AGFIEGGWTGMVDGWYGYHHQNEQGSGYAADQKSTQNAINGITNKVNSVI    400

EKMNTQFTAVGKEFNKLERRMENLNKKVDDGFLDIWTYNAELLVLLENER    450

TLDFHDSNVKNLYEKVKSQLKNNAKEIGNGCFEFYHKCNDECMESVKNGT    500

YDYPKYSEESKLNREKIDGVDIRSLVPRGSPGSGYIPEAPRDGQAYVRKD    550

GEWVLLSTFLGHHHHHH (SEQ ID NO: 10)

Nucleotide sequence of influenza H1-C del-TM-FH6 hemagglutinin
```
   1   ATGAAGGTGA AACTGCTGGT GCTGCTGTGC ACCTTCACCG CCACCTACGC
  51   CGACACCATC TGCATCGGCT ACCACGCCAA CAACAGCACC GACACCGTGG
 101   ATACCGTGCT GGAAAAGAAC GTGACCGTGA CCCACAGCGT GAACCTGCTG
 151   GAAGATAGCC ACAACGGCAA GCTGTGCCTG CTGAAGGGCA TTGCCCCCCT
 201   GCAGCTGGGC AACTGTAGCG TGGCCGGCTG GATTCTGGGC AACCCCGAGT
 251   GCGAGCTGCT GATCTCCAAA GAGTCCTGGT CTTACATCGT GGAGACACCC
 301   AACCCCGAGA ACGGCACCTG TTACCCCGGC CACTTCGCCG ACTACGAGGA
 351   ACTGCGGGAG CAGCTGAGCA GCGTGTCCAG CTTCGAGCGG TTCGAGATCT
 401   TCCCCAAAGA GAGCAGCTGG CCCAACCACG ATACCGTGAC CGGCGTGAGC
 451   GCCAGCTGTT CCCACAACGG CGAGAGCAGC TTCTACCGGA ACCTGCTGTG
 501   GCTGACCGGC AAGAACGGCC TGTACCCCAA CCTGAGCAAG AGCTATGCCA
 551   ACAACAAAGA GAAGGAAGTC CTGGTCCTCT GGGGCGTGCA CCACCCCCCC
 601   AACATCGGCG ACCAGAAGGC CCTGTACCAC ACCGAGAACG CCTACGTGTC
 651   CGTGGTGTCC AGCCACTACA GCCGGAAGTT CACCCCCGAG ATCGCCAAGA
 701   GGCCCAAAGT GCGGGACCAG GAAGGCCGGA TCAACTACTA CTGGACCCTG
 751   CTGGAACCCG GCGACACCAT CATCTTCGAG GCCAACGGCA ACCTGATCGC
 801   CCCCAGATAC GCCTTTGCCC TGAGCAGAGG CTTCGGCAGC GGCATCATCA
 851   ACAGCAACGC CCCCATGGAC AAGTGCGACG CCAAGTGCCA GACACCCCAG
 901   GGCGCCATCA ACAGCTCCCT GCCCTTCCAG AACGTGCACC CCGTGACCAT
 951   CGGCGAGTGC CCTAAGTACG TGCGGAGCGC CAAGCTGAGA ATGGTGACCG
1001   GCCTGCGGAA CATCCCCAGC ATCCAGAGCA GAGGCCTGTT TGGCGCCATT
1051   GCCGGCTTTA TCGAGGGCGG CTGGACCGGA ATGGTGGACG GGTGGTACGG
1101   CTACCACCAC CAGAATGAGC AGGGCAGCGG CTACGCCGCC GATCAGAAGT
1151   CCACCCAGAA CGCCATCAAC GGCATCACCA ACAAAGTGAA CAGCGTGATC
1201   GAGAAGATGA ACACCCAGTT CACCGCCGTG GGCAAAGAGT TCAACAAGCT
1251   GGAACGGCGG ATGGAAAACC TGAACAAGAA GGTGGACGAC GGCTTCCTGG
1301   ACATCTGGAC CTACAACGCC GAGCTGCTGG TGCTGCTGGA AAACGAGCGG
1351   ACCCTGGACT TCCACGACAG CAACGTGAAG AACCTGTACG AGAAAGTGAA
1401   GTCCCAGCTG AAGAACAACG CCAAAGAGAT CGGCAACGGC TGCTTCGAGT
```

TABLE 5-continued

Consensus H1-C del-TM-FH6 hemagglutinin sequence

```
1451  TCTACCACAA GTGCAACGAC GAGTGCATGG AAAGCGTGAA GAACGGCACA

1501  TACGACTACC CCAAGTACAG CGAGGAAAGC AAGCTGAACC GGGAGAAGAT

1551  CGACGGCGTG GATATCAGAT CTCTGGTGCC AAGAGGATCT CCAGGATCTG

1601  GATACATCCC AGAGGCTCCA AGAGATGGAC AAGCTTACGT GAGAAAGGAC

1651  GGAGAGTGGG TGCTGCTGTC TACTTTCCTG GGACACCACC ACCACCACCA

1701  CTAA (SEQ ID NO: 11)
```

Vaccines generated from the deglycosylated HA peptides of the instant disclosure exhibit antiviral activity against respiratory viruses, including respiratory syncytial virus (RSV) and various types of influenza, such as influenza A and influenza B. Advantageously, the antiviral peptides of the present disclosure exhibit antiviral activity against numerous strains of influenza, including seasonal, avian (e.g., H5N1 strains), and swine influenzas. Illnesses resulting from infections by these viruses can also be prevented or treated according to some of the disclosed methods.

(C) Glycosylation Sites on the H1/HA Protein.

The influenza H1 HA molecules have four distinct antigenic sites: Sa, Sb, Ca, and Cb (Luoh S M, et al. (1992) J Virol 66:1066-1073). These sites consist of the most variable amino acids in the HA molecule of the seasonal human H1N1 viruses that have been subjected to antibody-mediated immune pressure since its emergence in 1918.

Using hemagglutination inhibition (HI) assays and vaccination/challenge studies, it was demonstrated that the 2009 pandemic H1N1 virus is antigenically similar to human H1N1 viruses that circulated from 1918-1943 and to classical swine H1N1 viruses. Antibodies against 1918-like or classical swine H1N1 vaccines were found to completely protect C57B/6 mice from lethal challenge with the influenza A/Netherlands/602/2009 virus isolate. Passive immunization with cross-reactive monoclonal antibodies (mAbs) raised against either 1918 or A/California/04/2009 HA proteins were found to offer full protection from death. Analysis of mAb antibody escape mutants, generated by selection of 2009 H1N1 virus with these mAbs, indicate that antigenic site Sa is one of the conserved cross-protective epitopes. (Manicassamy B., et al. PLoS Pathogens January 2010|Volume 6|Issue 1|e1000745).

Figure 19:
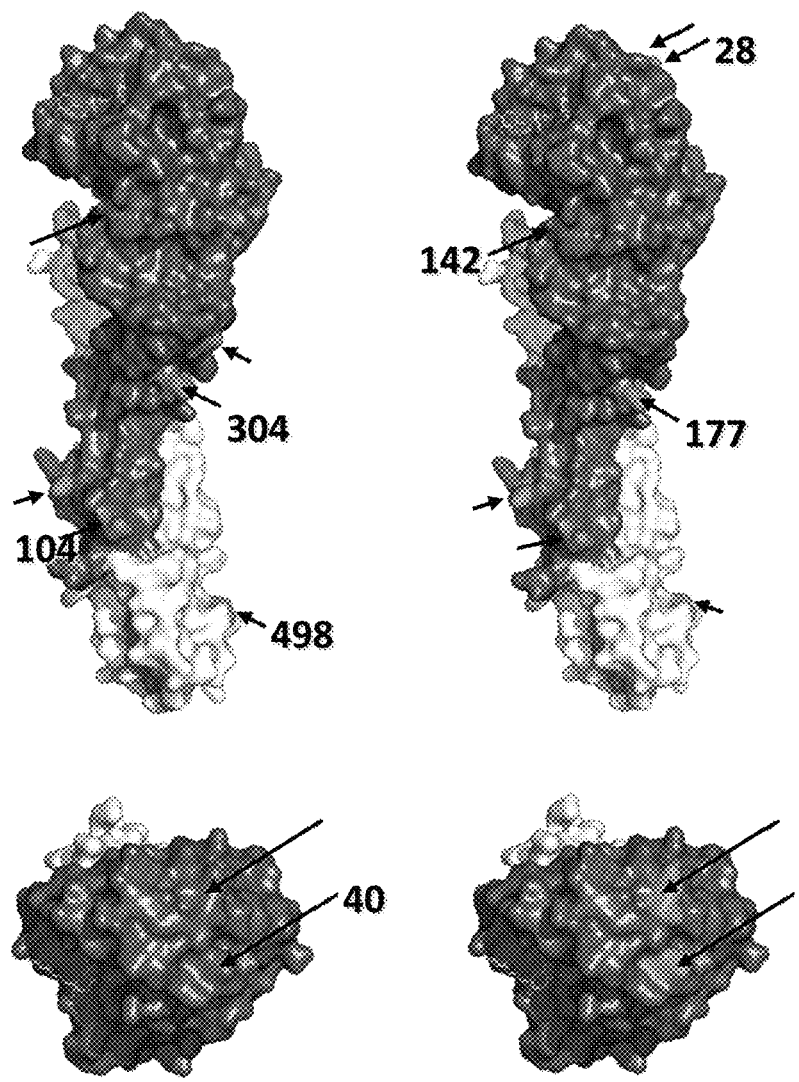
FIG. 19 shows structural comparison of the glycosylation sites on the H1 HA protein.

By homology modeling of the HA structure, it has been shown that HAs of 2009 H1N1 and the 1918 pandemic virus share a significant number of amino acid residues in known antigenic sites, suggesting the existence of common epitopes for neutralizing antibodies cross-reactive to both HAs. (Igarashi M. et al., PLoS ONE January 2010, Volume 5, Issue 1, e8553). A potential glycosylation site exists at the Asn177 residue on HA, which is within the antigenically conserved Sa region. (See FIG. 19). Proteins carrying a mutation at the Asn177 glycosylation site within the HA of Brisbane H1 are used to immunize mice. Cross-protection against NIBRG-121 is measured.

Antisera from vaccination with mono-glycosylated HA ($HA_{mg}$) carrying a mutation at Asn177 from H1 (Brisbane) demonstrates better ability to inhibit the NIBRG-121 virus' ability to agglutinate Red Blood Cells than fully glycosylated HA ($HA_{fg}$) carrying a mutation at Asn177 and unglycosylated HA ($HA_{ug}$) carrying a mutation at Asn177. Mono-glycosylated HA ($HA_{mg}$) carrying a mutation at Asn177 from H1 (Brisbane) demonstrates better ability to neutralize NIBRG-121 virus' ability to infect MDCK cells than fully glycosylated HA ($HA_{fg}$) carrying a mutation at Asn177 and unglycosylated HA ($HA_{ug}$) carrying a mutation at Asn177. Mono-glycosylated HA (Brisbane) as a vaccine protects BALB/c mice from NIBRG-121 virus challenge. In contrast, fully glycosylated HA carrying a mutation at Asn177 reveals little or no cross-protective ability against NIBRG-121 virus infection.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

The "antiviral activity" of a vaccine according the present disclosure denotes the ability of the vaccine to generate an immune response in a subject to whom the vaccine is administered wherein the immune response is sufficient to prevent or treat or ameliorate full blown viral infection and/or symptoms associated with infection by a virus, such as an influenza virus. Advantageously, vaccines generated from the deglycosylated HA peptides of the instant disclosure may demonstrate significant antiviral activity against influenza virus. As used herein, "significant antiviral activity" can be measured by the ability of the vaccine to inhibit viral hemagglutination by at least about 50%, as compared to mock treated samples of virus. In certain embodiments, the antiviral peptide inhibits viral hemagglutination by at least about 60%, more preferably by at least about 70%, more preferably by at least about 80%, more preferably by at least about 90%, and more preferably by at least about 95%, as compared to mock treated samples of virus.

Methods for demonstrating the inhibitory effect of antiviral compositions on viral replication are well known in the art. The therapeutic efficacy of the vaccines of the present invention as antiviral agents can be demonstrated in laboratory animals, for example, by using a murine model. (See e.g., Jones, et al., J. Virol, 2006, Vol. 80, No. 24, pp. 11960-11967). Additionally, the therapeutic effect of the pharmacologically active peptides of the present invention can be shown in humans via techniques known in the art.

The neutralizing antibodies of the present invention can be additionally used as a tool for epitope mapping of antigenic determinants of influenza A virus, and are useful in vaccine development. Indeed, as shown in the Examples below, the inventors herein have identified several broadly reactive neutralizing antibodies that can be used as guides for vaccine design.

Thus, the neutralizing antibodies of the present invention can be used to select peptides or polypeptides that functionally mimic the neutralization epitopes to which the antibodies bind, which, in turn, can be developed into vaccines against influenza A virus infection. In one embodiment, the present invention provides a vaccine effective against an influenza A virus comprising a peptide or polypeptide that functionally mimics a neutralization epitope bound by an antibody described herein. In one embodiment, the vaccine comprises a peptide or polypeptide functionally mimicking a neutralization epitope bound by an antibody that binds a hemagglutinin (HA) antigen. In another embodiment, the vaccine may be synthetic. In other embodiments, the vaccine may comprise (i) an attenuated influenza A virus, or a part thereof; or (ii) a killed influenza A virus, or part thereof. In one other embodiment, the vaccine comprises a peptide or polypeptide functionally mimicking a neutralization epitope bound by an antibody that binds a hemagglutinin (HA) antigen. The HA antigen may be an H5 subtype or an H1 subtype. In another embodiment, the HA antigen is displayed on the surface of an influenza A virus.

Influenza Virus Vaccines

The N-glycosylation site sequences of influenza H5 HA are highly conserved. The H5 HA has 15 total N-glycosylation sites having the prototypic sequence N-X-(S/T). Each monomer has 5 N-glycosylation sites at positions N27, N39, N170, N181 and N500. Host receptor binding is affected by glycans on HA structure. H5 HA has glycosylation sites at positions 39, 127, 170, 181, and 500.

The vaccines of the invention can be generated using partially glycosylated versions of any surface protein of influenza virus, including HA, NA and M2. The influenza A virus neuraminidase (NA) proteins are displayed on their surface. The influenza A virus M2 protein is an integral membrane protein of 97 amino acids that is expressed at the surface of infected cells with an extracellular N-terminal domain of 18 to 23 amino acid residues, an internal hydrophobic domain of approximately 19 residues, and a C-terminal cytoplasmic domain of 54 residues. (Zebedee S L, et al. J. Virol. 1988 August; 62(8):2762-2772).

Further, the partially glycosylated influenza proteins may be generated by altering the glycosylation pattern at N- or O-glycosylation sites of the protein used as an antigen.

In another embodiment, the peptides or polypeptides of the vaccine contain antigenic determinants that raise influenza A virus neutralizing antibodies.

In a more general aspect, the neutralizing molecules, including but not limited to antibodies, are useful to prevent or treat viral infections. Thus, the neutralizing molecules of the present invention are useful in immunotherapy, such as passive immunization using one or more such molecules, and in the development of vaccines directed at the viral antigenic target(s).

The present provides vaccine compositions for the prevention and treatment of infections caused by the avian influenza neutralized virus. While it has been known for over 80 years that passive administration of immune sera can prevent infection Luke, T. C. et al., Kilbane E M, Jackson J L, & Hoffman S L (2006) Ann Intern Med 145, 599-609), more recent studies with monoclonal antibodies also offer encouragement (Hanson, B. J. et al. (2006) Respir Res 7, 126; Huang, C. C. et al. (2004) Proc. Nat. Acad. Sci. 101, 2706-2711; Simmons C. P. et al. (2007) PLoS Med 4, e178). For example, Hanson et al. showed that a monoclonal antibody to H5N1 virus was protective against lethal infection, even when given three days post inoculation in mice (Hanson, B. J. et al. (2006) Respir Res 7, 126).

Given the possibility of a catastrophic epidemic, it has been suggested that governments should maintain stocks of neutralizing antibodies such as those reported here. The facts that antibodies are fully human and have been isolated from individuals who successfully combated viral infection may offer advantages. However, even if such antibodies are stockpiled, if the gene encoding the epitope to which the antibody binds were to mutate, then the antibody might be less effective. Also, there is some evidence that cellular immunity enhances clearance of the virus. Nevertheless, if the only effect of passive immunization was to lessen the severity of infection, thereby giving the necessary time for other immune effectors to operate, it could be of critical importance for lessening mortality in patients with weakened immune, cardiovascular, and respiratory systems and in the elderly. Passive immunization might prevent cytokine storm against rapidly proliferating viruses, as occurred even in healthy young adults during the 1918 influenza outbreak.

Respiratory Syncytial Virus (RSV) Vaccines

Human respiratory syncytial virus (RSV) is a virus that causes respiratory tract infections. It is the major cause of lower respiratory tract infection and hospital visits during infancy and childhood. RSV is an enveloped RNA virus of the family Paramyxoviridae and of the genus Pneumovirus. There is no vaccine.

The RSV virion comprises three surface glycoproteins, three surface glycoproteins, F, G and SH (small hydrophobic). F proteins on the surface of the virus cause the cell membranes on nearby cells to merge, forming syncytia. F (fusion) and G (attachment) glycoproteins are required for viral entry into cells and they also determine the antibody response. The structure and composition of RSV has been elucidated and is described in detail in the textbook "Fields Virology", ed. Knipe, D. M. et al., Lippincott Williams & Wilkins, NY (2001), in particular, Chapter 45, pp. 1443-1485, "Respiratory Syncytial Virus" by Collins, P., Chanock, R. M. and Murphy, B. R.

RSV G protein, which is 33 kDa unglycosylated, runs at approximately 90 kDa when fully glycosylated (both N- and O-linked glycosylations). F and G proteins exist as a protein complex on the surface of RSV-infected cells. (Low K-W et al. Biochem. Biophys. Res. Comm. 366(2) 2008, 308-313).

Table 6 indicates the sequence of the RSV glycoprotein G with potential N-glycosylation sites underlined.

TABLE 6

RSV glycoprotein G polypeptide sequence.

```
MSKNKDQRTT KTLEKTWDTL NHLLFISSCL YKLNLKSIAQ ITLSILAMII STSLIIAAII  60

FIASANHKVT LTTAIIQDAT SQIKNTTPTY LTQNPQLGIS FSNLSETTSQ TTTILASTTP 120

SVKSTLQSTT VKTKNTTTTK IQPSKPTTKQ RQNKPPNKPN NDFHFEVFNF VPCSICSNNP 180

TCWAICKRIP NKKPGKKTTT KPTKKPTIKT TKKDLKPQTT KPKEVPTTKP TEKPTINTTK 240

TNIRTTLLTN NTTGNPEHTS QKGTLHSTSS DGNPSPSQVY TTSEYLSQPP SPSNTTNQ   298
(SEQ ID NO: 12)
```

Partially deglycosylated RSV glycoproteins F and G could be useful as more effective RSV vaccines.

Flavivirus Vaccines

Flavivirus is a genus of the family Flaviviridae. Flaviviruses are small, enveloped RNA viruses that use arthropods such as mosquitoes for transmission to their vertebrate hosts, and include Yellow fever virus (YFV), West Nile virus (WNV), Tick-borne encephalitis virus, Japanese encephalitis virus (JE) and Dengue virus 2 viruses (Weaver S C, Barrett A D Nat. Rev. Microbiol. 2 789-801 2004). Flaviviruses consist of three structural proteins: the core nucleocapsid protein C, and the envelope glycoproteins M and E. Glycoprotein E is a class II viral fusion protein that mediates both receptor binding and fusion. Class II viral fusion proteins are found in flaviviruses and alphaviruses.

Glycoprotein E is comprised of three domains: domain I (dimerisation domain) is an 8-stranded beta barrel, domain II (central domain) is an elongated domain composed of twelve beta strands and two alpha helices, and domain III (immunoglobulin-like domain) is an IgC-like module with ten beta strands. Domains I and II are intertwined.

The 495 AA glycoprotein E dimers on the viral surface re-cluster irreversibly into fusion-competent trimers upon exposure to low pH, as found in the acidic environment of the endosome. The formation of trimers results in a conformational change that results in the exposure of a fusion peptide loop at the tip of domain II, which is required in the fusion step to drive the cellular and viral membranes together by inserting into the membrane (Modis Y et al., Proc. Natl. Acad. Sci. U.S.A. 100 6986-91 2003).

Dengue virus envelope protein (E) contains two major N-linked glycosylation sites, at Asn-67 and Asn-153. The glycosylation site at position 153 is conserved in most flaviviruses, while the site at position 67 is thought to be unique for dengue viruses. N-linked oligosaccharide side chains on flavivirus E proteins have been associated with viral morphogenesis, infectivity, and tropism. Dengue viruses lacking N-glycosylation at position 67 show reduced infection of human cells. (Mondotte J A, et al., *J. Virol.* 81(3):7136-7148 (2007).

Table 7 indicates the sequence of the Dengue virus glycoprotein E with potential N-glycosylation sites at N-67 and N-153 underlined.

Figure 21:
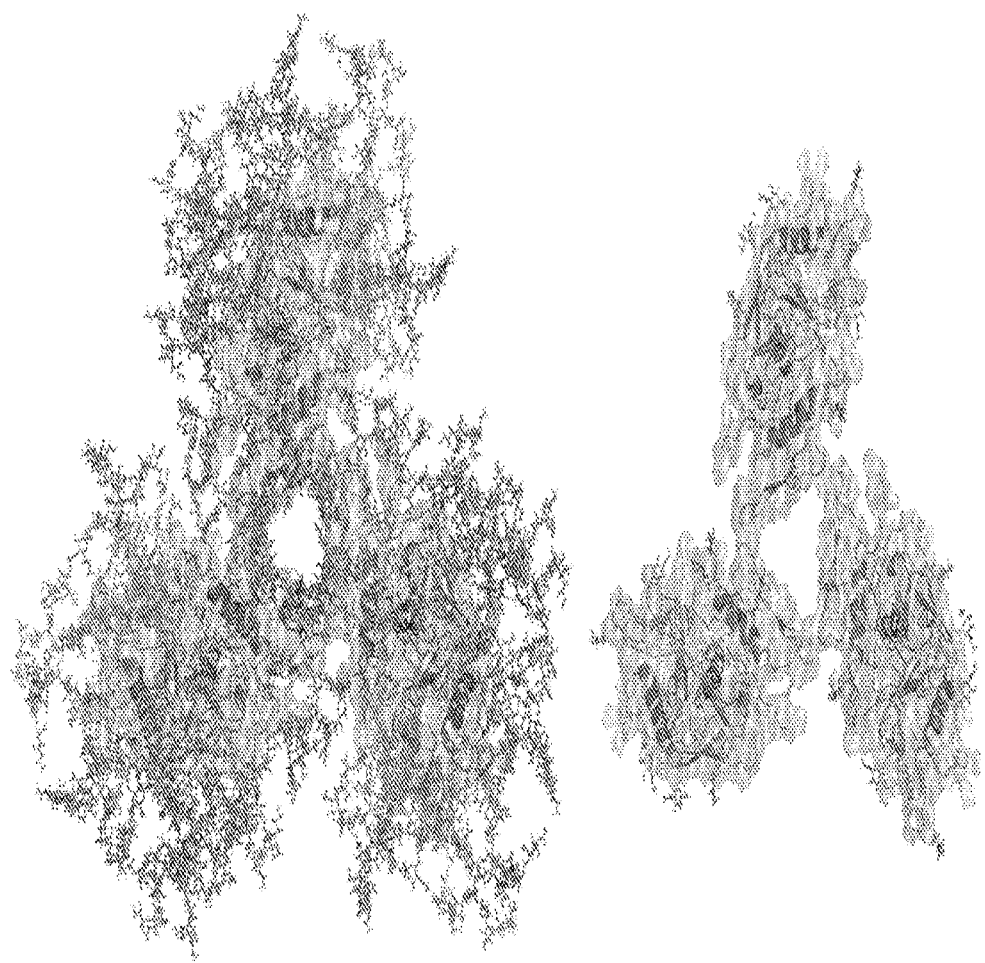
FIG. 21 shows human immunodeficiency virus envelope glycoprotein gp120 triimers in fully glycosylated form (Panel A) and mono-glycosylated form (Panel B). Models were created from PDB code 2BF1, with 13 possible complex-type N-glycans per monomer.

Thus, partial deglycosylation of Dengue virus glycoprotein E can be used to generate more effective and broad vaccines against flaviviruses. The result of partial deglycosylation of the Dengue type 3 virus E protein dimers is shown in the model depicted in FIG. 21. FIG. 21, panel B shows monoglycosylated Dengue E protein.

Hepatitis C virus (HCV) is the major etiological agent of human post-transfusion infection and community-acquired non-A, non-B hepatitis, infecting probably 1% of the population worldwide. HCV is a member of the Flaviviridae family, which includes the flaviviruses and the pestiviruses (Miller R H & Purcell R H, *Proc. Natl. Acad. Sci., USA* 87, 2057-2061 1990).

The hepatitis C virus (HCV) genome encodes two membrane-associated envelope glycoproteins (E1 and E2), which interact to form a noncovalent heterodimeric complex. HCV glycoproteins, E1 and E2, are heavily modified by N-linked glycosylation. The E1 protein consists of 192 amino acids and contains 5 to 6 N-glycosylation sites, depending on the HCV genotype. The E2 protein consists of 363 to 370 amino acids and contains 9-11 N-glycosylation sites, depending on the HCV genotype. (Maertens G. and Stuyver L. Genotypes and genetic variation of hepatitis C virus. In: The molecular medicine of viral hepatitis. Ed: Harrison T. J. and Zuckerman A. J. 1997).

A recent study has revealed that upon partial deglycosylation with endoglycosidase H only four of the five potential glycosylation sites at amino acid positions 196, 209, 234, 305 and 325, respectively, of HCV glycoprotein E1 are utilized. Mutations at positions N2 (196) and N3 (234) have only minor effects on the assembly of the E1E2 complex, whereas a mutation at position N1 (196) and predominantly at position N4 (305) dramatically reduces the efficiency of the formation of noncovalent E1E2 complexes. (Meunier J C. et al., *J. Gen. Virol.* (1999), 80, 887-896.)

Table 8 indicates the sequence of the Hepatitis C virus isolate HC-J6 envelope glycoprotein E1 (Okamoto, H., et al., J. Gen. Virol. 72(11), 2697-2704 (1991)) with potential N-glycosylation sites at positions 196, 209, 234, 305 and 325 underlined.

TABLE 7

Dengue virus glycoprotein E polypeptide sequence.

```
MRCVGIGNRD  FVEGLSGATW  VDVVLEHGSC  VTTMAKNKPT  LDIELLKTEV  TNPAVLRKLC   60

IEAKISNTTT  DSRCPTQGEA  TLVEEQDANF  VCRRTFVDRG  WGNGCGLFGK  GSLLTCAKFK  120

CVTKLEGKIV  QYENLKYSVI  VTVHTGDQHQ  VGNETTEHGT  IATITPQAPM  SEIQLTDYGA  180

LTLDCSPRTG  LDFNEMVLLT  MKEKSWLVHK  QWFLDLPLPW  TSGASTSQET  WNRQDLLVTF  240

KTAHAKKQEV  VVLGSQEGAM  HTALTGATEI  QTSGTTTIFA  GHLKCRLKMD  KLTLKGVSYV  300

MCTGSFKLEK  EVAETQHGTV  LVQVKYEGTD  APCKIPFSTQ  DEKGVTQNGR  LITANPIVTD  360

KEKPVNIETE  PPFGESYIVI  GAGEKALKLS  WFKKGSSIGK  MFEATARGAR  RMAILGDTAW  420

DFGSIGGAFT  SVGKLVHQVF  GTAYGVLFSG  VSWTMKIGIG  ILLTWLGLNS  RSTSLSMTCI  480

AVGMVTLYLG  VVVQA                                                      495
```

(SEQ ID NO: 13)

TABLE 8

Hepatitis C virus envelope glycoprotein E1 polypeptide sequence.

| | | | | | |
|---|---|---|---|---|---|
| AEVKNISTGY | MVTNDCTNDS | ITWQLQAAVL | HVPGCVPCEK | VGNTSRCWIP | VSPNVAVQQP 252 |
| GALTQGLRTH | IDMVVMSATL | CSALYVGDLC | GGVMLAAQMF | IVSPQHHWFV | QDCNCSIYPG 312 |
| TITGHRMAWD | MMMNWSPTAT | MILAYAMRVP | EVIIDIIGGA | HWGVMFGLAY | FSMQGAWAKV 372 |
| VVILLLAAGV | DA | | | | 384 |

(SEQ ID NO: 14)

Thus, partial deglycosylation of HCV glycoproteins E1 and E2 can be used to generate more effective and broad vaccines against HCV.

Human Immunodeficiency Virus (HIV) Vaccines

The human immunodeficiency viruses HIV-1 and HIV-2 and the related simian immunodeficiency viruses (SIV) cause the destruction of CD4+ lymphocytes in their respective hosts, resulting in the development of acquired immunodeficiency syndrome (AIDS). The entry of HIV into host cells is mediated by the viral envelope glycoproteins, which are organized into oligomeric, probably trimeric spikes displayed on the surface of the virion. These envelope complexes are anchored in the viral membrane by the gp41 transmembrane envelope glycoprotein. The surface of the spike is composed primarily of the exterior envelope glycoprotein, gp120, associated by non-covalent interactions with each subunit of the trimeric gp41 glycoprotein complex.

coreceptors CXCR4 and CCR5, the combined effects mediating the fusion and entry of HIV-1 into the host cell.

Because many N-linked glycans are highly conserved components of the HIV-1 envelope, they may themselves provide a promising target for neutralizing antibodies. The broadly neutralizing human monoclonal antibody 2G12 binds to an epitope comprising N-linked glycans that are attached to the gp120 glycoprotein. (Trloka A et al., J Virol 70: 1100-1108, 1996). Strains of HIV-1 in which N-linked glycosylation sites have been experimentally deleted or modified can become more sensitive to neutralization (Koch et al., 2003 Virology 313: 387-400.)

Mature gp120 contains 24 potential sites for N-glycosylation, as recognized by the sequence Asn-Xaa-Ser/Thr. (Kornfeld and Kornfeld, Ann Rev. Biochem. 54: 631-664, 1985). Table 9 indicates the 24 sites in the HIV-1 HXB2 sequence. Potential N-glycosylation sites are underlined.

TABLE 9

HIV gp120 polypeptide sequence.

| | | | | | |
|---|---|---|---|---|---|
| LWVTVYYGVP | VWKEATTTLF | CASDAKAYDT | EVHNVWATHA | CVPTDPNPQE | VVLVNVTENF 60 |
| NMWKNDMVEQ | MHEDIISLWD | QSLKPCVKLT | PLCVSLKCTD | LKNDTNTNSS | SGRMIMEKGE 120 |
| IKNCSFNIST | SIRGKVQKEY | AFFYKLDIIP | IDNDTTSYKL | TSCNTSVITQ | ACPKVSFEPI 180 |
| PIHYCAPAGF | AILKCNNKTF | NGTGPCTNVS | TVQCTHGIRP | VVSTQLLLNG | SLAEEEVVIR 240 |
| SVNFTDNAKT | IIVQLNTSVE | INCTRPNNNT | RKRIRIQRGP | GRAFVTIGKI | GNMRQAHCNI 300 |
| SRAKWNNTLK | QIASKLREQF | GNNKTIIFKQ | SSGGDPEIVT | HSFNCGGEFF | YCNSTQLFNS 360 |
| TWFNSTWSTE | GSNNTEGSDT | ITLPCRIKQI | INMWQKVGKA | MYAPPISGQI | RCSSNITGLL 420 |
| LTRDGGNSNN | ESEIFRPGGG | DMRDNWRSEL | YKYKVVKIEP | LGVAPTKAKR | RVVQREKR 478 |

(SEQ ID NO: 15)

The addition of asparagine (N)-linked polysaccharide chains (i.e., glycans) to the gp120 and gp41 glycoproteins of human immunodeficiency virus type 1 (HIV-1) envelope is not only required for correct protein folding, but also may provide protection against neutralizing antibodies as a "glycan shield." (Wei X et al., Nature 422: 307-312, 2003). The surface glycoprotein (gp120) of the human immunodeficiency virus type 1 (HIV-1) envelope, which represents the primary interface between the virus and the host environment, is one of the most heavily glycosylated proteins known to date, with nearly half of its molecular weight due to the addition of N-linked glycans. (Allan J S, et al. Science 228: 1091-1094, 1985.) The transmembrane glycoprotein (gp41) of the HIV-1 envelope is also glycosylated, but to a lesser extent. The addition of N-linked glycans is essential for HIV-1 gp120 to fold into the proper conformation to bind to the CD4 receptor, and influences the binding of alternative In the HIV-1 transmembrane glycoprotein gp41, the conserved glycosylation sites are at Asn621, Asn630 and Asn642.

Figure 20:
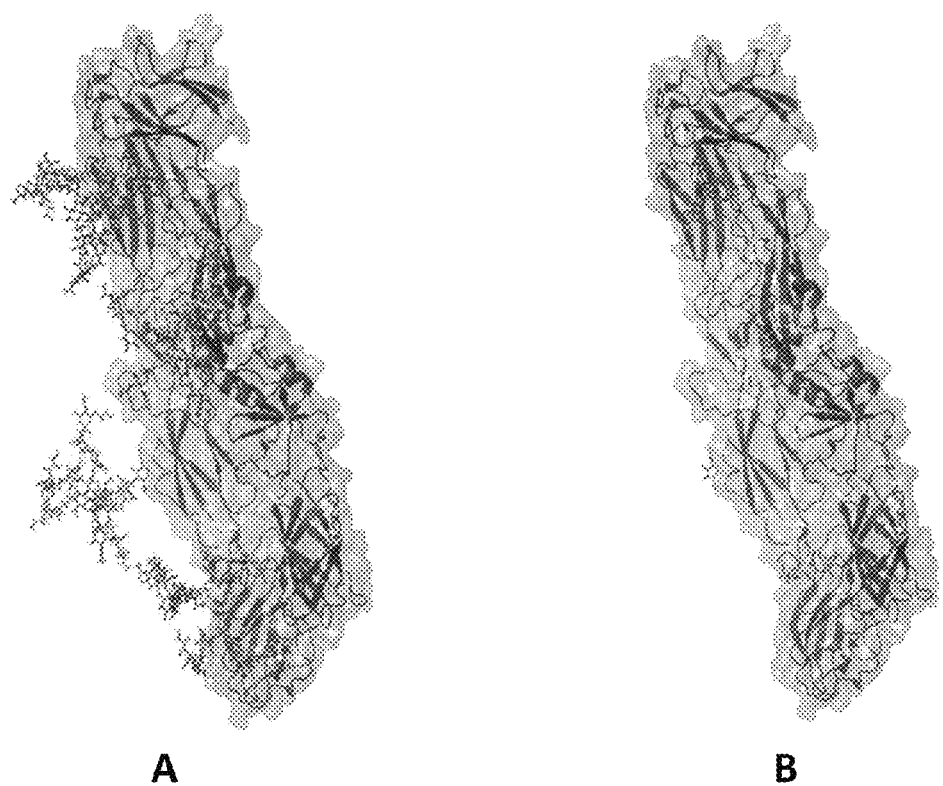
FIG. 20 shows Dengue type 3 virus envelope glycoprotein E dimers in fully glycosylated form (Panel A) and mono-glycosylated form (Panel B). Models were created from PDB code 1UZG, with 4 possible complex-type N-glycans with GlyProt server.

Thus, partial deglycosylation of HIV envelope protein gp120, or transmembrane protein gp41 can be used to generate more effective and broad vaccines against flaviviruses. The result of partial deglycosylation of the HIV gp120 protein trimers is shown in the model depicted in FIG. 20. FIG. 20, panel B shows monoglycosylated HIV gp120 protein trimers.

Methods for Making Partially Glycosylated Cell-Surface Glycoproteins

Polynucleotides of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention can be synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al.

(supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Expression of glycosylated HCV surface proteins in yeast is disclosed in WO 96/04385. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) *EMBO J.* 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia* larvae, in which the polypeptide of interest is expressed (Engelhard, E. K. et al. (1994) Proc. Natl. Acad. Sci. 91:3224-3227).

Partial deglycosylation of the recombinant surface glycoproteins can be accomplished by controlled use of combinations of various glycosidases, such as treating with neuraminidase to remove sialic acid, with alpha-1-mannosidase (Sigma) to cleave external mannose residues, or with endo F-N glycanase ((Boehringer Mannheim Biochemicals, Mannheim, Germany), which efficiently cleaves both N-linked high-mannose and complex glycans.

The HA peptides of the present invention also can be synthesized by processes which incorporate methods commonly used in peptide synthesis such as classical solution coupling of amino acid residues and/or peptide fragments, and, if desired, solid phase techniques. Any method for peptide synthesis well known in the art may be used, for example, Schroeder and Lubke, in "The Peptides", Vol. 1, Academic Press, New York, N.Y., pp. 2-128 (1965); "The Peptides: Analysis, Synthesis, Biology", (E. Gross et al., Eds.), Academic Press, New York, N.Y., Vol. 1-8, (1979-1987); Stewart and Young, in "Solid Phase Peptide Synthesis", 2nd Ed., Pierce Chem. Co., Rockford, Ill. (1984); Wild et al., Proc. Natl. Acad. Sci. USA, 89: 10537 (1992); and Rimsky et al., J Virol, 72: 986 (1998); Chan & White in "Fmoc Solid Phase Peptide Synthesis: A Practical Approach", Oxford University Press, (2000). In some embodiments, glycopeptides can be synthesized using glycosylated amino acids such that glycosylated amino acids, such as GlcNAc-Asn (V-Labs, Covington, La.), are incorporated at the appropriate glycosylation sites of the peptide.

Vaccines of the present disclosure can be employed as an antiviral agent by administering the peptide topically, intranasally, or through parenteral administration, such as through subcutaneous injection, intra-muscular injection, intravenous injection, intraperitoneal injection, or intra-dermal injection, to a warm-blooded animal, e.g., humans, horses, other mammals, etc. The antiviral peptides can be used individually or in combination. Additionally, the antiviral peptide may be administered alone or as part of a composition that further comprises one or more pharmaceutically acceptable carriers, the proportion of which is determined by the solubility and chemical nature of the peptide, chosen route of administration and standard biological administration. Because inventive peptides may target proteins on the surfaces of the virus and/or the cell, to ensure efficacy, the carrier in such formulations should be free or substantially free (e.g., better than 90, 95, 98, or 99 wt %) of proteins that bind to the peptides.

Pharmaceutical Compositions

According to another aspect, the vaccines and deglycosylated proteins of the present disclosure can be included in a pharmaceutical or nutraceutical composition or formulation together with additional active agents, carriers, vehicles, adjuvants, excipients, or auxiliary agents identifiable by a person skilled in the art upon reading of the present disclosure.

The vaccines of the present disclosure will advantageously comprise an adjuvant peptide in an effective adjuvant amount. As will be apparent to one skilled in the art, the optimal concentration of the adjuvant peptide or peptides will necessarily depend upon the specific peptide(s) used, the characteristics of the patient, the immunogen used, and the nature of the viral infection for which the treatment or prophylaxis is sought. These factors can be determined by those of skill in the medical and pharmaceutical arts in view of the present disclosure. In general, the adjuvant peptides are most desirably administered at a concentration level that will generally afford adjuvant activity without causing any harmful or deleterious side effects. Generally, an effective adjuvant amount is desired. An effective adjuvant amount refers to an amount of an adjuvant peptide which is capable of stimulating an immune response to an administered immunogen.

Suitable adjuvants for inclusion in compositions of the present disclosure include those that are well known in the art, such as complete Freund's adjuvant (CFA) that is not used in humans, incomplete Freund's adjuvant (IFA), squalene, squalane, alum, and various oils, all of which are well known in the art, and are available commercially from several sources, such as Novartis (e.g., MF59 adjuvant).

The pharmaceutical or nutraceutical compositions preferably comprise at least one pharmaceutically acceptable carrier. In such pharmaceutical compositions, the vaccine or deglycosylated protein forms the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration.

Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzylalcohol or methyl parabens; antioxidants such as ascorbic acid or sodium bisulfite; chelating agents such as ethylenediamine tetraacetic acid; buffers such as acetates. citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Suitable pharmaceutically acceptable carriers for the compositions containing the peptides are described in the standard pharmaceutical texts. See, e.g., "Remington's Pharmaceutical Sciences", 18th Ed., Mack Publishing Company, Easton, Pa. (1990). Specific non-limiting examples of suitable pharmaceutically acceptable carriers include water, saline, dextrose, glycerol, ethanol, or the like and combinations thereof. In addition, if desired, the composition can further contain minor amounts of auxiliary substances such as wetting or emulsifying agents, pH buffering agents that enhance the antiviral effectiveness of the composition.

Subject as used herein refers to humans and non-human primates (e.g. guerilla, macaque, marmoset), livestock animals (e.g., sheep, cow, horse, donkey, and pig), companion animals (e.g., dog. cat), laboratory test animals (e.g., mouse, rabbit. rat, guinea pig. hamster), captive wild animals (e.g., fox. deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

For parenteral administration, the peptides of the present disclosure or vaccines therefrom may be administered by intravenous, subcutaneous, intramuscular, intraperitoneal, or intradermal injection, alone or in compositions further comprising pharmaceutically accepted carriers. For administration by injection, it is preferred to use the antiviral peptide in a solution in a sterile aqueous vehicle which may also contain other solutes such as buffers or preservatives as well as sufficient quantities of pharmaceutically acceptable salts or of glucose to make the solution isotonic. The antiviral peptides of the present disclosure can be obtained in the form of therapeutically acceptable salts that are well-known in the art.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline. bacteriostatic water, Cremophor EL™ (BASF, Parsippany. N.J.) or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing. for example, water, ethanol, polyol (for example, glycerol, propylene glycol, and liquid polyetheylene glycol, and the like), and suitable mixtures thereof.

The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active composition in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying, which yields a powder of the active ingredient plus any additional desired ingredient from a previously sterile-filtered solution thereof.

Vaccines may also be administered orally. Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such ascolloidal silicon dioxide; a sweetening agent such as sucrose or saccharin; or a flavoring agent such as peppermint, methyl salicylate, or orange flavoring.

Because the peptides and vaccines of the present disclosure have shown activity against respiratory viruses, they can also be delivered locally to the respiratory system, for example to the nose, sinus cavities, sinus membranes or lungs. The peptide(s), vaccines, or pharmaceutical compositions containing one or more peptides or vaccines, can be delivered to the respiratory system in any suitable manner, such as by inhalation via the mouth or intranasally. The present compositions can be dispensed as a powdered or liquid nasal spray, suspension, nose drops, a gel or ointment, through a tube or catheter, by syringe, by packtail, by pledget, or by submucosal infusion. The peptides or vaccines may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the peptide and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898. The latter-cited U.S. patents are incorporated herein by reference and for all purposes. A propellant for an aerosol formulation may include compressed air, nitrogen, carbon dioxide, or a hydrocarbon based low boiling solvent. The peptides or vaccines of the present disclosure can be conveniently delivered in the form of an aerosol spray presentation from a nebulizer or the like. In some aspects, the active ingredients are suitably micronised so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. In one embodiment, one or more of the peptides or vaccines are packaged into a device that can deliver a predetermined, and generally effective, amount of the peptide via inhalation, for example a nasal spray or inhaler.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to implementations, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, which is incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

It will be appreciated by those skilled in the art that reference herein to treatment extends to prophylaxis as well as the treatment of established infections or symptoms. The peptides and vaccines of the present disclosure may be administered therapeutically or prophylactically. Treatment is preferably commenced before or at the time of infection or at the time the mammal is exposed to a virus that is capable of causing a viral respiratory infection, and continued until virus is no longer present or active in the respiratory tract. However, the treatment can also be commenced post-infection, after the mammal has been exposed to a virus that is capable of causing a viral respiratory infection, or after the appearance of established symptoms of infection.

It will be further appreciated that the amount of an antiviral peptide of the present disclosure that is useful in treatment or prevention of influenza will vary not only with the particular peptide selected but also with the route of administration, the nature of the condition being treated, and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

The peptide or vaccine may be conveniently administered in unit dosage form, for example, containing 10 to 1500 mg, conveniently 20 to 1000 mg, most conveniently 50 to 700 mg of active ingredient per unit dosage form, e.g. 1 mg/kg equates to 75 mg/75 kg of body weight.

Preferably the concentration of immunogen for each strain of the influenza virus for inclusion in the vaccine is an amount which induces an immune response without significant, adverse side effects. Such amount will vary depending on which immunogen is used and the type and amount of adjuvant peptide included in the vaccine. Typically, a vaccine will comprise immunogen in an amount of from about 1 to about 1000 μg per ml, more preferably from about 3 to about 300 μg per ml and most preferably about 10 μg to about 15 μg per ml, as measured by a SRD assay. Following an initial vaccination, subjects being vaccinated may receive one or several booster immunizations adequately spaced thereafter.

Toxicity and therapeutic efficacy of such compositions may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected location to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1: Gene Construct for HA Expression

The Influenza H5N1 HA sequence was from the consensus H5, CHA5 (Chen M W, et al. (2008) Proc Natl Acad Sci USA 105:13538-13543). The codons of CHA5 were optimized for expression by using human codons. The original viral protease cleavage site PQRERRRKKRG (SEQ ID NO: 1) was mutated to PQRERG (SEQ ID NO: 2) in order to prevent proteins from the enzymatic cleavage to form HA I and HA2. The transmembrane region (residues: 533-555) was replaced with the additional residues (SEQ ID NO: 3)
*LVPRGS*PGSGYIPEAPRDGOAYVRKDGEWVLLSTFLGHHHHHH at the C terminus of the HA construct, where the thrombin cleavage site is in italics, the bacteriophage T4 fibritin foldon trimerization sequence is underlined, and the His-tag is in bold (Stevens J. et al. (2006) Science 312:404-410). The modified HA sequence was cloned into pTT vector for protein expression (Durocher Y, et al. (2002) Nucleic Acids Res 30:E9).

Example 2: Protein Expression and Purification

The plasmid that encodes the secreted HA was transfected into the human embryonic kidney cell lines of either HEK293EBNA (ATCC number CRL-10852) or the GnTI-HEK293S cells (Reeves P J, et al. (2002) Proc Natl Acad Sci USA 99:13419-13424) by using polyethyleneimine and was cultured in Freestyle 293 expression medium (Invitrogen, Carlsbad, Calif.) supplemented with 0.5% bovine calf serum. The supernatant was collected 72 h after transfection and cleared by centrifugation. HA proteins were purified with Nickel-chelation chromatography as previously described (Wei C J, et al. (2008) J Virol 82:6200-6208) to obtain fully glycosylated $HA_{fg}$ and high-mannose-type $HA_{hm}$. To obtain the HA protein without sialylation—the desialylated $HA_{ds}$—the purified protein was treated with 20 mM *Clostridium* neuraminidase (NA; Sigma) for 2 h at 37° C. After the NA treatment, the protein was purified again to be separated from the NA. The purified $HA_{hm}$ was treated with Endo H (NEB) for 2 h at 37° C. to produce HA protein with a single GlcNAc at the glycosylation sites, the monoglycosylated $HA_{mg}$. All purified HA proteins were analyzed with SDS PAGE, glycan array and the mass spectrometry (MS).

Example 3: Release of N-Glycans from Glycoproteins for MS Analysis

The purified HA glycoproteins were reduced with 10 mM dithiothreitol (DTT, Sigma) at 37° C. for 1 hour. Reduced sample was then alkylated by 50 mM Iodoacetamide (IAA, Merck) in the dark for 1 hr and then was desalted by double distilled ($ddH_2O$) and dried in a speed vacuum. The reduced and alkylated HA protein extracts were first digested with trypsin (Roche) in an approximate ratio of enzyme to protein at 1:20 (w/w) in 50 mM ammonium bicarbonate buffer pH 8.3 at 37° C. for 4 hrs, followed by secondary typsin (Roche) digestion, and then loaded on to reverse phase C18 Sep-Pak cartridge (Waters Corp). The Sample were furthermore incubated with N-glycosidase F (Roche) in 50 mM ammonium bicarbonate pH 8.3 at 37° C. for 16 hrs, and with two more N-glycosidase F incubations. Released N-glycans were separated from peptides/glycopeptides by C18 Sep-Pak cartridge procedure with N-glycans collected in 5% acetic acid (AcOH), the flow-through fraction. The peptides were eluted in 20%, 40% and 60% 1-propanol with 5% AcOH.

Example 4: MALDI-MS and MS/MS Analysis

All glycan samples were permethylated using the NaOH/dimethyl sulfoxide slurry method. The NaOH/DMSO slurry was mixed with dried glycan samples in screw-capped glass tube and 300 μL iodmethane (Merck) was added into tube, and the tube was gently vortexed for 25 min. Reaction was terminated by adding ~1 ml ddH2O drop-wise, and then an equal volume of chloroform was added. Permethylated glycans were extracted into the bottom organic layer and additional NaOH as well as other hydrophilic contaminants were removed by repeated extraction with $ddH_2O$. Chloroform was evaporated by nitrogen gas. For glycan profiling, permethylated glycans in acetonitrile were mixed 1:1 with 10 mg/ml of 2,5-dihydroxybenzoic acid (DHB) in 50% acetonitrile, spotted on heated target plate, and recrystallized on-plate with acetonitrile. Data acquisition was performed on ABI 4700Proteomics Analyzer (Applied Biosystems) operated in the reflectron mode. Laser shots (5 Hz; 10 shots per spectrum) were accumulated until a satisfactory signal to noise ratio was achieved when combined and smoothed. On the TOF/TOF instrument, high-energy CID MS/MS data were manually acquired and typically comprised a total of 40 sub-spectra of 125 laser shots at a laser energy setting of 5000-5500.

Example 5: Glycan Microarray Fabrication

Twenty-four sialic acid-containing glycans designed for HAs were prepared chemically and used for array fabrication. Microarrays were printed (BioDot; Cartesian Technologies) by robotic pin (SMP3; TeleChem International) deposition of ~0.7 nL of various concentrations of amine-containing glycans in printing buffer (300 mM phosphate buffer, pH 8.5, containing 0.005% Tween 20) from a 384-well plate onto NHS-coated glass slides (Nexterion H slide; SCHOTT North America). The slides for sialosides were spotted with solutions of glycans 1-17 and 21-27 with concentrations of 100 µM in each row for one glycan from bottom to top, with 12 replicates horizontally placed in each subarray, and each slide was designed for 16 grids for further incubation experiments. Printed slides were allowed to react in an atmosphere of 80% humidity for an hour followed by desiccation overnight, and they were stored at room temperature in a desiccator until use. Before the binding assay, these slides were blocked with ethanolamine (50 mM ethanolamine in borate buffer, pH 9.2) and then washed with water and PBS buffer, pH 7.4, twice.

Example 6: Hemagglutinin Labeling with Cy3-NHS Ester

Each HA protein sample was diluted with PBS (pH=7.4) to the final concentration of I mg/mL, and then labeled with Cy3Mono NHS Ester (5 µL, 0.2 mg/ml) (GE Healthcare, UK). After the reactions had proceeded 18 hr on ice, 20 µL of 500 mM of glycine in PBS was added to each tube to quench the reactions. Then the solutions were incubated on ice for an additional 30 min. Non-reactive dye molecules were removed by passing each solution through a size exclusion spin filter (Microcon YM-30, Millipore, USA) with a molecular weight cutoff of 30 kDa. In order to obtain the ratio of dye/protein, each sample of labeled protein was diluted with PBS for the dual absorbance measurements at 280 nm (for protein) and at 552 nm (for Cy3; the molar extinction coefficient is150,000 $M^{-1}cm^{-1}$ at this wavelength) by using NanoDrop ND-IOO Spectrophotometer (NanoDrop Technologies, USA). After correcting the calculation for the absorbance of CyDye at 280 nm (approximately 8% of the absorbance at 552 nm), the ratios of dye/protein were generated from the results of dual-absorbance measurements.

Example 7: Indirect Binding Assay

HA glycosylated variants were prepared in 0.005% Tween 20/PBS buffer, pH 7.4, and added to cover the grid on glycan array with application of a coverslip. After incubation in a humidified chamber with shaking for 1 h, the slides were washed three times with 0.005% Tween 20/PBS buffer, pH 7.4. Next, rabbit anti-H5N1 HA antibody was added to the slides and incubated in a humidified chamber for 1 h. After washing the slides with 0.005% Tween 20/PBS buffer three times, Cy3-conjugated goat anti-rabbit IgG antibody was added to the slides and incubated in a humidified chamber for another 1 h. The slides were washed three times with 0.05% Tween 20/PBS buffer, pH 7.4; three times with PBS buffer, pH 7.4; and three times with H2O, and then dried. The slides were scanned at 595 nm (for Cy3) with a microarray fluorescence chip reader (GenePix Pro 6.0; Molecular Devices).

Example 8: Direct Binding Assay

Cy3-labeled HA proteins with different glycosylation were prepared in 0.005% Tween 20IPBS buffer (pH 7.4) and added to cover the grid on glycan array with application of a coverslip. After incubation in a humidifying chamber with shaking for 1 h, the slides were washed three times with 0.005% Tween 20/PBS buffer (pH 7.4), three times with PBS buffer (pH 7.4), and three times with $H_2O$ and dried. The slide was scanned at 595 nm (for Cy3) with a microarray fluorescence chip reader (GenePix Pro 6.0, Molecular Devices, USA).

Example 9: Microneutralization Assay

The freshly prepared H5N1 (NIBRG-14) virus (National Institute for Biological Standards and Control, Potters Bar, U.K.) was quantified with the median tissue culture infectious dose ($TCID_{50}$). The 100-fold $TCID_{50}$ of virus was mixed in equal volume with 2-fold serial dilutions of serum stock solution in 96-well plates and incubated for 1 h at 37° C. The mixture was added onto the MDCK cells ($1.5 \times 10^4$ cells per well) on the plates, followed by incubation at 37° C. for 16-20 h. The cells were washed with PBS, fixed in acetone/methanol solution (vol/vol 1:1), and blocked with 5% skim milk. The viral antigen was detected by indirect ELISA with a mAb against influenza A NP (Sui J H, et al. (2009) Nat Struct Mol Biol 16:265-273).

Example 10: Mice, Vaccination, and Challenge

Female 6- to 8-week-old BALB/c mice (n=15) were immunized intramuscularly with 20 µg of purified $HA_{fg}$ or $HA_{mg}$ proteins in 50 µL of PBS, pH 7.4, and mixed with 50 µL of 1 mg/mL aluminum hydroxide (Alum; Sigma) at weeks 0 and 2. Blood was collected 14 days after immunization, and serum samples were collected from each mouse. The immunized mice were challenged intranasally with a genetically modified H5N1 virus, NIBRG-14, with a lethal dose (100-fold lethal dose to 50% of mice). The mice were monitored daily for 14 days after the challenge for survival. All animal experiments were evaluated and approved by the Institutional Animal Care and Use Committee of Academia Sinica.

Example 11: Hemagglutination (HA) Assay

Hemagglutination of chicken red blood cells (cRBCs, Lampire Biological Laboratories, Pipersville, Pa.) is carried out in round bottom 96-well microtiter plates by preparing two-fold dilutions of viral samples in PBS, as described in Jones, et al., Journal of Virology, 80(24):11960-11967 (2006). Titer is reported as hemagglutinating units per 50 µL (HAU/50 µL) of sample.

Example 12: Purification of Viral Hemagglutinin

Viron-associated hemagglutinin (HA) was purified from influenza virus particles as described in Johansson, et al., Journal of Virology, 1989, Vol. 63(3), p. 1239-1246, with modifications. Briefly, virus is collected from the allantoic fluid of infected hen's eggs and sucrose purified as described above. Pellets are resuspended in 0.5 mL of sodium acetate buffer (0.05 M sodium acetate, 2 mM CaCl.sub.2, 0.2 mM EDTA, pH to 7.0), homogenized through an 18-gauge needle, and mixed with an equal volume of 15% octylglucoside (octyl-β-d-thioglucoside; Fisher Scientific, Norcross, Ga.) in sodium acetate buffer, followed by vigorous vortexing for 5 minutes. This suspension is centrifuged at 18,400×g for 60 minutes at 4° C., and the supernatant carefully removed and reserved as the HA-rich fraction. Two percent aqueous cetyl trimethyl-ammonium bromide (CTAB, Bio-World, Dublin, Ohio) is added to the HA fraction to a final concentration of 0.1% CTAB, and the sample is applied to a DEAE-Sephadex (A-50; GE Healthcare, Uppsala, Sweden) ion-exchange column (bed, 0.7 cm×6.0 cm) previously swollen and equilibrated with 0.05 M Tris-hydrochloride (pH 7.5) containing 0.1% octylglucoside. Twenty 0.5 mL fractions were collected by gravity with low salt HA elution buffer (0.05 M TrisHCl, 0.1 M NaCl, 0.1% Triton X-100, pH to 7.5) and again with a high salt HA elution buffer (0.05 M TrisHCl, 0.2 M NaCl, 0.1% Triton X-100, pH to 7.5). Individual fractions are assayed for HA activity and analyzed for purity by SDS-polyacrylamide gel electrophoresis under non-reducing conditions followed by staining with colloidal Commassie. Protein concentration is determined by BCA assay as per manufacturer's instructions (Pierce, Rockford, Ill.).

Example 13: Array Data Analysis

The software GenePix Pro (Axon Instruments) was used for the fluorescence analysis of the extracted data. The local background was subtracted from the signal at each spot. The spots with obvious defects, no detectable signal, or a net fluorescence of <100 were removed from the analysis. The "medians of ratios" from replicate spots were averaged in the same array. The profiling of HA binding to the array (FIG. 2, panel A) and the determination of association constant (FIG. 2, panel B) were performed under the same conditions on the same array to ensure the data were normalized.

To determine the $K_{D,surf}$ value, the equilibrium binding data were analyzed by fitting the data to the Langmuir isotherms (equation 1), assuming that ligands bound to one or two independent sites, using the commercial nonlinear regression program GradPad PRISM (GraphPad).

$F_{max}$ is the maximum fluorescence intensity, a measure of the amount of active carbohydrate on the surface; (P) is the total HA proteins concentration, and $K_{D,surf}$ is the equilibrium dissociation constant between the surface carbohydrates and the proteins.

The $K_{D,surf}$ values of each sample were repeated and calculated at least 4 times to derive mean of $K_{D,surf}$. By using $K_{D,surf}$ values, the thermodynamic parameters can be derived from the equations (2) and (3).

$$F_{obs}=F_{max}(P)/(K_{D,surf}+(P)) \quad \{\text{Equation 1}\}$$

$$K_{D,surf}=K_{A,surf}^{-1} \quad \{\text{Equation 2}\}$$

$$\Delta G_{multi}=RT \ln(K_{A,surf}) \quad \{\text{Equation 3}\}$$

$K_{A,surf}$ represents the association constants in equation (1). In equation (2), R=1.987 cal mol$^{-1}$K$^{-1}$; T is the absolute temperature, and the experiments were performed at 298 K. These values of each sample were calculated by using Microsoft Excel. The statistical analysis of $K_{D,surf}$ in different HA glycoforms was performed with one-way ANOVA by using GraphPad PRISM (GraphPad).

Example 14: Determination of HA-Specific Antibodies in Serum by ELISA

The HA proteins were purified from HEK293 and coated on the 96-well plates (5 µg/mL) overnight. The mouse serum was diluted 100-fold to be the stock serum for the measurement of HA binding. The HA-coated plates were incubated with serum in 2-fold serial dilutions for 1 h. HA-specific IgG was detected by using HRP-conjugated anti-mouse antibodies. The endpoint dilution was calculated by picking the dilution for which the readout was above that of the 1:50 dilution of preimmune serum (Stevens J. et al. (2006) Science 312:404-410). Antiserum from rabbit was prepared by LTK BioLaboratories. Rabbit was immunized by about 0.25-0.35 mg of HA proteins mixed with complete or incomplete adjuvants. Blood was collected from rabbit after six immunizations, with a schedule of one immunization every 2 weeks.

Example 15: Glycosylation Site Analysis for HA

A total of 297 full-length HA sequences from H1, H3, and H5 influenza viruses were retrieved from the National Center for Biotechnology Information database and aligned by ClustalW2 program in EMBL-EBI (Larkin M A, et al. (2007) Bioinformatics 23:2947-2948). The sequences date from the years 1918 to 2000s and were isolated from humans. To reduce redundancy, strains in one country were only selected one time for analysis. Sequences used for alignment include: H1 (AAX56530, AAY78939, ABA18037, ABB51962, ABC42750, ABD60867, ABD62061, ABE11690, ABF47869, ABF82830, ABF82852, ABG37362, ABI19015, ABI21211, ABI95294, ABI96103, ABK39995, ABK57092, ABK57093, ABK79970, AB032948, AB032970, ABR15885, ABS71664, and ABS76427); H3 (AAT08000, AAT12654, AAX11455, AAY58320, AAZ32943, AAZ43394, ABA26700, ABA26777, ABB51961, ABB71825, ABC42596, ABC42607, ABC42629, ABC43017, ABD15713, ABD59850, ABD61359, ABF17954, ABG37450, and ABG37461); H5 (AAS65618, AAT39065, AAT73273, AAT73274, AAT73275, AAT84153, AAV32636, ABC72655, ABD28180, ABD28182, ABE97624, ABI16504, ABI36144, ABI36439, AB010181, AB036644, and ABP51968). N-linked glycosylations of HA sequences were predicted by center of biological sequence analysis prediction severs (www.cbs.dtu.dk/services/). For glycosylation of asparagine (Asn), the sequences contain amino acid pattern Asn-$X_{aa}$-(Ser/Thr), where Xaa can be any amino acid except for proline (Gavel Y, et al. (1990) Protein Eng 3:433-442), followed by serine or threonine. The results for data analysis were prepared by using the PRISM program (GraphPad) and Jalview (Waterhouse A M, et al. (2009) Bioinformatics 25:1189-1191).

Example 16: Chemical Method for Synthesis of HA Glycopeptides

The stepwise synthesis of HA glycopepides can be carried out by the dimethylphosphinothioic mixed anhydride (Mpt-MA) method (Inazu, T., et al. (1997) in Peptide Chemistry 1996 (Kitada, C. ed.) pp. 41-44, Protein Research Foundation, Osaka). HA glycoproteins can be synthesized by a thioester method with a consensus sequence "Asn-X-Ser/Thr" for N-glycosylation but no sugar chains. The peptide fragment is prepared by an automatic synthesizer using a supplied Boc-strategy program. The coupling reaction is performed by using DCC/HOBt as the activating reagent. Asn(GlcNAc) residue is coupled by a Mpt-MA method using Boc-Asn(GlcNAc)-OH (3 equiv). The coupling reactions are performed for 1 h and repeated with monitoring. After treatment with anhydrous HF containing 10% anisole and HPLC purification, a glycopeptide thioester is obtained. This glycopeptide thioester segment is coupled with the other peptide segment, which was prepared separately by the thioester segment condensation method. After deprotections and disulfide bond formation, the GlcNAc-HA analog is obtained.

Alternately, a convergent method synthesis of HA glycopepides can be carried out by the coupling reaction of the β-carboxyl group of peptidyl Asn with glycosylamine. (See Cohen-Abisfeld, S. T., and Lansbury, P. T. (1993) J. Am. Chem. Soc. 115, 10531-10537)

Example 17: Chemo-Enzymatic Method for Synthesis of HA Glycopeptides

The preparation of a glycopeptide containing a complex oligosaccharide can be performed by using enzymatic methods in conjunction with chemical methods. Synthesis of N-glycopeptides can be performed using the transglycosylation activity of endo-β-N-acetylglucosaminidase (endo-β-GlcNAc-ase). (Takegawa, K., et al. (1995) J. Biol. Chem. 270, 3094-3099). Endo-β-GlcNAc-ase hydrolyzes the glycosidic bond between the N,N'-diacetylchitobiose moiety of a N-linked oligosaccharide, and transfers the released oligosaccharide fragment to a hydroxyl compound. The synthesis of N-glycopeptides using endo-β-GlcNAc-ase can be performed in two steps. First, a GlcNAc-containing peptide is prepared by a chemical route. Then an oligosaccharide fragment of a glycosyl donor is transferred to the GlcNAc moiety of the glycopeptide as a glycosyl acceptor by the transglycosylation reaction of endo-β-GlcNAc-ase.

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of manufacturing an immunogenic composition the method comprising:

(i) providing a viral glycoprotein, or immunologically active fragment thereof, which comprises a glycan bound to a glycosylation site of the viral glycoprotein, or the immunologically active fragment thereof;

(ii) removing a portion of the glycan to form a truncated glycan, which consists of one, two, or three sugar residues, to produce the partially glycosylated viral glycoprotein comprising the truncated glycan; and (iii) formulating the partially glycosylated viral glycoprotein or immunologically active fragment thereof produced in step (ii) into an immunogenic composition, which further comprises an adjuvant.

2. The method of claim 1, wherein the viral glycoprotein or the immunologically active fragment thereof is produced in and isolated from a eukaryotic host cell.

3. The method of claim 2, wherein the eukaryotic host cell comprises a construct suitable for expressing the viral glycoprotein or the immunologically active fragment thereof.

4. The method of claim 2, wherein the eukaryotic host cell is selected from the group consisting of a yeast cell, an insect cell, a mammalian cell, and a human cell.

5. The method of claim 4, wherein the eukaryotic host cell is a HEK293E cell.

6. The method of claim 1, wherein step (ii) is performed by incubating the viral glycoprotein or the immunologically active fragment thereof set forth in (i) with a glycosidase, a neuraminidase, an alpha-1-mannosidase, an endo F glycanase, an endo N glycanase, an endoglycosidase H (Endo H), an enzyme that selectively digests the glycan at an N- or O-linked glycosylation site, or a combination thereof.

7. The method of claim 1, wherein step (ii) is performed by a chemical method that selectively digests the glycan at an N- or O-linked glycosylation site.

8. The method of claim 1, wherein the viral glycoprotein is selected from the group consisting of:

influenza virus neuraminidase, influenza virus hemagglutinin, RSV F glycoprotein, RSV G glycoprotein, herpes simplex virus glycoproteins gB, gC, gD, and gE, Chlamydia MOMP and PorB antigens, Dengue virus core protein, Dengue virus matrix protein measles virus hemagglutinin, herpes simplex virus type 2 glycoprotein gB, poliovirus I VP1, envelope glycoproteins of HIV 1, hepatitis B surface antigen, pseudorabies virus g50 (gpD), pseudorabies virus II (gpB), pseudorabies virus III (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, bovine viral diarrhea glycoprotein 55, Newcastle disease virus hemagglutinin-neuraminidase, swine flu hemagglutinin, swine flu neuraminidase, infectious bovine rhinotracheitis virus glycoprotein E, infectious bovine rhinotracheitis virus glycoprotein G, infectious laryngotracheitis virus glycoprotein G, infectious laryngotracheitis virus glycoprotein I, hepatitis B virus core protein, equine influenza virus type A/Alaska 91 neuraminidase, equine influenza virus type A/Miami 63 neuraminidase, equine influenza virus type A/Kentucky 81 neuraminidase, equine herpes virus type 1 glycoprotein B, equine herpes virus type 1 glycoprotein D, bovine respiratory syncytial virus attachment protein (BRSV G), bovine respiratory syncytial virus fusion protein (BRSV F), bovine respiratory syncytial virus nucleocapsid protein (BRSVN), bovine parainfluenza virus type 3 fusion protein, bovine parainfluenza virus type 3 hemagglutinin neuraminidase, bovine viral diarrhea virus glycoprotein 48, bovine viral diarrhea virus glycoprotein 53, glycoprotein E of Dengue virus, glycoprotein E1 of human hepatitis C virus, and glycoprotein E2 of human hepatitis C virus.

9. The method of claim 1, wherein the adjuvant is selected from the group consisting of aluminum hydroxide, aluminum phosphate, both aluminum hydroxide and aluminum phosphate, incomplete Freund's adjuvant (IFA), squalene, squalane, alum, and MF59.

* * * * *